(12) United States Patent
Schiff et al.

(10) Patent No.: US 9,592,383 B2
(45) Date of Patent: Mar. 14, 2017

(54) SYSTEM AND METHODS FOR MULTI-SITE ACTIVATION OF THE THALAMUS

(71) Applicant: CORNELL UNIVERSITY, Ithaca, NY (US)

(72) Inventors: Nicholas Schiff, New York, NY (US); Keith Purpura, New York, NY (US); Jonathan Baker, Scarsdale, NY (US); Jae-Wook Ryou, Flushing, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 14/762,616

(22) PCT Filed: Jan. 23, 2014

(86) PCT No.: PCT/US2014/012781
§ 371 (c)(1),
(2) Date: Jul. 22, 2015

(87) PCT Pub. No.: WO2014/116850
PCT Pub. Date: Jul. 31, 2014

(65) Prior Publication Data
US 2015/0367133 A1    Dec. 24, 2015

Related U.S. Application Data

(60) Provisional application No. 61/755,842, filed on Jan. 23, 2013.

(51) Int. Cl.
*A61N 1/00*    (2006.01)
*A61N 1/36*    (2006.01)
*A61N 1/05*    (2006.01)

(52) U.S. Cl.
CPC ....... *A61N 1/36064* (2013.01); *A61N 1/0534* (2013.01); *A61N 1/36067* (2013.01);
(Continued)

(58) Field of Classification Search
CPC ............ A61N 1/36064; A61N 1/36067; A61N 1/36071; A61N 1/36082; A61N 1/36135; A61N 1/36139
See application file for complete search history.

(56) References Cited

U.S. PATENT DOCUMENTS 5,938,688 A  *  8/1999  Schiff ................. A61N 1/3605
                                                       607/45
8,024,049 B1     9/2011  Gilson et al.
(Continued)

OTHER PUBLICATIONS

International Preliminary Report on Patentability corresponding to PCT/US2014/012781, filed Jan. 23, 2014, mailed Aug. 6, 2015.
(Continued)

*Primary Examiner* — Robert N Wieland
(74) *Attorney, Agent, or Firm* — LeClairRyan, a Professional Corporation

(57) ABSTRACT

The present invention relates to a method to control a thalamic projecting fiber in a subject. This method involves providing a subject having a first stimulator and a second stimulator implanted in the subject's central thalamus. A stimulus signal generator is provided which is coupled to the first and second stimulators. Separate stimulus signals are provided from the stimulus signal generator to the first and second stimulators under conditions effective to control the thalamic projecting fiber in the subject. Also disclosed is an apparatus for deep brain stimulation.

28 Claims, 42 Drawing Sheets

(52) U.S. Cl.
CPC ..... *A61N 1/36071* (2013.01); *A61N 1/36082* (2013.01); *A61N 1/36107* (2013.01); *A61N 1/36135* (2013.01)

(56) References Cited

U.S. PATENT DOCUMENTS

| | | |
|---|---|---|
| 8,694,087 B2 | 4/2014 | Schiff |
| 2006/0217781 A1* | 9/2006 | John ................. A61N 1/36017 607/45 |
| 2009/0192568 A1 | 7/2009 | Whitehurst et al. |
| 2009/0319001 A1 | 12/2009 | Schiff |
| 2010/0042187 A1 | 2/2010 | Werder et al. |
| 2010/0114257 A1 | 5/2010 | Torgerson |
| 2011/0093043 A1 | 4/2011 | Torgerson et al. |
| 2014/0237073 A1 | 8/2014 | Schiff |

OTHER PUBLICATIONS

Schiff et al., "Behavioural Improvements With Thalamic Stimulation After Severe Traumatic Brain Injury," Nature 448 (02):600-604 (2007).

Shirvalkar et al., "Cognitive Enhancement With Central Thalamic Electrical Stimulation," PNAS 103(45):17007-17012 (2006).

Theodore et al., "Brain Stimulation for Epilepsy," The Lancet Neurology 3:111-118 (2004).

PCT International Search Report and Written Opinion corresponding to PCT/US2014/012781, mailed Apr. 15, 2014.

European Search Report for corresponding EP Application No. 14743377.5-1666, Aug. 22, 2016, pp. 1-7.

* cited by examiner

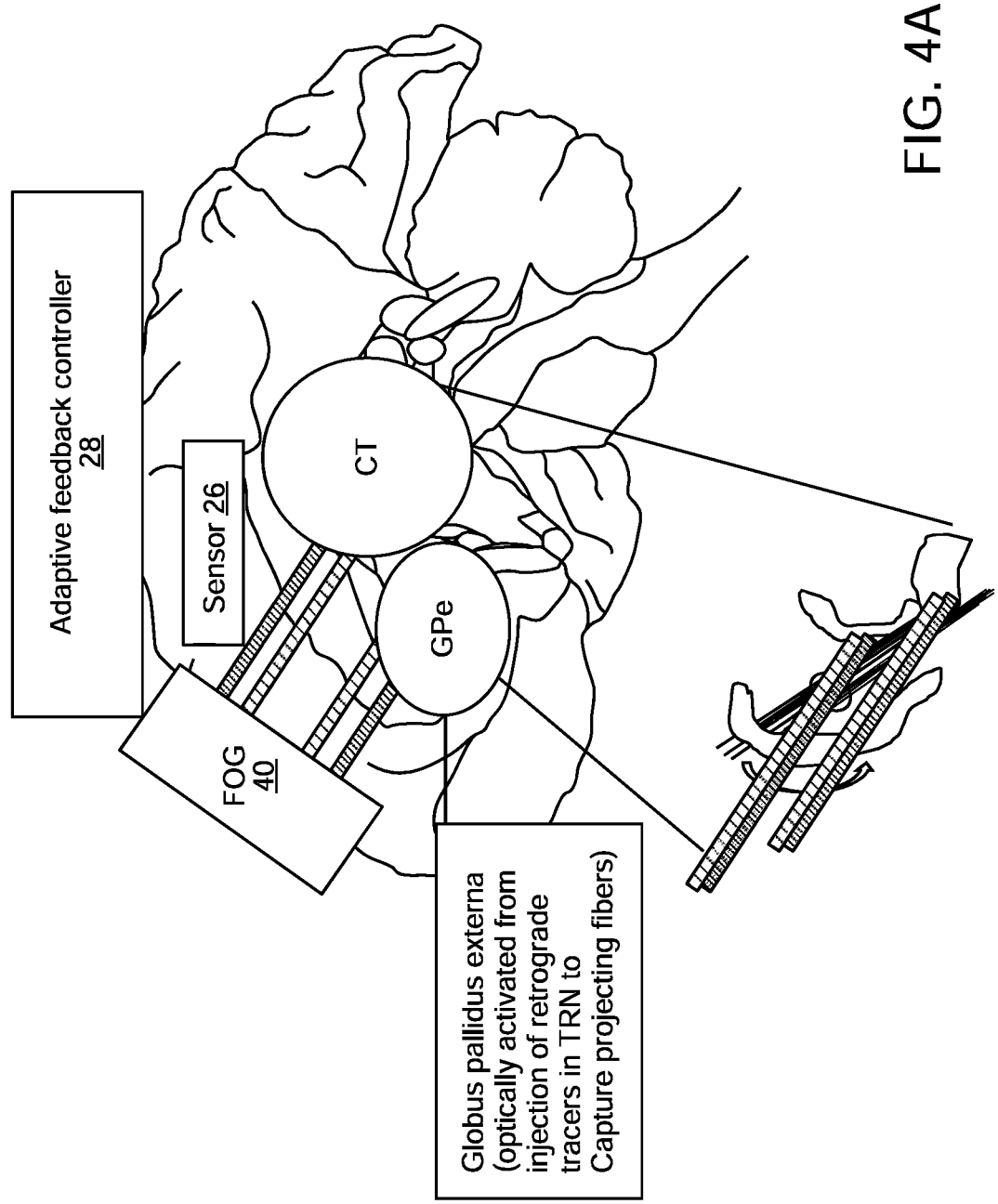

Frontal/Parietal systems
Frontal Eye Fields (FEF)
Supplementary Motor Area (SMA)
Anterior Cingulate Cortex (ACC)
Posterior Parietal Cortex (PPC)

'Arousal' systems
Basal Forebrain (BF) and Brainstem Cholinergic (LDT/PPT)
Locus Ceruleus (LC)
Mesencephalic Reticular Formation (MRF)

SYSTEM AND METHODS FOR MULTI-SITE ACTIVATION OF THE THALAMUS

This application claims the benefit of U.S. Provisional Patent Application Ser. No. 61/755,842, filed Jan. 23, 2013, which is hereby incorporated by reference in its entirety.

This invention was made with government support under grant number NS067249 awarded by National Institute of Neurological Disorders and Stroke. The government has certain rights in this invention.

FIELD OF THE INVENTION

The present invention is related to a system and methods for multi-site activation of the thalamus.

BACKGROUND OF THE INVENTION

Brain injuries which lead to impaired cognitive function remain the least explored area for active neurological intervention. Subjects who suffer severe brain injuries secondary to trauma, hypoxia, infection, and other etiologies typically preserve varying capacities for memory, attention, intention, and awareness. In many cases, these subjects fluctuate dramatically, and even those who regain independence in activities of daily living often fail to reestablish vocational re-entry or other functional levels secondary to persistent cognitive impairment. Such chronic cognitive impairment is typified by failures to recruit sufficient resources of 'executive functions,' beginning with vigilance or sustained attentional effort as a primary executive function. Parasuraman, "The Attentive Brain." Cambridge, Mass.:MIT Press (1998); Sarter et al., "More Attention Must Be Paid: The Neurobiology of Attentional Effort." *Brain Res Rev* 51:145-160 (2006). The executive functions further include working memory, motor intention, as well as planning and decision making capacity. Collectively, these executive functions are under joint control of frontal/prefrontal-thalamocortical and frontal/prefrontal-striatopallidal-thalamocortical forebrain systems. The nuclei of the central thalamus (intralaminar and paralaminar regions) play a key role in maintaining levels of activation across these systems and in turn are regulated by ascending projections from the brainstem "arousal systems." There has been a striking lack of therapeutic options for these patients with broad cognitive impairments resulting from multi-focal structural injuries, despite evidence through their behavioral fluctuations of a latent capacity to further optimize their brain function.

To date, studies in experimental animals demonstrate that electrical stimulation of the central thalamus can improve cognitive function in normal control animals recruiting a reserve capacity present across the forebrain connections of the frontal/prefrontal-thalamic and frontal/prefrontal-striato-pallidal-thalamocortical systems in the uninjured brain. Shirvalkar et al., "Cognitive Enhancement With Central Thalamic Electrical Stimulation," *Proc Natl Acad Sci USA.,* 103(45):17007-12 (2006); Mair et al., "Memory Enhancement With Event-Related Stimulation of the Rostral Intralaminar Thalamic Nuclei," *J Neurosci.* 28(52):14293-300 (2008); Shah et al., "Modulation of Arousal Regulation with Central Thalamic Deep Brain Stimulation," *Conf Proc IEEE Eng Med Biol Soc.* 3314-7 (2009); Smith et al., "A Bayesian Statistical Analysis of Behavioral Facilitation Associated with Deep Brain Stimulation," *J Neurosci Methods* 183(2):267-76 (2009); Schiff, "Central Thalamic Contributions to Arousal Regulation and Neurological Disorders of Consciousness," *Ann N Y Acad Sci.* 1129:105-18 (2008). A single-subject human study demonstrated the first proof of the concept that improved arousal regulation produced by stimulation of the central thalamus can facilitate a range of cognitively-mediated behaviors. Schiff et al., "Behavioural Improvements with Thalamic Stimulation After Severe Traumatic Brain Injury," *Nature* 448(7153):600-3 (2007). However, improved procedures for controlling and selecting sites within the central thalamus for such stimulation are needed.

The present invention is directed to overcoming these and other deficiencies in the art.

SUMMARY OF THE INVENTION

One aspect of the present invention relates to a method to control a thalamic projecting fiber in a subject. This method involves providing a subject having a first stimulator and a second stimulator implanted in the subject's central thalamus. A stimulus signal generator is provided which is coupled to the first and second stimulators. Separate stimulus signals are provided from the stimulus signal generator to the first and second stimulators under conditions effective to control the thalamic projecting fiber in the subject.

Another aspect of the present invention relates to an apparatus for deep brain stimulation. The apparatus includes at least two stimulators comprising first and second stimulators. The first and second stimulators include one or more electrodes. A stimulus signal generator is coupled to the first and second stimulators. The stimulus signal generator is configured to provide stimulus signals to the first and second stimulators. The stimulus signal generator selectively provides the stimulus signals to at least one of the one or more electrodes of the first and second stimulators causing a current to flow between first stimulator and second stimulator.

A further aspect of the present invention is directed to a method for regulating arousal level in a selected subject. The method includes providing the selected subject having a first stimulator and a second stimulator implanted in the subject's central thalamus. A stimulus signal generator coupled to the first and second stimulators is provided. Separate stimulus signals are provided from the stimulus signal generator to the first and second stimulators under conditions effective to regulate the arousal level of the subject.

Another aspect of the present invention is directed to a method for suppressing seizure activity in a selected subject. The method includes providing the selected subject having a first stimulator and a second stimulator implanted in the subject's central thalamus. A stimulus signal generator coupled to the first and second stimulators is provided. Separate stimulus signals are provided from the stimulus signal generator to the first and second stimulators under conditions effective to suppress seizure activity in the subject.

Yet another aspect of the present invention is directed to a method for normalizing movement in a selected subject. The method includes providing the selected subject having a first stimulator and a second stimulator implanted in the subject's central thalamus. A stimulus signal generator coupled to the first and second stimulators is provided. Separate stimulus signals are provided from the stimulus signal generator to the first and second stimulators under conditions effective to normalize movement in the subject.

The present invention provides artificial activation of neuronal elements within the thalamus of the human brain to modulate patterns of large-scale dynamics of the human corticothalamic system. Such activation advantageously serves to ameliorate direct effects of disease or trauma and related effects of disease and other conditions on goal directed behaviors, cognitive functions, and general health. The present invention may be utilized to improve cognitive function and behavioral responsiveness in brain-injured human subjects. The present invention may further provide treatment of epilepsy, movement disorders, and neuropsychiatric illness. The present invention provides novel methods for control of intrathalamic, thalamostriatal, and thalamocortical activation, using stimulation of outflow from the nuclei of the central thalamus and enpassant fibers from the brainstem to drive neuronal activity within the cerebral cortex, striatum, and other thalamic and subcortical systems. The methods can be used to drive neuronal activity in areas of the thalamus that are otherwise down-regulated or misregulated as a result of structural brain injury, neurological or psychiatric disease or condition, or alteration of the available neuronal populations with the specific brain regions. The present invention may be utilized to treat degenerative diseases, developmental brain disorder, or other mechanisms underlying brain dysfunction such as epilepsy, movement disorders, primary arousal disorders, and other conditions.

A method requiring two or more distinct sites of stimulation within the central thalamus is disclosed, which optimizes control of a dedicated system of thalamic nuclei including the intralaminar and paralaminar nuclei of the thalamus and fibers of passage within the areas of applied stimulation. The methods described also provide an approach to customization of placement and choice of stimulation method in the setting of manifold brain injury patterns that may impede the generically optimal strategy of stimulation to achieve the desired control of the thalamocortical projections from intralaminar and paralaminar nuclei and pattern of activation within the thalamic reticular nucleus ("TRN").

In an application of these methods two or more electrodes are placed within each central thalamus to bind the collection of closely collected fiber bundles containing projections from the central lateral and parafascicular intralaminar nuclei to the TRN and the medial dorsal tegmental tract ("DTTm") which contains cholinergic and glutamatergic fibers from the brainstem that project to the TRN. See Edlow et al., "Neuroanatomic Connectivity of the Human Ascending Arousal System Critical to Consciousness and Its Disorders," *J. Neuropathol. Exp. Neurol.* 71(6):531-46 (2012), which is incorporated by reference herein in its entirety. Electrical current is passed between at least one caudal electrode, which is set as a cathode, and at least one rostral electrode is set to be an anode.

Experimental results shown below indicate that behavioral effects achieved with the use of such an approach to electrical stimulation in this configuration is anisotropic with loss of effect in geometries with exchange of anode and cathode. In some injured brains, lesion patterns may preclude the instantiation of this optimal configuration to activate these specific projection fibers and configurations using multiple electrodes (n>2) or other stimulation methods in combination or alone (e.g. BION, optogenetic methods) would be applied with control of patterns of activation to approximate similar effects. In such an example, positioning the electrodes to place an electrical current across both the lateral dorsal tegmental tract ("DTTl"), which also contains cholinergic fibers, and positioning other electrodes across the DTTm to account for interruptions due to lesions could be employed.

BRIEF DESCRIPTION OF THE DRAWINGS

FIG. 4A is a partial side view and partial block diagram of a deep brain stimulation apparatus implanted in a brain utilizing a FOG system.

FIG. 20A illustrates the electrodes in the right central thalamus of the first animal. FIG. 20B illustrates the electrodes positioned bilaterally in the second animal.

FIG. 23A depicts the first animal's performance during the Vigilance task shown in FIG. 21. FIG. 23B depicts reaction times plotted as a function of trial number. FIGS. 23C-23D depict the animal's performance and reaction times during a session of the Memory Guided Saccade task as shown in FIG. 22. FIGS. 23E-23F depict the first animal's performance and reaction times during a Vigilance task as shown in FIG. 21 session where central thalamus deep brain stimulation amplitude and electrode geometry were fixed during the 1700 trials.

FIGS. 25A, C, E, G, I, and K illustrate the distribution of Log Odds Ratios ("LOR") of performance (correct vs. incorrect) comparing performance during central thalamus deep brain stimulation/performance prior to central thalamus deep brain stimulation at 20 Hz, 40 Hz, 150 Hz, 175 Hz, 200 Hz, and 225 Hz, respectively. FIGS. 25 B, D, F, H, J, and L illustrate the distribution of LOR of performance comparing performance during central thalamus deep brain stimulation/performance following central thalamus deep brain stimulation at 20 Hz, 40 Hz, 150 Hz, 175 Hz, 200 Hz, and 225 Hz, respectively. All amplitudes, frequencies, and electrode configurations are included (N=2007) from a total of 212 central thalamus deep brain stimulation sessions.

FIG. 26A illustrates LOR of performance during central thalamus deep brain stimulation/performance prior to central thalamus deep brain stimulation (N=883) versus central thalamus deep brain stimulation amplitude. FIG. 26B illustrates LOR of performance during central thalamus deep brain stimulation/performance following central thalamus deep brain stimulation (N=864) versus stimulation amplitude. All amplitudes, frequencies, and electrode configurations are included.

FIG. 27A illustrates distributions of reaction times during 165 central thalamus deep brain stimulation sessions (34,502 correct trials) at 20 Hz, 40 Hz, 150 Hz, 175 Hz, 200 Hz, and 225 Hz. FIG. 27B depicts a cumulative distribution function of the reaction time distributions shown FIG. 27A.

FIG. 28A shows the performance profile derived from the State-Space Model as described in Smith et al., "A Bayesian Statistical Analysis of Behavioral Facilitation Associated with Deep Brain Stimulation," *J. Neurosci. Methods* 183(2):267-76 (2009), which is incorporated herein by reference, and highlights the causal linkage between periods of continuous 20 Hz, 40 Hz, 150 Hz, 175 Hz, 200 Hz and 225 Hz central thalamus deep brain stimulation and fluctuations in the animals performance during 1320 contiguous trials. FIG. 28B shows reaction times plotted as a function of trial number.

FIG. 29A shows LOR of performance during central thalamus deep brain stimulation/performance prior to central thalamus deep brain stimulation (N=214) versus central thalamus deep brain stimulation amplitude. FIG. 29B shows LOR of performance during central thalamus deep brain stimulation/performance following central thalamus deep brain stimulation (N=177) versus stimulation amplitude. All amplitudes, frequencies, and electrode configurations are included (N=492) from a total of 33 central thalamus deep brain stimulation sessions.

FIG. 30A shows the average local field potential spectra recorded from one electrode positioned within the frontal eye field, containing well-isolated single unit activity. The average local feel potential spectra are separated for Correct and InCorrect trials, excluding all deep brain stimulation trials. FIG. 30B shows average local field potential spectra recorded from one electrode positioned within the dorsal caudate. Only 1.5 seconds of delay period activity in the Correct trials was included and then separated for trials with deep brain stimulation and without deep brain stimulation. FIG. 30C shows the peak local field potential power centered at 5 and 20 Hz (+/−2 Hz) for a single electrode positioned within the dorsal putamen during correct performance. The solid curves represent local field potential power during 200 Hz deep brain stimulation ON periods (188 correct trials) and the dashed curves represent local field potential power during deep brain stimulation OFF periods (137 correct trials). The Pre-Target, Target/Cue and Delay periods are noted and marked by vertical hashed lines (see Vigilance Task as illustrated in FIG. 21). FIG. 30D shows the first animal's performance profile during periods of continuous 150 and 200 Hz central thalamus deep brain stimulation. "Effective" cathode/anode configurations are highlighted with an asterisk. The five superimposed grayscale lines represent integrated power within select frequency bands: total power across the entire frequency range (0.1-100 Hz); power in the delta range (0.1-5 Hz); power in the alpha range (8-14 Hz); power in the beta range (15-25 Hz); power in the gamma range (25-90 Hz). Jackknife estimates of the 95% confidence intervals for each measure of integrated power are indicated by the dotted lines.

DETAILED DESCRIPTION OF THE INVENTION

Figure 1A:
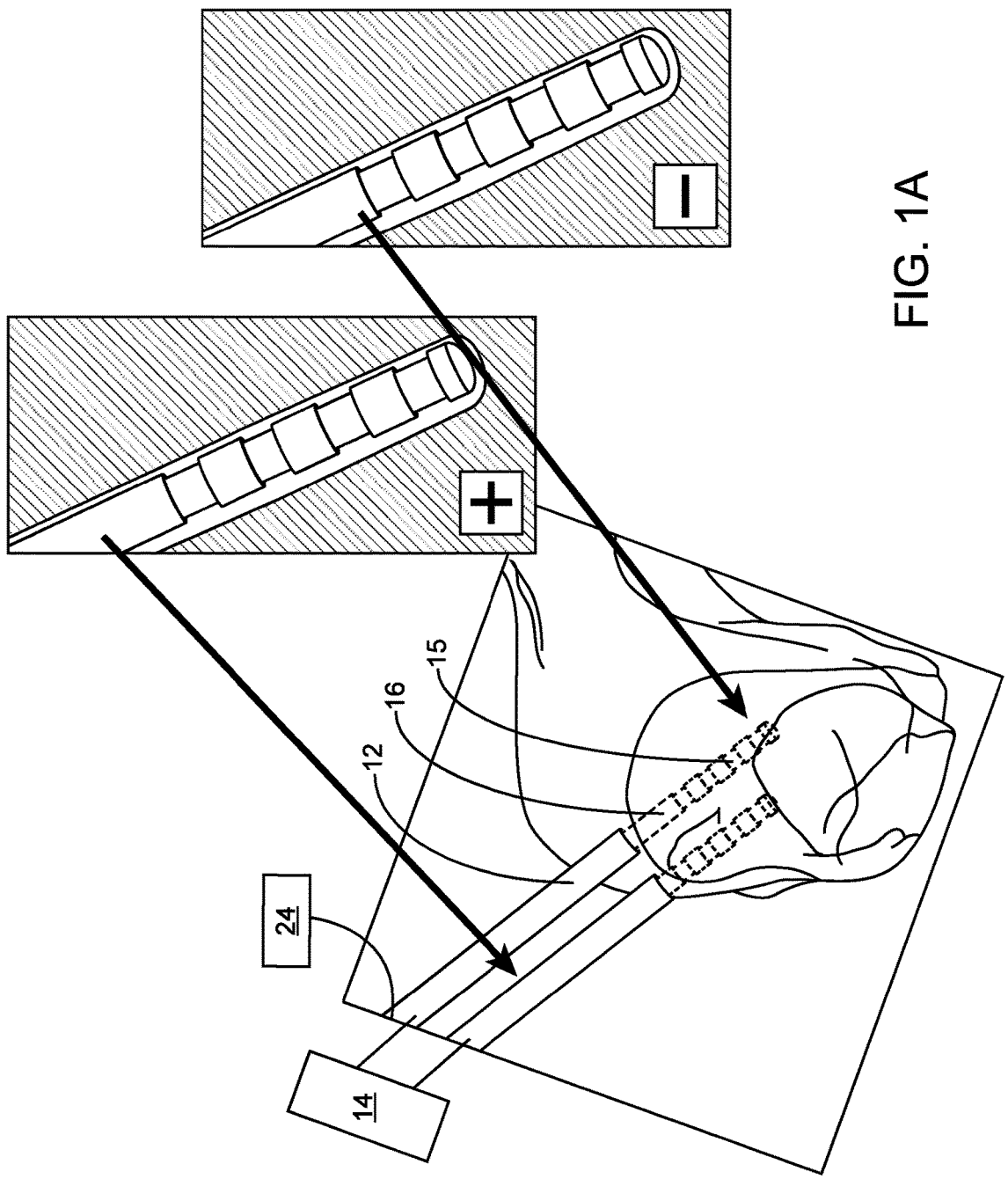
FIG. 1A is a partial side view and partial block diagram of one embodiment of a deep brain stimulation apparatus of the present invention.

The present invention relates to a systems and methods for multi-site activation of the thalamus. Methods, devices, and systems for achieving optimal control of intrathalamic dynamics and activation of anterior forebrain dynamics using multi-site deep brain stimulation ("mDBS") are disclosed herein. The anatomical connectivity and physiological specialization of the rostral and caudal intralaminar nuclei and their functional relationship with the thalamic reticular nucleus ("TRN"), cortex, and basal ganglia (striatum and pallidum) provide a framework to guide the placement of multiple stimulators within the thalamus and to organize patterns of stimulation to control intrathalamic and thalamocortical dynamics using the at least two stimulators. Specific patterns of activation of the rostral and caudal intralaminar nuclei have been identified to modulate activity in the TRN. The inter-electrode patterning of electrical stimulation of subcortical structures produces specific and consistent modulations of behavior.

DEFINITION OF TERMS

The term "electrode" as described herein is a conductor through which an electric current enters or leaves a substance, the electrical characteristics of which are being measured, used, or manipulated. Construction of electrodes used in deep brain stimulation is known in the art.

The term "sensor" as described herein is a device for measuring parameters in the brain, including current, voltage, oxygenation, neurochemicals, and other relevant parameters. A sensor may be an electrode. Sensors for measuring brain parameters are known in the art. One or more sensors may be incorporated in a detecting apparatus that may also comprise other elements including but not limited to processors, a power supply, and means for signal transmission, as are known in the art.

The term "shank" as described herein is a device upon which at least one electrode and/or sensor is anchored.

The term "stimulator" as described herein comprises at least one instance of a shank and one or more stimulating electrodes, or a BION system (which comprises electrodes). A stimulator may also comprise a sensor. If a stimulator comprises more than one electrode, it is commonly referred to in the art as a "multipolar electrode."

The term "central thalamus" as described herein is the region of the thalamus comprising the intralaminar nuclei.

The term "intralaminar nuclei" as described herein means the central lateral nucleus, paracentralis nucleus, central medial nucleus, Paraventricular nucleus, the midline thalamic nuclei, the centromedian-parafasicularis complex, and paralamellar regions, including the median dorsal nucleus, ventral anterior nucleus, ventral lateral nucleus, and inferior pulvinar nucleus. The intralaminar nuclei can be divided into an anterior (or rostral) group, and a posterior (or caudal) group. The anterior group includes the central lateral nucleus, paracentralis nucleus, central medial nucleus, Paraventricular nucleus, and midline thalamic nuclei. Paralaminar groups are anterior as defined herein. The posterior group includes the centromedian-parafasicularis complex. The posterior group contains the parafascicularis nucleus and the centromedian nucleus.

The term "thalamic projecting fibers" as described herein means a bundle of axons traveling within the thalamus and either originating in thalamus or projecting to the thalamus from other structures (e.g. brainstem, substantia nigra, or globus pallidus).

The term "orthodromic" as described herein refers to activation of an individual axon fiber or set of axon fibers in the direction of the physiological direction of action potential propagations (i.e. from cell body toward distal synapses).

The term "antidromic" as described herein refers to activation of an individual axon fiber or set of axon fibers in the direction opposite to the physiological direction of action potential propagations (i.e. from distal synapses toward cell body).

The term "controlling a thalamic projecting fiber" as described herein means applying a time-varying transmembrane voltage of sufficient strength to activate action potentials in a thalamic projecting fiber.

The term "controlling thalamocortical dynamics" as described herein means initiating a wave of activation in target structures receiving synaptic inputs from fibers activated within the thalamus, the wave having a desired spatiotemporal spread, frequency, and duration. The wave is capable of being detected by indirect methods of electroencephalographic recording or functional imaging techniques or direct measurement of activity within cortex.

The term "controlling thalamostriatal dynamics" as described herein means initiating a wave of activation in target structures receiving synaptic inputs from fibers activated within the thalamus, the wave having a desired spatiotemporal spread, frequency, and duration. The wave is capable of being detected by indirect methods of electroencephalographic recording or functional imaging techniques or direct measurement of activity within striatum.

The term "controlling intrathalamic dynamics" as described herein means initiating a wave of activation in target structures receiving synaptic inputs from fibers activated within the thalamus, the wave having a desired spatiotemporal spread, frequency, and duration. The wave is capable of being detected by indirect methods of electroencephalographic recording or functional imaging techniques or direct measurement of activity across thalamic relay nuclei.

Devices and Systems

Devices and systems for carrying out multi-site deep brain stimulation are described herein.

One aspect of the present invention relates to an apparatus for deep brain stimulation. The apparatus includes at least two stimulators comprising first and second stimulators. At least one stimulus signal generator is coupled to the first and second stimulators. The stimulus signal generator provides stimulus signals to the first and second stimulators causing current to pass between the first stimulator and the second stimulator.

FIGS. 1A-2B illustrate one embodiment of deep brain stimulation apparatus 10 of the present invention is illustrated. FIG. 1A is a perspective view and functional block diagram of deep brain stimulation apparatus 10. Deep brain stimulation apparatus 10 includes first and second stimulators 12 coupled to stimulus signal generator 14. Although deep brain stimulation apparatus 10 is described with respect to first and second stimulators 12, it is to be understood that deep brain stimulus apparatus 10 may include additional stimulators.

First and second stimulators 12 include at least one electrode 15 mounted on shank 16. In one embodiment, more than one electrode 15 is mounted on shank 16 such that stimulator 12 is a "multipolar electrode," with each electrode separately controllable. In this example, four electrodes 15 are located on each shank 16, although other numbers of electrodes may be utilized. Electrodes 15 are connected to one (or separate) insulated conductor(s) which passes through shank 16. The insulated conductor connects electrodes 15 to voltage control 24 and stimulus signal generator 14. Voltage control 24 and stimulus signal generator 14 may be separate from one another or part of a single unit. The connections mentioned herein may be wired or wireless.

Electrodes 15 are made from a conducting material, which may be an alloy such as platinum/iridium, with impedances known in the art, for example, between approximately of 100 and 150 kΩ. Electrodes 15 are approximately 0.5 mm in length. In one embodiment, where multiple electrodes 15 are mounted on shank 16, the separation between electrodes 15 may be variable or constant, and may be approximately 0.5 mm.

Shank 16 is configured to be implanted in the brain of the subject. Shank 16 may be configured as a cylinder, a square, a helix, or any other geometry known in the art as suitable for implementation. In one embodiment, shank 16 is implanted in the central thalamus of the subject.

Stimulus signal generator 14 produces a selected pulse train. In one embodiment, stimulus signal generator 14 is capable of separately driving individual electrodes 15 in a multi-electrode system through various channels. In this example, signal pulse generator may operatively select any one of electrodes 15 to provide a stimulus signal, or to provide a return signal. The signal pulse generator 14 may provide stimulation with various parameters, such as frequency or waveform, across multiple electrodes 15 simultaneously. Signal pulse generator 14 is capable of generating voltage wave trains of any desired form (sine, square wave, spike, rectangular, triangular, ramp, etc.) in a selectable voltage amplitude in the range from about 0.1 volts to about 10 volts and at selectable frequencies. In one embodiment, stimulus signal generator 14 is capable of generating constant current across at least one pair of electrodes 15 with either electrode in the pair assigned as a cathode or anode, although stimulus signal generator 14 may generate a constant current across two pairs of electrodes, across four pairs of electrodes, or across six pairs of electrodes, where either electrode in a pair can be assigned as a cathode or an anode. The compliance voltage of stimulus signal generator 14 is able to handle resistive loads across any pair of electrodes in the range from 0.5 kOhm to 10 kOhm. Each channel (cathode/anode pair) is able to deliver up 10 mA. Stimulus signal generator 14 includes circuitry that allows for monitoring of the current delivered across each channel. In one embodiment, stimulus signal generator 14 is programmable in that pulse shapes, sequences, and frequencies of pulses can be designed by software on a computer and uploaded to stimulus signal generator 14 for delivery to electrodes 15 upon command from a computer. The cathode-anode outputs from each channel may be used to provide bipolar constant-current stimulation in the intralaminar nuclei through any pair of electrode contacts across implanted stimulators 12.

Voltage control 24 provides a selected current amplitude or voltage to the waves of the pulse train. In practice, the pulse train and voltage amplitudes employed will be selected on a trial and error basis by evaluating a subject's response to various types and amplitudes of electrical stimulation over a time course of from about 1 to about 12 months. For example, after implanting stimulators 12 in the subject's thalamic nuclei, stimulation with a voltage within the range of from about 0.1 to about 10 volts or higher, a rate within the range of from about 50 to about 250 Hz, and a pulse width within the range of from about 50 to about 500 microseconds is applied for from about 8 to about 12 hours a day.

Figure 1B:
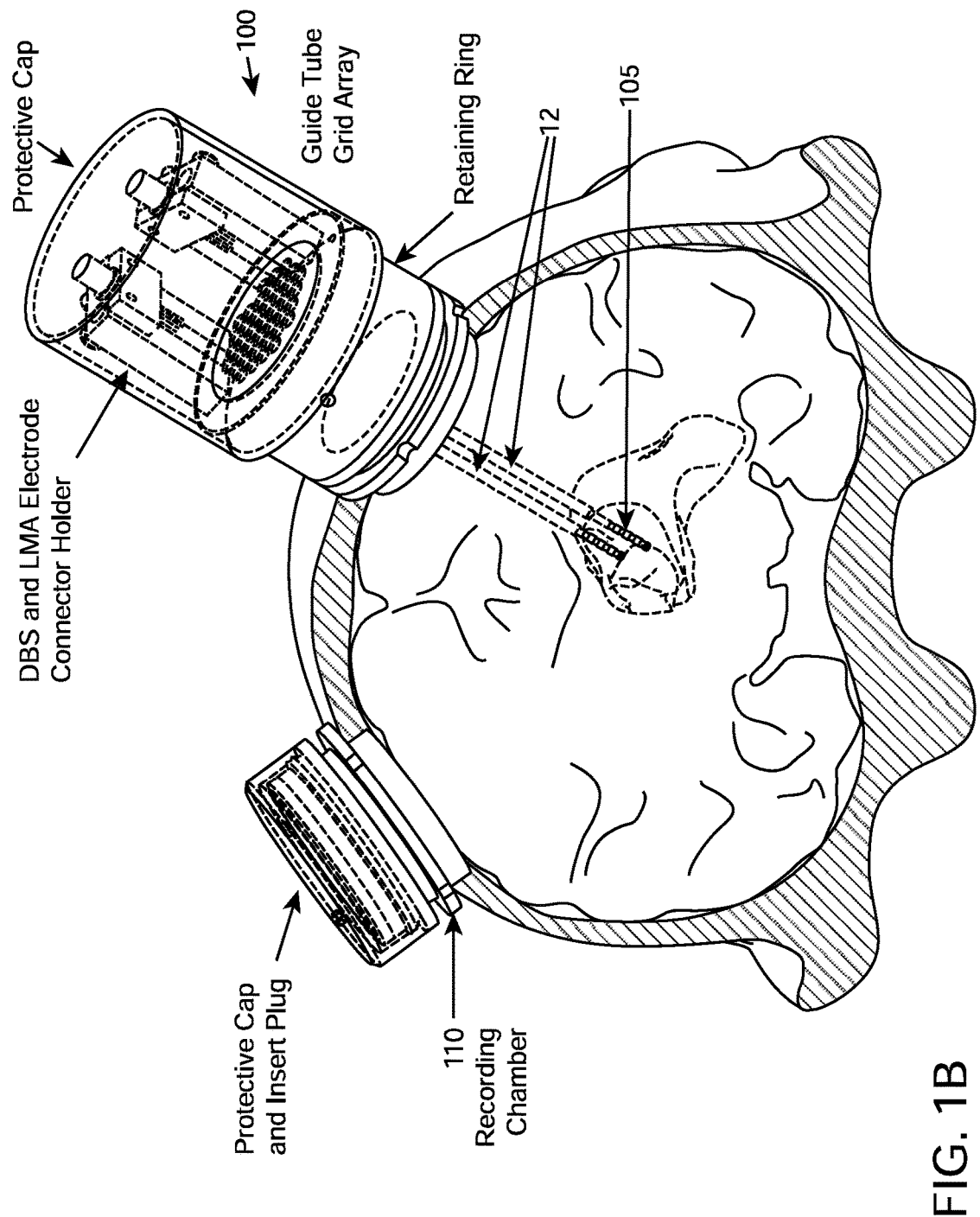
FIG. 1B is a perspective view of an experimental setup of a deep brain stimulation apparatus of the present invention.

FIG. 1B shows an experimental setup of deep brain stimulation apparatus 100 of the present invention, which was implanted in a macaque monkey. Deep brain stimulation apparatus 100 included stimulators 102 which are scaled-down versions of human DBS electrode-based stimulators (NuMED, Inc.). Stimulators 102 were placed in the central thalamus approximately 3 mm apart, one in the anterior intralaminar nuclei (hereinafter referenced as the rostral stimulator) and the other in the posterior intralaminar nuclei (hereinafter referenced as the caudal stimulator). Stimulators 102 included six platinum/iridium electrodes 105 with impedances of 100-150 kΩ. Each electrode 105 was 0.5 mm in length with a separation distance of 0.5 mm between electrodes 105. A computer-controlled external pulse generator (not shown) was used to drive individual electrodes 105. Deep brain stimulation apparatus 100 also included recording chamber 100 with a 32-microelectrode microdrive (Gray Matter Research), and a Deep Brain Stimulation and Recording System (DRBS) (not shown). Recording chamber 110 was placed over the frontal lobe of the monkey to allow for simultaneous multichannel single-unit and local field potential (LFP) recording from the frontal eye fields (FEF), the dorsal lateral prefrontal cortex (DLPF), and the dorsal striatum. The DBRS was implanted over the parietal lobe to allow for deep brain stimulation and local field potential recording in the central thalamus.

In one aspect of the present invention, the apparatus for deep brain stimulation further includes at least two sensors comprising first and second sensors. A state monitoring module is coupled to the first sensor. A performance monitoring module is coupled to the second sensor. A processing module is coupled to the state monitoring module and the performance monitoring module. The processing module receives state and performance levels. The processing module extracts a feature vector from the state and performance levels and computes a response stimulus signal based upon a comparison of the extracted feature vector to a prestored feature vector. The processing module also transmits the response stimulus to the stimulus signal generator.

Figure 2A:
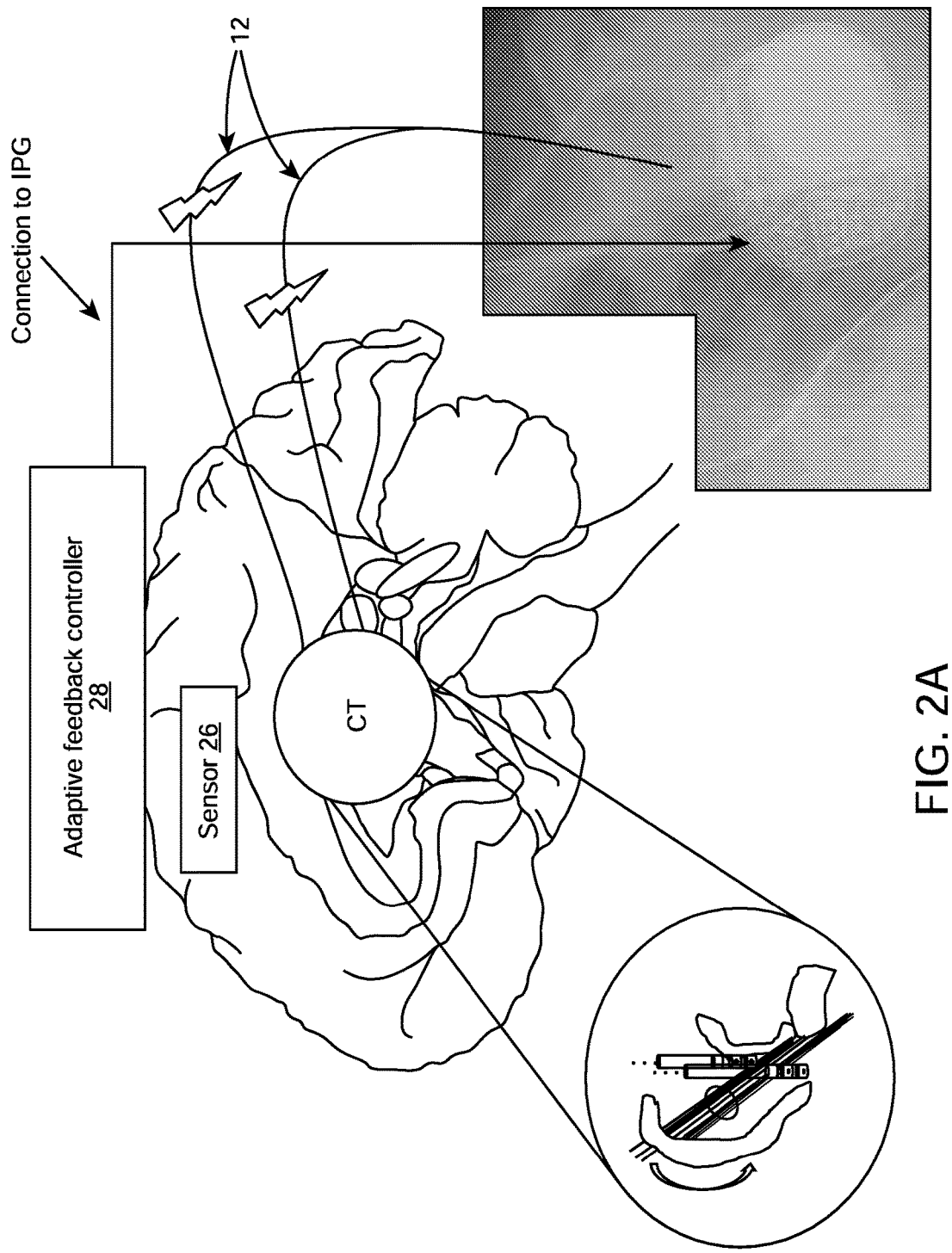
FIG. 2A is a partial side view and partial block diagram of one embodiment of a deep brain stimulation apparatus of the present invention implanted in a brain.
Figure 2B:
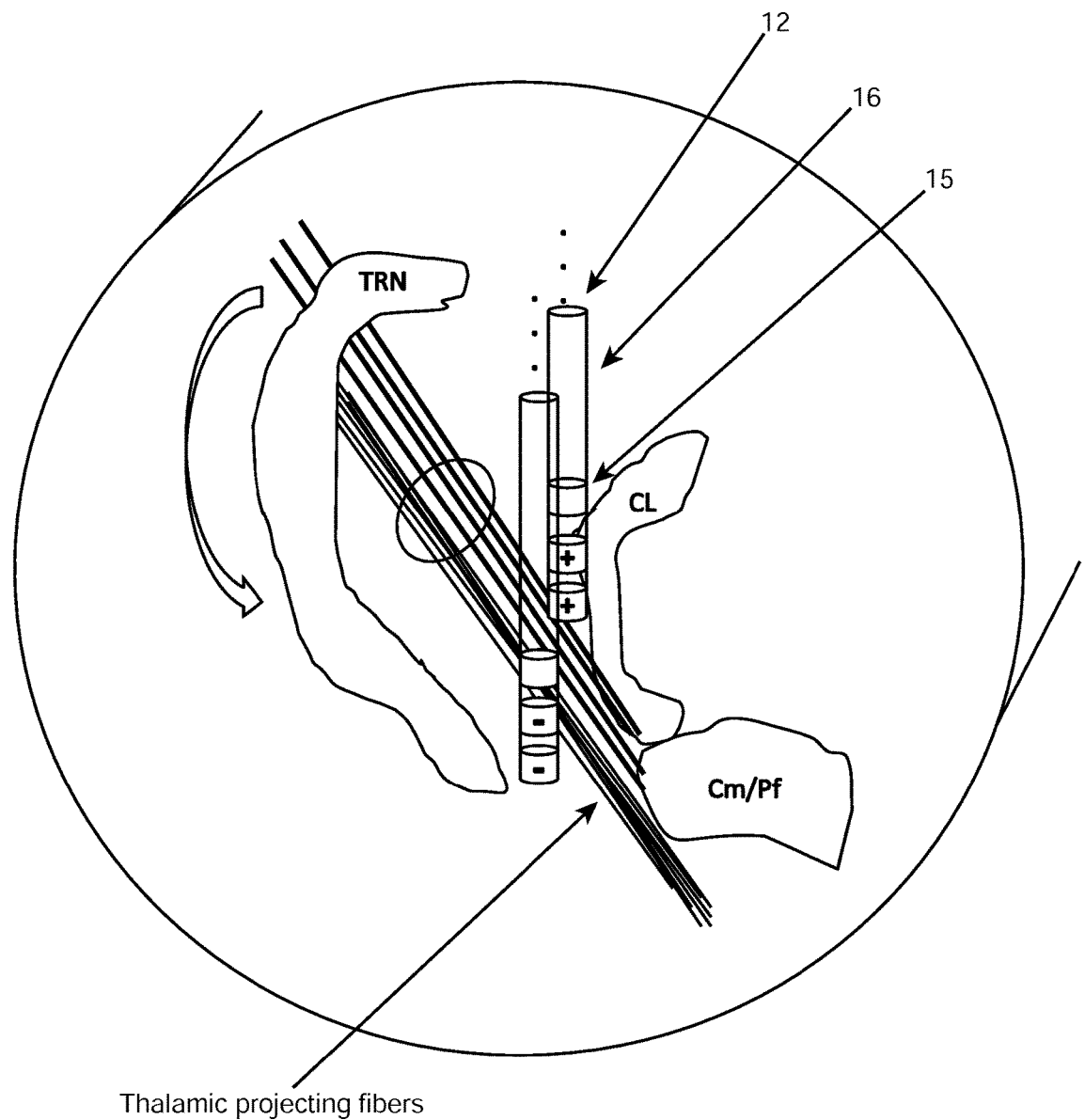
FIG. 2B is a magnified perspective view of a portion of the deep brain stimulation apparatus shown in FIG. 2A.

Referring now to FIGS. 2A-2B, in one embodiment, deep brain stimulation apparatus 10 includes one or more sensors 26 connected to adaptive feedback controller 28. Sensors 26 are configured to detect neuronal activity of one or more cortical and/or subcortical tissues of a selected subject's brain, by means known in the art, although electrodes 14 may be utilized to detect neuronal activity. In one embodiment, sensors 26 are incorporated into stimulators 12, although sensors 26 not incorporated into a stimulator, referred to herein as "extra-stimulator sensors" may be utilized. The extra-stimulator sensors may be implanted within cortical or subcortical regions or may be located on the scalp surface of the patient's head. Sensors 26 collect neuronal data in the form of, for example, single-unit activity, local field potentials, and/or electrocorticogram ("EcoG") activity. Connections between sensor 26 and brain tissue may be electrical, electromagnetic (wireless), or optical to one or many targets to be determined by availability and involvement in specific patterns of brain injury. In one embodiment, sensors 26 include computer and logic circuitry, although computer and logic circuitry associated with sensors 26 may be distributed among other components, such as incorporated into adaptive feedback controller 28, or in the stimulus signal generator 14, and/or one or more other devices, which may be implanted in the patient or external to the patient. In one embodiment, cortical placement of sensors 26 can detect the occurrence of failures of human control and adaptive feedback 28 controller can adjust stimulation of thalamic targets in synchronism with the processes occurring in deep brain stimulation apparatus 10 as described above.

Figure 3:
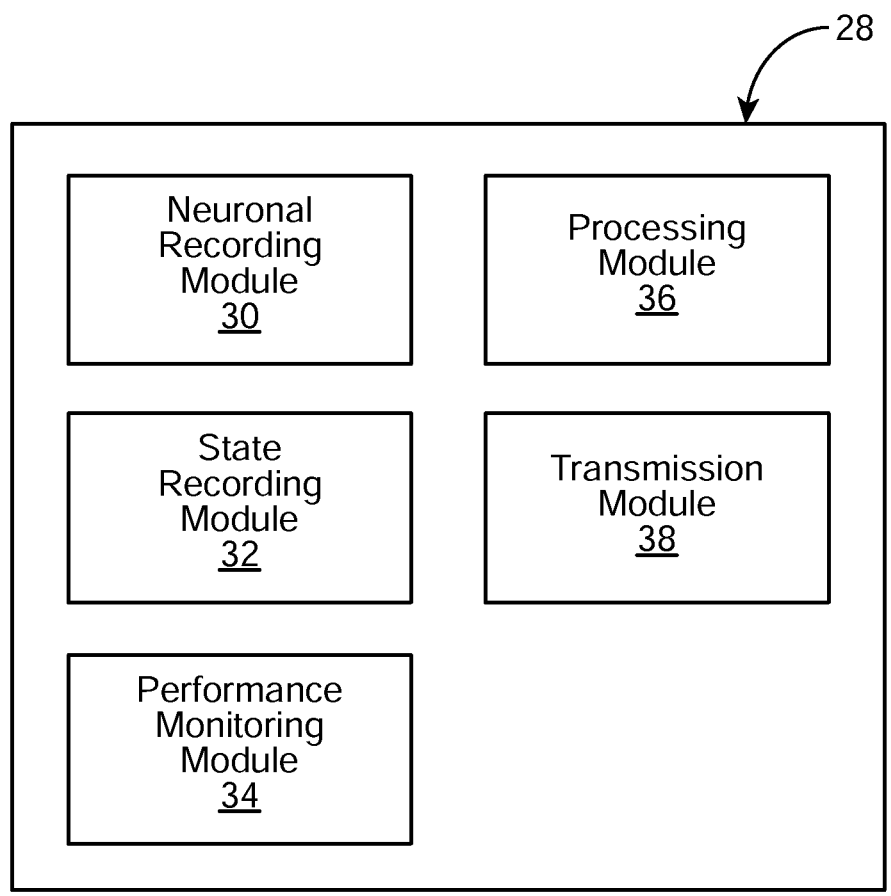
FIG. 3 is a block diagram of the adaptive feedback controller illustrated in FIG. 2A.

Referring now to FIG. 3, in one embodiment, adaptive feedback controller 28 includes neuronal recording module 30, state monitoring module 32, performance monitoring module 34, processing module 36, and transmission module 38. The modules described here for adaptive feedback controller 28 may be located within one physical device or may be distributed among multiple devices, and may be incorporated with other components or devices described herein. For example and without limitation, neuronal recording module 30 may be located in the same device as an extra-stimulator sensor and said device will have appropriate transmission pathways to receive and send information from and to other components of deep brain stimulation apparatus 10, the patient, and/or external systems used to maintain, control, or inspect deep brain stimulation apparatus 10 or the patient.

Neuronal recording module 30 receives and stores various items of information from sensors 26, such as electrical waveform pattern data unique to the patient. In one embodiment, neuronal recording module 30 stores information received from sensors 26 in real time when deep brain stimulation apparatus 10 is being used. In one embodiment, neuronal recording module 30 includes output means to allow retrieval of signals stored during an off-line operation of deep brain stimulation apparatus 10.

State monitoring module 32 is coupled to sensors 26, and is configured to store and process a first set of variables associated with a state of the detected neuronal activity, particularly the spectral content of the local neuronal activity and in particular, the total power within the frequency ranges 10-15 Hz, 15-20 Hz, 20-25 Hz, 25-30 Hz, 10-30 Hz which have all been empirically identified to increase within neuronal populations of the cortex, basal ganglia, and thalamus during either effective multi-site stimulation or during alert cognitive function. State monitoring module 32 may be used to sample the average characteristics of neuronal activity over time from sensors 26 or outside of the brain that collect neuronal signals for this purpose and to provide as feedback the real-time characteristics of the signals via direct or wireless (Bluetooth) connections. In one embodiment, state monitoring module 32 includes an internal memory and computational resources to extract signal features of the neuronal signal.

Performance monitoring module 34 is coupled to sensors 26 and is configured to store and process a second set of variables associated with modulation of the frequency of the locally detected neuronal activity. Performance monitoring module 34 is used to monitor the performance characteristics of the stimulation in producing increases in spectral power of local populations at pre-specified frequency ranges (e.g., 15-25 Hz). In one embodiment, performance monitoring module 34 includes an internal memory and computational resources to extract signal features of the neuronal signal.

Processing module 36 is coupled to state monitoring module 32 and performance monitoring module 34. In one embodiment, processing module 36 is configured to extract a feature vector based upon the processed first and second set of variables, and may be configured to compute an optimal response stimulus signal based upon a comparison between the extracted feature vector and a pre-stored feature vector corresponding to the local spectrum of neuronal activity for the subject recording sites.

Transmission module 38 is configured to transmit the optimal response stimulus signal computed by the processing module 36 to the implanted stimulus signal generator 14 to regulate the arousal level neuronal activity of the patient.

Based upon respective sets of variables stored and/or measured, performance monitoring module 34 and state monitoring module 32 may be used to extract a feature vector from the variables using computer and logic circuitry. Feature vectors represent an approximately complete mathematical description of electrical signals resulting from neuronal activity. Computed feature vectors can be used for further processing and to synthesize a feedback signal if necessary. A feedback signal can be outputted via a transmission path, which may be wired, wireless, or optical as known to one skilled in the art. The same or a separate component of deep brain stimulation apparatus 10 computes an output signal and transmits it to stimulator 12 placed within the brain, for example in intralaminar regions of the thalamus, to regulate their output in response to ongoing analysis provided by internal monitoring systems.

Referring again to FIGS. 2A and 2B, an embodiment of the present invention wherein the deep brain stimulation apparatus 10 includes sensors 26 that are interfaced to adaptive feedback controller 28, which in turn is interfaced to stimulus signal generator 14 is shown. Stimulus signal generator 14 is configured to provide feedback control of electrical stimulation of the targeted brain regions, for example without limitation, anterior and posterior intralaminar thalamic regions. Upon receipt of a signal via a transmission path, which may be wired, wireless, or optical, stimulus signal generator 14 provides a corresponding stimulus to these regions of the brain via at least one of stimulators 12 to modulate or maintain the arousal state of a subject. The operating characteristics of deep brain stimulation apparatus 10 may be adjusted automatically using adaptive feedback controller 28. In other embodiments, sensor 26 or components of adaptive feedback controller 28 may store information for retrieval by an external system or by a physician, or may be used by a physician/programmer to adjust deep brain stimulation apparatus 10 settings. Settings may be adjusted by the apparatus itself or by an external physician/programmer to raise a level of arousal, or impact on local signal power, or coupling of sensed structures (e.g. cortex and striatum) as measured, for example, using coherence.

Figure 4B:
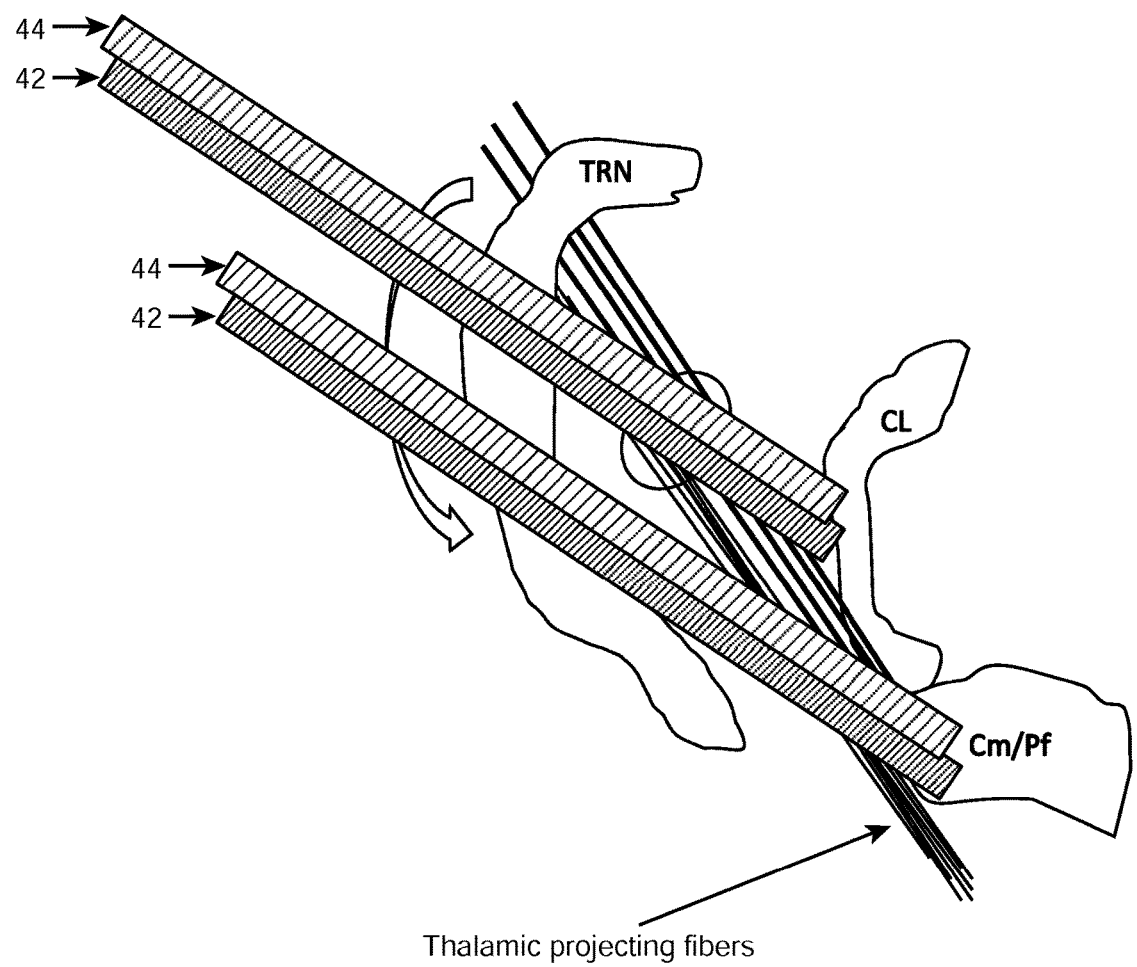
FIG. 4B is a magnified view of a portion of the deep brain stimulation apparatus shown in FIG. 4A.

FIGS. 4A and 4B illustrate an embodiment of the present invention where instead of stimulus signal generator 14, fiberoptic-optogenetic ("FOG") system 40 is coupled to sensors 26 and adaptive feedback controller 28 to track local power changes and cross-structure coherence patterns. In one embodiment, FOG system 40 can be configured to modulate activation of transfected cells within the brain such that a similar effect of co-activation across the nucleus reticularis is achieved and reflected in the activity recorded by implanted/surface sensors. As shown in FIG. 4B, FOG system 40 provides fiber optics 42 producing inactivation (e.g., a yellow light for hyperpolarizing currents produced by halorhodopsin channels) and fiber optics 44 producing activation (e.g., blue light for channel-rhodopsin inserted channels producing membrane depolarization), respectively. FOG system 40 controls the frequency and power of light sent through individual fiber-optics 42 and 44. Fibers may be changeably coupled to lasers in FOG system 40, or maybe permanently coupled, in which case multiple optical fibers may be targeted to the same cell populations in order to allow the frequency of illumination to be modulated. FOG system 40 includes one or more lasers, which may be fiber lasers, means to couple each laser to fiber optics 42 and 44, which means may be changeable. In one embodiment, FOG system 40 includes one or more optical elements to modulate frequency, power, or other qualities of illumination. In one embodiment, FOG system 40 includes controllers for lasers and changeable elements. FOG system 40 may be under feedback control by adaptive feedback controller 28.

Figure 5A:
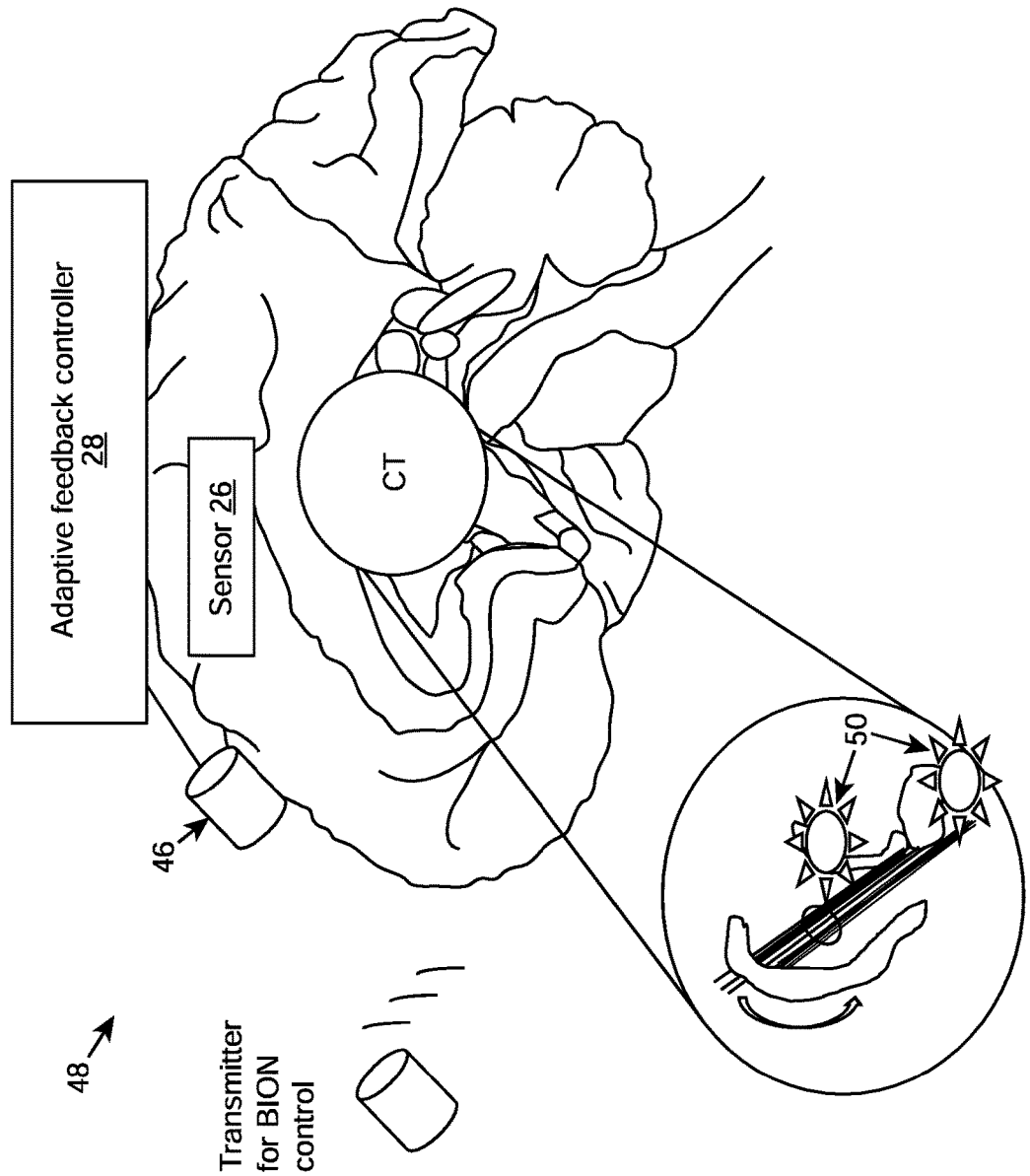
FIG. 5A is a partial side view and partial block diagram of a deep brain stimulation apparatus implanted in a brain utilizing a BION system.
Figure 5B:
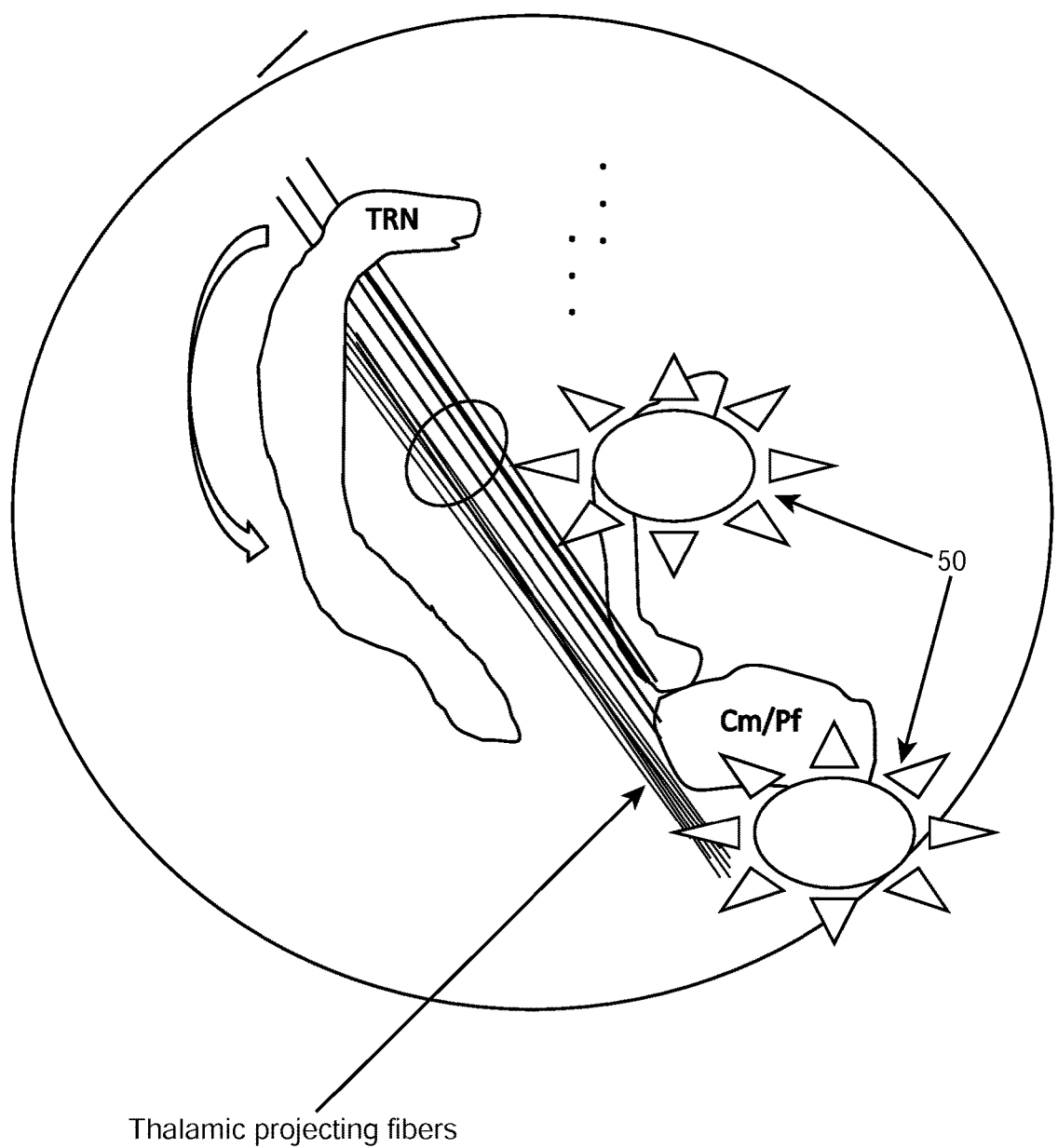
FIG. 5B is a magnified view of a portion of the deep brain stimulation apparatus shown in FIG. 5A.

FIGS. 5A and 5B illustrate another embodiment of the present invention where instead of stimulus signal generator 14, BION system 48 is coupled to sensors 26 and adaptive feedback controller 28 to track local power changes and cross-structure coherence patterns. BION system 48 includes BION transmitter 46 coupled to sensors 26. BION transmitter 46 connects through radiofrequency pulses to control implanted BIONs 50, which may be used to sense electro-optical properties depending on changes in neuronal activity. Alternatively, in one embodiment, BION transmitter 46 can be used to alter neuronal activity to maintain wakeful states of the subject.

Deep brain stimulation apparatus 10 is shown with specific stimulators 12, such as shank 16 with electrode 15, however, FOG system 40, BION system 48, or combinations thereof may be utilized, or a plurality of such systems and devices can be used depending upon specific requirements of a subject. It is also to be noted that although all the systems described include adaptive feedback controller 28 for a closed loop system, the present invention is not limited to closed loop systems.

A further aspect of the present invention is directed to a computer readable medium having stored thereon instructions for regulating various conditions in selected subjects. The computer readable medium comprises machine executable code which when executed by at least one processor, causes the processor to perform steps which may include detecting a level of neuronal activity in the selected subject's brain, and generating and sending a response stimulus signal to the subject's brain in response to the detected neuronal activity level under conditions effective to regulate the various conditions of the subject. The regulation of various conditions includes, but is not limited to, regulating arousal level, suppressing seizures, and normalizing movement of the subject. Such a computing system and computer readable medium is described in more detail in FIG. 6A.

Figure 6B:
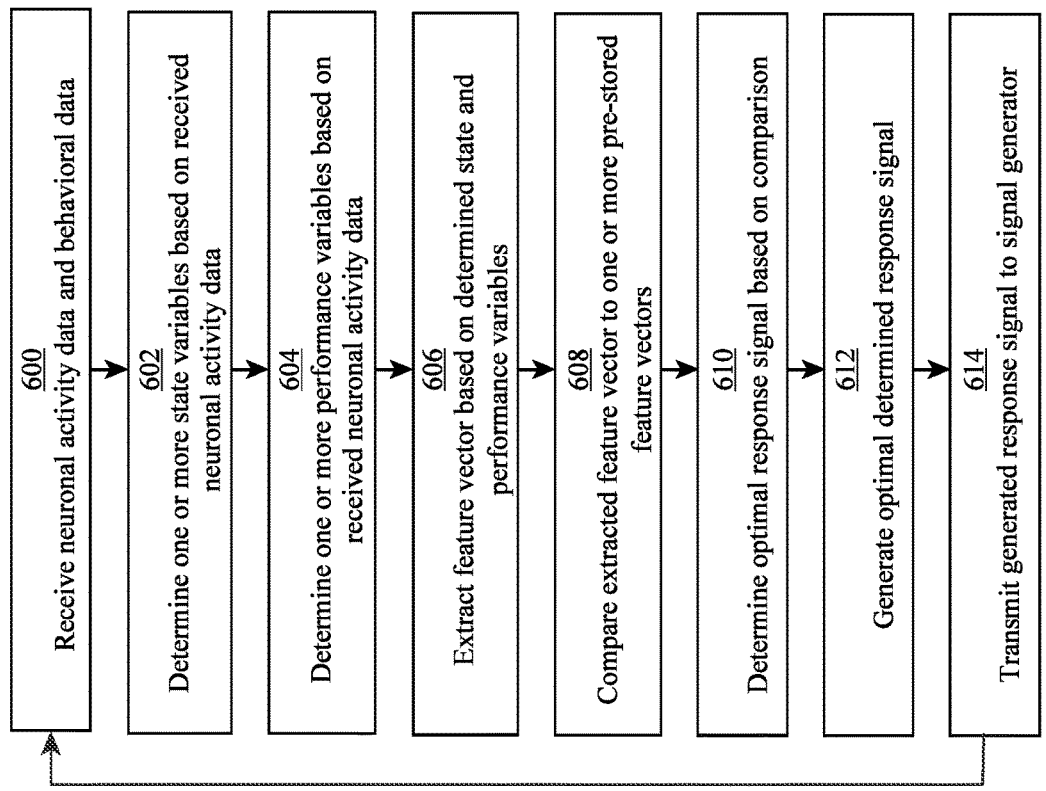
FIG. 6B is a flowchart of an exemplary method that may be performed by the CPU illustrated in FIG. 6A.
Figure 6A:
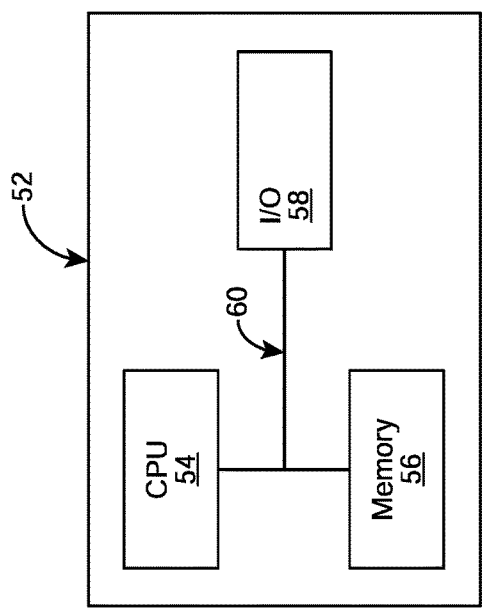
FIG. 6A is a block diagram of a CPU which may be connected to the deep brain stimulation apparatus illustrated in FIGS. 2A, 4A, and 5A.

The present invention includes computing system 52 as shown in FIG. 6A. In one embodiment, computing system 52 is part of the computer and logic circuitry of the deep brain stimulation apparatus 10, although computing system 52 may be separate from the deep brain stimulation apparatus 10. Computing system 52 includes a central processing unit ("CPU") or processor 54, memory 56, and input-output port 58, which are coupled together by bus 60 or other link.

Processor 54 executes a computer program or code comprising stored instructions for one or more aspects of the present invention, as described and illustrated herein. In addition, processor 54 may execute other programmed instructions. In one embodiment, processor 54 is configured to process the detected level of neuronal activity in the selected subject's brain, communicate via input-output port 58 the processed neuronal activity data to an I/O interface of stimulators 12 coupled to the subject's brain, and instruct stimulators 12 to generate and send a response stimulus signal to the subject's brain in response to the detected neuronal activity level under conditions effective to regulate the arousal level of the subject. Processor 54 retrieves information from memory 56 that stores information about a subject's optimal neuronal activity parameters. According to one embodiment of the present invention, memory 56 can store a neuronal firing rate threshold corresponding to an arousal level of a subject, waveform patterns corresponding to different regions of the brain during arousal, in addition to real time data about neuronal activity detected by sensors 26 of deep brain stimulation apparatus 10. The processor 54 executes computer code that carries out the steps of determining an optimal stimulation intensity of the response stimulus signal to be sent by deep brain stimulation apparatus 10 device via transmission module 38. Processor 54 can be programmed to transfer computed data regarding a subject's neuronal activity to an external server (not shown) too.

Memory 56 stores the programmed instructions written in a computer programming language or software package for carrying out one or more aspects of the present invention as described and illustrated herein. However, some or all of the programmed instructions could be stored and/or executed elsewhere. For example, instructions for executing the above-noted steps can be stored in a distributed storage environment where memory 56 is shared between one or more computing systems similar to computing system 50. For example, memory 56 stores a sample of the local power spectrum of each sensor 26 as shown in FIG. 2A and, upon execution of instructions by processor 54, provides pre-stored values for adjusting the response stimulus signal to be sent to the subject's brain via deep brain stimulation apparatus 10 when a predefined difference between sample and reference values is detected. A variety of different types of memory storage devices, such as a random access memory (RAM) or a read only memory (ROM) in the system or a floppy disk, hard disk, CD ROM, or other computer readable medium which is read from and/or written to by a magnetic, optical, or other reading and/or writing system that is coupled to one or more processors, can be used for memory 56.

Input-output port 58 is used to operatively couple and communicate between computing system 52, and other parts of deep brain stimulation apparatus 10, although other types and numbers of connections and configurations to other types and numbers of systems, devices, and components can be used. For example, input-output port 58 can be programmed to a display or an external device prior to deep brain stimulation apparatus 10 sending the response stimulus signal if the detected neuronal activity matches a neuronal activity parameter. Alternatively, using input-output port 58, processor 54 can repetitively send additional response stimulus signals to drive stimulation of subject's brain until a particular neuronal activity parameter, stored on computer readable memory 56, is met.

Alternatively, processor 54 may be caused to send a response stimulus signal when the detected level of neuronal activity does not match with a predefined waveform pattern stored in memory 56. For sending instructions to various components of deep brain stimulation apparatus 10, processor 54 communicates via input-output port 58. Processor 54 can include an embedded codec (not shown) to encode and decode the detected neuronal activity onto a binary data stream representation of the detected neuronal activity. Further, in one embodiment, processor 54 executes instructions to carry out operations on the detected neuronal activity data with one or more of an electrical, a fiber optic, or a bionic neuron communication channel interfaced with processor 54.

In an another embodiment, processor 54 may be caused to receive a continuous time voltage representation signal to deep brain stimulation apparatus 10 generated as an output of an electroencephalograph ("EEG") in response to the detected neuronal activity. Processor 54 also may perform computations related to a spectral analysis of the detected neuronal activity for identifying one or more frequencies associated with the neuronal activity, and may modify the response stimulus signal based upon the identified one or more frequencies. As a result, processor 54 is used by deep brain stimulation apparatus 10 to regulate arousal levels and for feedback controlling stimulation of arousal systems of the brain.

Furthermore, processor 54 may be configured to process data associated with monitoring of performance and state of deep brain stimulation apparatus 10 device by collecting neuronal data associated with the detected neuronal activity in the form of one or more of a single-unit neuron activity, local field potentials, or electrocorticogram activity and extracting signal features from the detected neuronal activity to aid performance monitoring module 34 and state monitoring module 32 to form and store in memory 56 one or more feature vectors, in addition to one or more pre-stored feature vectors, suitable for computer analysis. In one embodiment, computing system 52 is configured to perform the method steps shown in the flowchart in FIG. 6B.

Referring now to FIGS. 6A and 6B, a flowchart of an exemplary method performed by computing system 54 is illustrated. In step 600, computing system 52 receives neuronal activity data and behavioral data. In one embodiment, the received neuronal activity data and The neuronal activity data and behavioral data are received through I/O 58 via sensors 26, which are illustrated in FIG. 2A. Referring again to FIGS. 6A and 6B, in step 602 computing system 52 determines one or more state variables based on the received neuronal activity data. Next, in step 604, computing system 52 determines one or more performance variables based on the received neuronal activity data. In step 606 computing system extracts feature vectors based on the determined state and performance variables. Next, in step 608 computing system 52 compares the extracted feature vectors to one or more pre-stored feature vectors which are stored in memory 56 of computing system 52. In step 610 computing system 52 determines an optimal response signal based on the comparison done in step 608. Next, in step 612 the computing system 52 generates the determined optimal response signal and transmits the generated response signal to a signal generator in step 614.

Although embodiments of the computing system are described and illustrated herein as completely residing within deep brain stimulation apparatus 10, computing system 52 can be implemented on any suitable computing system or computing device. It is to be understood that the devices and systems described herein are for exemplary purposes and many variations of the specific hardware and software are possible, as will be appreciated by those skilled in the relevant art(s).

Alternatively, each of the systems may be conveniently implemented using one or more general purpose computer systems, microprocessors, digital signal processors, and micro-controllers, programmed according to the teachings described and illustrated herein. For example, the processor can be an Intel Core Duo® processor provided by Intel Corporation of Santa Clara, Calif.

In addition, two or more computing systems or devices can be substituted for any one of the systems described above. Accordingly, principles and advantages of distributed processing, such as redundancy and replication, also can be implemented, as desired, to increase the robustness and performance of the devices and systems described above. The embodiments of the present invention may also be implemented on a computer system or systems that extend across any suitable network using any suitable interface mechanisms and communications technologies, including, by way of example only, telecommunications in any suitable form (e.g., voice and modem), wireless communications media, wireless communications networks, cellular communications networks, G3 communications networks, Public Switched Telephone Networks (PSTNs), Packet Data Networks (PDNs), the Internet, intranets, and combinations thereof.

The present invention can utilize a computer readable medium having instructions stored thereon for one or more aspects of the present invention as described and illustrated by way of the embodiments herein. When executed by a processor, these instructions cause the processor to carry out the steps necessary to implement the methods of the present invention.

Methods of Treatment

One aspect of the present invention relates to a method to control a thalamic projecting fiber in a subject. This method involves providing a subject having a first stimulator and a second stimulator implanted in the subject's central thalamus. A stimulus signal generator is provided which is coupled to the first and second stimulators. Separate stimulus signals are provided from the stimulus signal generator to the first and second stimulators under conditions effective to control the thalamic projecting fiber in the subject. This aspect of the present invention may be preceded by an actual step of implanting the first and second stimulators in the subject's central thalamus.

Figure 7:
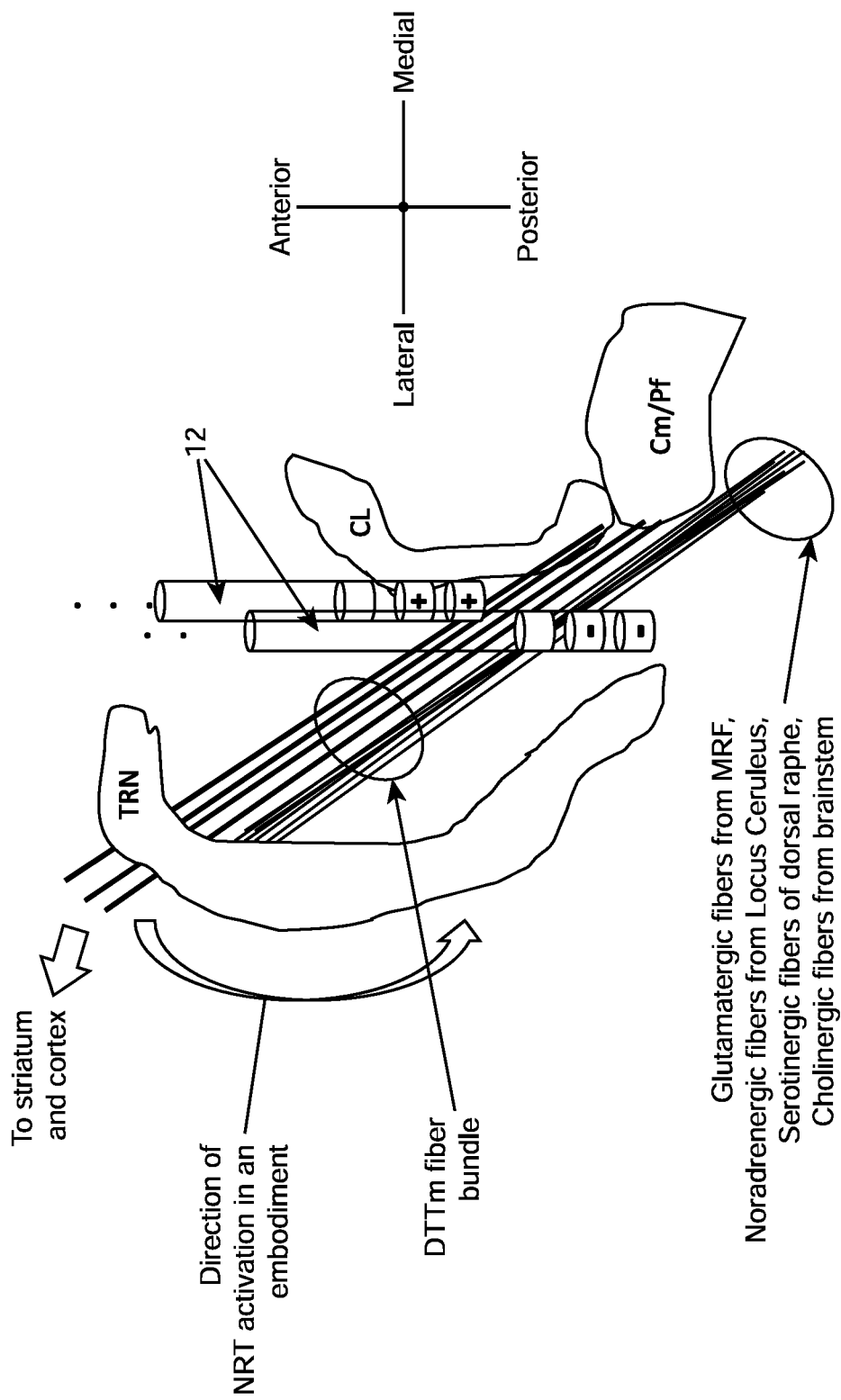
FIG. 7 is a perspective view of an example of the placement of stimulators of the deep brain stimulation apparatus for multi-stimulation of the thalamus according to one embodiment of the present invention.

In one embodiment, once a relevant subject is selected, first and second stimulators 12, as described above, are implanted in the subject's central thalamus as illustrated in FIG. 7. In one embodiment, stimulators 12 are introduced via burr holes in the skull. The burr holes are placed based on the particular region of the intralaminar nuclei to be contacted. Generally, prior to the introduction of stimulators 12, a detailed mapping with microelectrode and microstimulation following standard methods is carried out as described in Tasker et al., "The Role of the Thalamus in Functional Neurosurgery," *Neurosurgery Clinics of North America* 6(1):73-104 (1995), which is incorporated herein by reference in its entirety. Briefly, for each subdivision of the intralaminar nuclei, a preferred trajectory of approach optimizing the safety of entry point and maximal number of identifiable physiological landmarks in the responses of cell groups encountered along the trajectory into the desired region or regions of the intralaminar nuclei can be identified by one skilled in the art. This can be done, for example, by following the methods and catalogued physiological responses of different human thalamic cell groups described in Tasker et al., "The Role of the Thalamus in Functional Neurosurgery," *Neurosurgery Clinics of North America* 6(1):73-104 (1995), which is incorporated herein by reference in its entirety. Initial mapping of the path for the stimulators can, therefore, be carried out via a combination of detailed single-unit recording of receptive field ("RF") properties of the cells encountered along the trajectory, projective fields ("PF") mapped by microstimulation of the same cell groups, and comparison with known RF and PF responses in the human thalamus. Similarly, evoked potentials can be elicited from microstimulation electrodes and, for the intralaminar nuclei, have several characteristic signatures identifiable from scalp surface recording as discussed in Velasco, et al. "Foramen Ovale Electrodes Can Identify a Focal Seizure Onset When Surface EEG Fails in Mesial Temporal Lobe Epilepsy," *Epilepsia* 47(8):1300-7

(2006) and Tasker et al., "Computer Mapping of Brainstem Sensory Centres in Man," *J. Neurosurg.* 44:458-464 (1976), which are incorporated herein by reference in their entirety. For this mapping, microstimulation, using tungsten microelectrodes with impedances of roughly 1.5 megaohms, every 1 mm at threshold of up to 100 microamperes with short trains of 300 Hz pulses of 0.2 millisecond pulse width may be employed as described in Tasker et al., "Computer Mapping of Brainstem Sensory Centres in Man," *J. Neurosurg.* 44:458-464 (1976), which is incorporated herein by reference in its entirety. Typically, an on-line data base of RF and PF information along the trajectory and stereotactic coordinates derived, for example, from Schaltenbrand et al., "Introduction to Stereotaxis with an Atlas of the Human Brain," *Stuttgart:Thieme* (1977) and Tasker et al., "Computer Mapping of Brainstem Sensory Centres in Man," *J. Neurosurg.* 44:458-464 (1976), which are hereby incorporated by reference in their entirety, or by computed mapping techniques, such as those described in Tasker et al., "Computer Mapping of Brainstem Sensory Centres in Man," *J. Neurosurg.* 44:458-464 (1976), which is incorporated herein by reference in its entirety, can be used, either with or without a magnetic resonance imaging ("MRI")-based stereotactic apparatus. See Schaltenbrand et al., "Introduction to Stereotaxis with an Atlas of the Human Brain," *Stuttgart: Thieme* (1977), which is incorporated herein by reference in its entirety.

To carry out the above methods, a subject may be conscious with application of local anesthesia or mild sedation. In cases where a subject is not sufficiently cooperative to remain conscious during the procedure, the above-described approach can be modified in ways known in the art, to allow the operation to be completed under general anesthesia.

Subjects may include any animal, including a human. Non-human animals includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses. The subject may also be livestock such as, cattle, swine, sheep, poultry, and horses, or pets, such as dogs and cats.

The methods of the invention described herein can be employed for subjects of any species, gender, age, ethnic population, or genotype. Accordingly, the term subject includes males and females, and it includes elderly, adult-to-elderly transition age subjects adults, pre-adult-to-adult transition age subjects, and pre-adults, including adolescents, children, and infants. In one embodiment, subjects are adult subjects in their twenties to forties, who have the most to gain from treatment and represent the greatest cost to society if left untreated. Examples of human ethnic populations include Caucasians, Asians, Hispanics, Africans, African Americans, Native Americans, Semites, and Pacific Islanders. The term subject also includes subjects of any genotype or phenotype as long as they are in need of the invention, as described herein. In addition, the subject can have the genotype or phenotype for any hair color, eye color, skin color or any combination thereof. The term subject includes a subject of any body height, body weight, or any organ or body part size or shape.

Because subjects with higher levels of functional recovery maintain greater connectivity of neuronal populations and numbers of living neurons, those subjects who remain chronically near functional boundaries that would allow significant changes in independence, social reintegration, or vocational reentry would be the preferred group to benefit from the technologies described herein. For example, subjects unable to qualify for cognitive rehabilitation programs because of a lack of sufficient capacity to hold and maintain cognitive tasks over time would benefit from the technology described herein. The treatment approach described here would be expected to support recruitment of many under-active neurons across frontal/prefrontal cortex to aid in the transition to readiness for and completion of cognitive retraining programs.

Although the method is not limited to one set of fibers and their orientation, an optimal target for the application of two or more stimulators 12 within the central thalamus to control white matter fibers is suggested as shown in FIG. 7. Stimulator 12 placement spans the borders of the central lateral ("CL") and centromedian ("Cm/Pf") nuclei which are known to project to the thalamic reticular nucleus ("TRN") and control inhibition of different thalamic compartments. See Crabtree et al., "New Intrathalamic Pathways Allowing Modality-Related and Cross-Modality Switching in the Dorsal Thalamus" *J. Neurosci.* 22(19):8754-61 (2002), which is incorporated herein by reference in its entirety.

In one embodiment, the brain regions that are stimulated include intralaminar nuclei, specifically the centromedian and parafascicular nuclei, and the disease or condition that is treated is impaired cognitive function.

Stimulators 12 can be placed such that at least one electrode 15 is in contact with a desired region of a subject's brain, including but not limited to the central thalamus, striatopallidal structure, basal forebrain, and brainstem, by the methods conventionally employed for embedding or emplacing stimulators for deep brain stimulation in other brain regions, such as thalamic nuclei. In principle, other pathways could be targeted to control activation of the thalamic reticular nucleus ("TRN") including other subcortical or cortical structures with strong projections to the TRN, preferentially the subset projecting to the rostral pole of the structure (e.g. pallidoreticular fibers, nigroreticular fibers, among other pathways). Such methods are described in Tasker et al., "The Role of the Thalamus in Functional Neurosurgery," *Neurosurgery Clinics of North America* 6(1):73-104 (1995), which is incorporated herein by reference in its entirety.

At the point of closest apposition of fibers exiting CL and Pf that connect to TRN, a recently described fiber pathway from the human brainstem to the central thalamus, the medial dorsal tegmental tract ("DTTm") carries brainstem glutamatergic (from mesencephalic reticular formation), serotinergic (from dorsal raphe), noradrenergic (from locus ceruleus), and cholinergic fibers (from brainstem cholinergic populations) to the TRN. See Edlow et al., "Neuroanatomic Connectivity of the Human Ascending Arousal System Critical to Consciousness and Its Disorders," *J. Neuropathol. Exp. Neurol.* 71(6):531-46 (2012), which is incorporated by reference herein in its entirety. Orientation of two or more stimulators 12 to allow control of fibers within this local region within the central thalamus would thus provide an optimal system for enabling the present invention. In one embodiment, configuration of the anode and cathode placements to achieve activation of the rostral pole of the TRN prior to activation of other parts of the structure to allow a traveling wave in a rostro-caudal direction is preferred. This is the natural direction of wave activity in this structure and under one theory of the present invention optimal behavioral facilitation is expected when rostrocaudal patterns of sequential activation are generated in the TRN.

Identification of the location of this confluence of fiber pathways can be optimally achieved with the use of diffusion tensor imaging according to available published methods such as, Edlow et al., "Neuroanatomic Connectivity of the Human Ascending Arousal System Critical to Consciousness and Its Disorders," *J. Neuropathol. Exp. Neurol.* 71(6): 531-46 (2012), which is incorporated herein by reference in its entirety.

Figure 8:
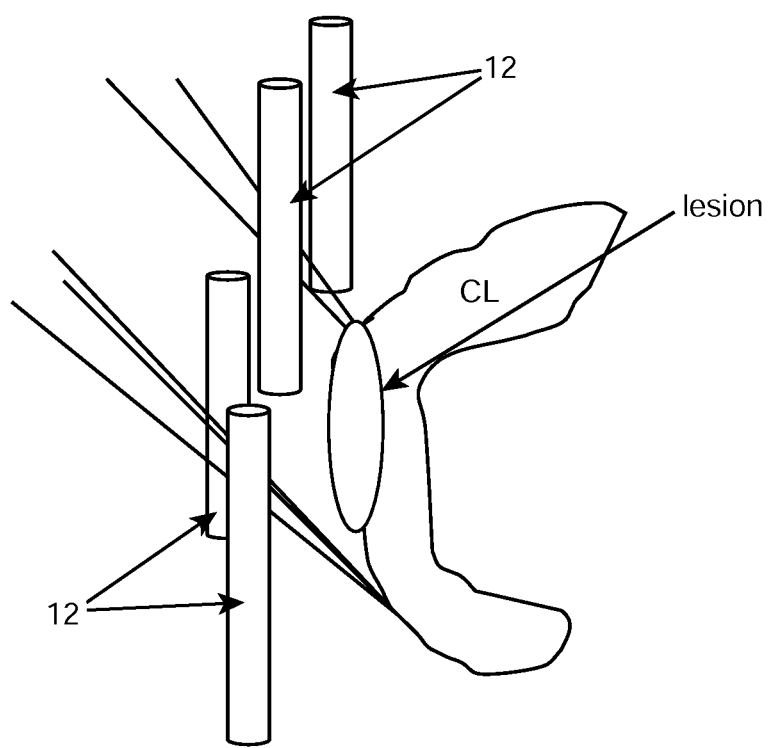
FIG. 8 is a perspective view of the placement of stimulators of the deep brain stimulation apparatus for multi-stimulation of the thalamus according to another embodiment of the present invention.

In one embodiment of the present invention, the location of this confluence of fiber bundles is determined by the location where the lowest voltage threshold for eliciting a response in a human subject with central thalamic electrodes stimulated in monopolar mode is found. The use of multiple (two or more stimulators 12) provides a method to optimally angle and control this fiber bundle in intact systems and in lesioned systems where more than two stimulators or adjuvant stimulation systems may be required to achieve optimal control of the brain dynamics as illustrated in FIG. 8.

Stimulation is applied between stimulators 12, as described above, by a stimulus signal generator under conditions effective to control thalamic projecting fibers in the subject. In one embodiment, stimulation is provided to at least a portion of the patient's intralaminar nuclei.

Figure 9:
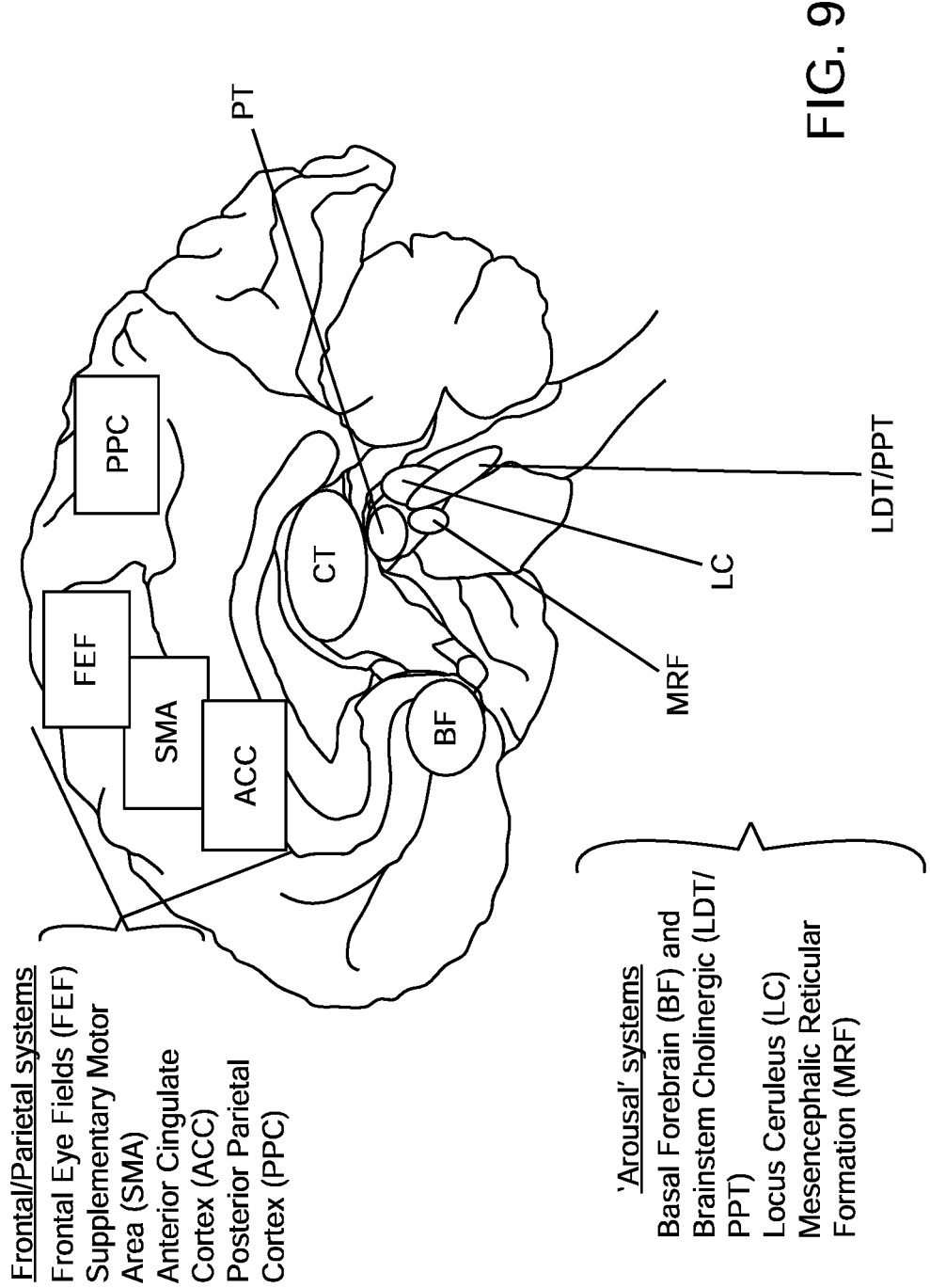
FIG. 9 is a schematic view of the convergence of arousal system afferents in the central thalamus and efferent projections to the anterior forebrain linked to arousal regulation.

Intralaminar nuclei are a small set of nuclei located in the paramedian thalamus. The intralaminar nuclei can be divided into an anterior group and a posterior group. FIG. 9 illustrates the anatomical connections of the intralaminar nuclei with distributed circuits underlying arousal, attention, intention, working memory, and gaze and motor control. The anterior group projects widely throughout the neocortex to primary sensory and motor areas and associated cortices, while the posterior group projects mainly to sensory-motor and premotor areas and striatal targets. The anterior IL group includes the central lateral nucleus ("CL"), which projects to the frontal eye field ("FEF"), motor cortex, and, more heavily, to the posterior parietal cortex ("PPC"). The paracentralis ("Pc") nucleus projects to the prefrontal cortex (with heavier projection than CL) and very strongly to the inferior parietal lobe and visual association cortices. The central medial ("CeM") nucleus, which projects to the prefrontal and visual association cortices, also projects to the cingulate cortex and pregenual areas and to the medial cortical surface and orbitofrontal cortex. Included within the meaning of intralaminar nuclei, as used herein, is the paraventricular nucleus ("Pv"), which is strongly associated with the limbic system, and midline thalamic nuclei. Projections to prefrontal cortex ("PFC") and anterior cingulate cortex arise, as well, from the anterior intralaminar group. The CL is also known to project to the primary visual cortex in the cat and monkey. The posterior group is dominated by the centromedian-parafasicularis complex ("Cm-Pf"). In primates, the Cm-Pf undergoes a notable expansion, and the CL also expands and develops further subdivisions. This system projects strongly to the caudate (from Pt), putamen (from Cm nuclei of the basal ganglia), and prefrontal and parietal association cortices. A small projection (Pf) also goes to the FEF. The intralaminar nuclei projections to the striatum per se are considered the principle efferent connections of the intralaminar nuclei and include anterior group projections to the caudate, as well. Thus, the intralaminar nuclei (including the midline nuclei) are targeted to modulate the large thalamo-cortical-basal ganglia loops, especially to synchronize their function as discussed, for example, in Groenewegen et al., "The Specificity of the 'Nonspecific" Midline and Intralaminar Thalamic Nuclei," *Trends in Neuroscience* 17:52-66 (1994), which is incorporated herein by reference in its entirety.

The intralaminar nuclei receive ascending inputs from several components of the ascending reticular arousal system, including the pedunculopontine cholinergic group (lateral dorsal tegmentum), mesencephalic reticular formation, locus ceruleus, and dorsal raphe. Thus, the intralaminar nuclei are targets of modulation by a wide variety of neurotransmitter agents, including acetylcholine (pedunculopontine, lateral dorsal tegmentum, and mesencephalic reticular formation neurons), noradrenaline (locus ceruleus) serotonin (raphe nuclei), and histamine (hypothalamus). Also received by the intralaminar nuclei are nociceptive, cerebellar, tectal, pretectal, and rhinencephalic inputs. Descending inputs reciprocally relate components of the intralaminar nuclei with their cortical projections.

Although each cell group within the intralaminar nuclei projects to many separate cortical targets, each neuron of the intralaminar nuclei has a narrowly elaborated projection and receives its cortical feedback from the same restricted area. The reciprocal projections between the intralaminar nuclei and cortex have a distinctive laminar pattern that differs from the more well-known pattern of the reciprocal projections of the relay nuclei. The intralaminar nuclei neurons synapse in Layer I on the terminal dendritic tufts of layers III and V pyramidal cells and in layers V and VI, whereas neurons of the relay nuclei terminate primarily in cortical layers III and IV. Feedback to intralaminar nuclei neurons originates in Layer V, but feedback to the relay nuclei originates in Layer VI. In cats, the dominant corticothalamic input to the CL originates in the PFC, whereas the visual areas, including area 17, also project directly to the CL.

Intralaminar projections to the striatum are an essential aspect of the activation mechanism of brain stimulation in these regions and projections to the striatum may be diffuse in their arborization (such as from CL) or more locally restricted (as in the case of the centromedian nucleus).

A known specialization of the CL fiber projections is the presence of populations of neurons with differing conduction times to striatal and cortical targets (See Glenn et al., "Discharge Rate and Excitability of Cortically Projecting Intralaminar Thalamic Neurons During Waking and Sleep States," *J Neurosci,* 2: 1287-1404 (1982) and Steriade et al., "Neocortical and Caudate Projections of Intralaminar Thalamic Neurons and their Synaptic Excitation From Midbrain Reticular Core," *J Neurophysiol.,* 48, 352-71 (1982), which are hereby incorporated by reference herein in their entirety. These separate pathways provide a basis for tunable effects of the present stimulation strategy on thalamostriatal versus thalamocortical projection systems that may account in part for the observed dissociation of optimal behavioral facilitation stimulation frequencies seen in the experimental monkey studies at high frequencies of stimulation (200 Hz, 150 Hz), and an effect on shortening of reaction times which is maximal for slow frequencies of oscillation, 20 Hz and 40 Hz (see FIG. 27). The facilitation of reaction times may involve selective effects on thalamostriatal projections in conjunction with or as separate antidromic effects on brainstem neurons projecting to CL and Pf. CL, Pf, and the brainstem projecting neurons to CL, Pf are all known to have high threshold P/Q channels that resonate at these low frequencies. See Garcia-Rill et al., "Coherence and Frequency in the Reticular Activating System (RAS)," *Sleep Medicine Reviews,* 17(3):227-238 (2013), which is hereby incorporated by reference herein in its entirety. The observed behavioral dissociations of frequency of stimulation across the DTTm fiber bundle provides an operational basis for selective assessment of stimulation regime on control of movements and thus, in principle, the treatment of impaired movement in isolation of cognitive impairment.

As used herein, intralaminar nuclei also include paralamellar regions, such as parts of the medial dorsal ("MD")

nucleus and the midline nuclei (which are sometimes distinguished from the intralaminar nuclei but, for purposes of the present application, are not).

The TRN may be modulated by the stimulating at least two regions within the intralaminar nuclei. The TRN is distinct from other thalamic nuclei in that the neurons comprising this structure project only to other thalamic nuclei, use an inhibitory neurotransmitter (GABA), and are coupled by electrical (gap junctional) synapses that are the basis for large-scale synchronization within this structure. Shifts in the pattern of TRN activity occur during transitions from sleep to wake (with 'spindle' patterns associated with early sleep stages and tonic firing behavior of the neurons characteristically occurring during wakeful periods). Recent evidence indicates that TRN neurons may entrain other thalamic regions during wakefulness and that short and intermediate term changes in the function of electrical synapses contribute to variations in the strength and duration of this entrainment as discussed for example in Hass et al., "Activity-Dependent Long-Term Depression of Electrical Synapses," *Science* 334(6054):389-393 (2011) and Hestrin, "The Strength of Electrical Synapses," *Science* 334(6054): 315-316 (2011), which are incorporated herein by reference in their entirety.

In addition, the TRN responds selectively to different frequencies of stimulation with stimulation rates greater than 30 Hz producing short-term depression of AMPA receptor-mediated EPSC amplitudes as discussed for example in Mistry et al., "Two Differential Frequency-Dependent Mechanisms Regulating Tonic Firing of Thalamic Reticular Neurons," *European Journal of Neuroscience* 27(10):2643-2656 (2008), which is incorporated by reference herein in its entirety Inhibition of the thalamus by the TRN is compartmentalized and detailed in vitro studies demonstrate that the anterior intralaminar regions (central lateral nucleus) and posterior intralaminar regions have disynaptic projections through the TRN that are mutually inhibitory providing a substrate for overall control of the ongoing dynamics of activity within the thalamus as discussed for example in Crabtree et al., "New Intrathalamic Pathways Allowing Modality-Related and Cross-Modality Switching in the Dorsal Thalamus" *J. Neurosci.* 22(19):8754-61 (2002), which is incorporated by reference herein in its entirety.

One method of stimulation of the TRN and cortical and striatal population is to choose targets within the central thalamus alone. However, in some situations, depending upon lesions or other considerations, stimulation of the thalamus in conjunction with other stimulation sites to control the pattern of TRN activation could be implemented using electrical stimulation, BION technology, or fiberoptic optogenetic approaches using direct or preferably indirect light stimulation of the rostral pole or entire TRN in conjunction with thalamic stimulation. Targets for direct or indirect (via infusion of retroviral vector to change cell bodies of projections to TRN) would be neuronal populations with afferent projection to TRN including globus pallidus externa, substantia nigra, basal forebrain (cholinergic or gabaergic), and brainstem nuclei (parabrachial, locus ceruleus, and cholinergic nuclei).

Specific behavioral regimes seen before, during, and after stimulation of the intralaminar thalamic nuclei arise in part on the basis of alteration of function in the TRN resulting from an interaction of background arousal and motivational state of the animal (and impact on thalamocortical relay, cortical, and TRN neurons) and ON/OFF effects of the effective stimulation configuration that bridges projections from the central lateral thalamic nucleus and parafasicularis-centromedian nuclei. Observed periods of post stimulation drowsiness alternating with hyperactivity during which performance falls to zero arising midway through an experimental session prior to inefficacy of the CT/DBS stimulation may reflect local alteration of the strength of electrical synapses within the TRN. In addition, alteration of glial cells activity in cortex to produce persistent firing patterns may contribute as identified in experimental studies of Sheffield et al., "Slow Integration Leads to Persistent Action Potential Firing in Distal Axons of Coupled Interneurons," *Nat. Neurosci.* 14(2):200-7 (2001), which is incorporated by reference herein in its entirety.

Figure 10:
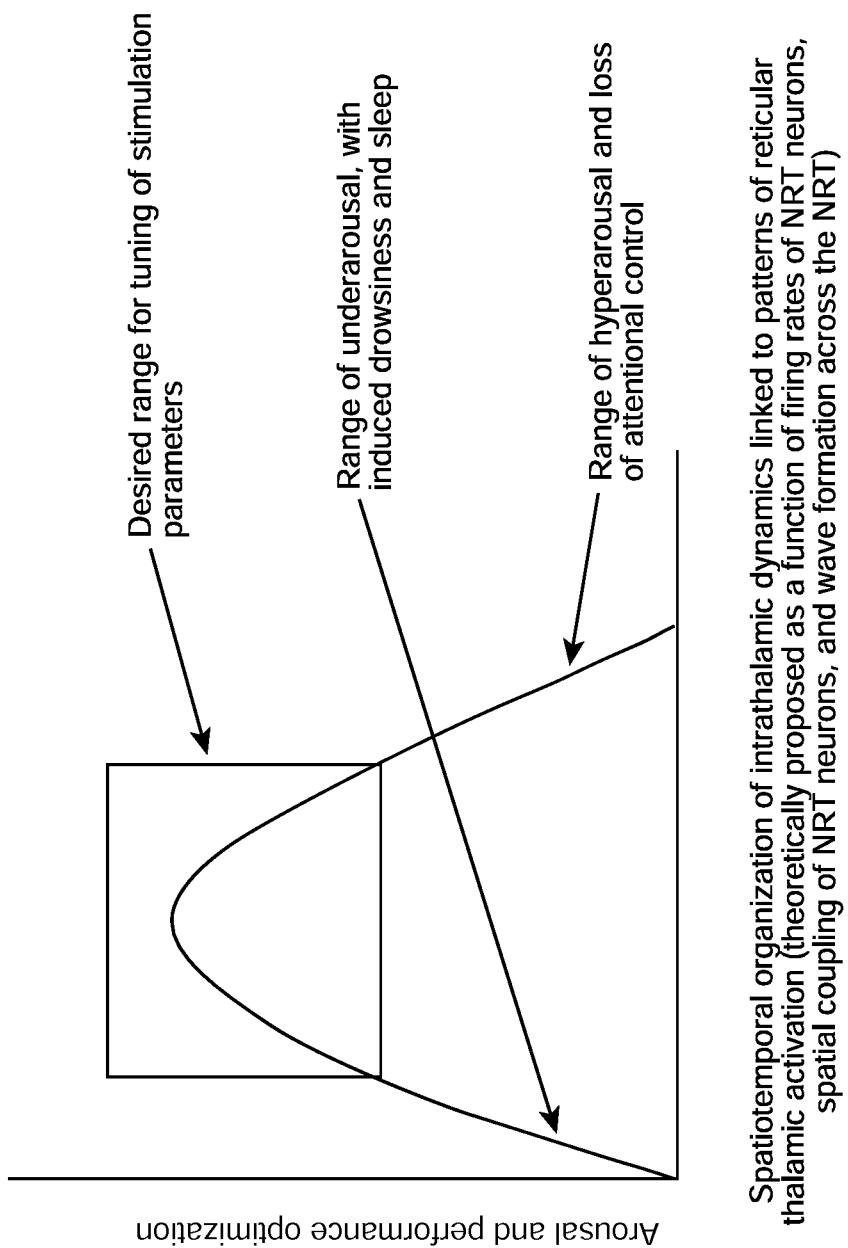
FIG. 10 illustrates a conceptual method for modulation of intrathalamic inhibition influencing dynamics of reticular thalamus linked to a canonical inverted U phenomenon of arousal regulation.

The reversal of both drowsy poor performance and distracted hyperactivity impairing performance suggests an inverted U optimization of arousal as found in other manipulations of the central thalamus with pharmacological modulation or electrical stimulation in controlled experiments testing other cognitive functions such as working memory as illustrated in FIG. 10.

Co-activation of both outflows of intralaminar regions allows for override of intrinsic mechanisms of mutual inhibition and maintenance of cortical activation during the stimulation period with subsequent alteration of propagation of bursting activity within the TRN.

Control of the global pattern of activation of TRN may result as combination of effects of fiber activation of TRN via monosynaptic influences of intralaminar projections from CL and Pf, but also via fibers of passage from brainstem nuclei and disynaptic influences from corticothalamic neurons driven by thalamocortical activation of CL and Pf fibers that have synapses in frontal, prefrontal, and limbic cortical regions. Adjustments of the electric field to optimally control patterns of TRN activity are one mechanism proposed to account for the behavioral control obtained via CT/DBS.

Controlling thalamocortical dynamics in the present invention depends on activation of fibers emanating from the ILN system and innervating the TRN, the striatum, and the cerebral cortex with a predominant impact of prefrontal and frontal cortical afferent projection from the ILN (and related paralaminar nuclei as defined herein). As noted in Groenewegen et al., "The Specificity of the 'Nonspecific'" Midline and Intralaminar Thalamic Nuclei," *Trends in Neuroscience* 17:52-66 (1994), which is incorporated herein by reference in its entirety, the thalamostriatal afferents have a distinct rostrocaudal innervation of the striatum and can be expected to produce directional waves of activation within the striatum when stimulated. Similarly activation of the prefrontal and frontal cortex by ILN afferents will produce waves of activation across corticothalamic connections and back to the TRN via corticoreticular thalamic projections. Strongly directional waves of activity organize the global dynamics of the corticothalamic and TRN systems as discussed for example in Contreras et al., "Control of Spatiotemporal Coherence of a Thalamic Oscillation by Corticothalamic Feedback," *Science* 274:771-774 (1996) and Muller et al., "Propagating Waves In Thalamus, Cortex and the Thalamocortical System: Experiments and Models," *J. Physiol. Paris* 106(5-6):222-38 (2012), which are incorporated herein by reference in their entirety, and via the thalamostriatal projection from ILN, as discussed for example in Groenewegen et al., "The Specificity of the 'Nonspecific" Midline and Intralaminar Thalamic Nuclei," *Trends in Neuroscience* 17:52-66 (1994), which is incorporated herein by reference in its entirety, can be expected to organize spatiotemporal patterns of wave activation across the striatum as well. The strong anisotropy of current application that induces behavioral facilitations reflects the preferred spatiotemporal wave activation across the TRN, frontal cortical, and striatal neuronal populations during stimulation. Controlling the dynamics of the thalamostriatal, thalamocortical, and intrathalamic systems occurs jointly with initiation of activity at the TRN rostral pole activation prior to posterior aspects of the structure, frontal cortex and striatum.

Burst firing in the TRN is a strong component of the propagation of absence seizures and seizures with strong primary or secondary generalization are among the seizure types typically treated with thalamic deep brain stimulation techniques. Thus, control of the intralaminar and brainstem projecting fibers may have application in control of seizures of absence and other types. Moreover, any neuropsychiatric process that alters function of the TRN could be modulated using the approach described here.

Control of the TRN via stimulation across the DTTm is under one theory of the application a basis for optimizing the treatment of generalized or partial complex seizure altering consciousness by reestablishing normal activity within the TRN in awake and asleep states. In asleep states, optimal stimulation frequencies and intensities may be different than in wakeful states. In movement disorders stimulation across the DTTm to optimize patterns of synchronization is proposed under one theory of the present invention to interrupt hypersynchronous activity producing dystonic, akinetic, or parkinsonism disturbances of movement. Although not limited by these examples, other neurological and psychiatric diseases may be expected to improve with control of the TRN dynamics including sleep disorders, generalized epilepsy, and schizophrenia.

Implementation of Multi-Site Stimulation

The goal of multi-site stimulation is to co-activate thalamic projecting fibers to widespread cortical populations (particularly prefrontal/frontal) and striatal projecting neurons while simultaneously controlling global dynamics of the TRN. To achieve these dual aims placement of the stimulators is optimized to capture thalamic and locally present brainstem projecting fibers from both the anterior and posterior compartment of the ILN, nuclei with known disynaptic connection between themselves and the TRN and selective inhibitory connections within the thalamus allowing for specific local inhibitory control as illustrated in FIG. 7. See Crabtree et al., "New Intrathalamic Pathways Allowing Modality-Related and Cross-Modality Switching in the Dorsal Thalamus" *J. Neurosci.* 22(19):8754-61 (2002), which is incorporated by reference herein in its entirety.

In one embodiment, control of TRN and thalamocortical outflow is achieved by broad activation of thalamic projecting fibers leaving posterior ILN (Cm-Pf) and anterior ILN (CL) to induce effective behavioral facilitation. Geometric relationships of the thalamic projecting fiber pathways can be estimated using magnetic resonance imaging techniques (e.g. diffusion tensor imaging, diffusion spectrum imaging, or related methods) while optimal control requires empirical testing and use of several points of placement of stimulators, for adjustment of the applied stimulation in three dimensions.

In another embodiment in which electrodes 15 are used, the anode electrode and cathode electrode placement on at least two stimulators 12 is tested empirically in order to optimize the applied electrical field in three dimensions. Stimulators 12 employing BIONs or optogenetic/fiberoptics may be required or useful in situations where thalamic projecting fiber pathways are interrupted and control of the TRN necessitates activation of ILN components not easily captured using other approaches. In such cases, optimization of placement of electrodes 15 or BIONs 50 (as shown in FIGS. 5A and 5B) can be guided by locally present brainstem fibers which project to the TRN to allow sequential activation of TRN neurons and control of the global dynamics of the TRN.

In an embodiment, the subject may be treated using at least one stimulator 12 in the form of a fiberoptic-optogenetic ("FOG") system 40 as shown in FIGS. 4A and 4B. FOG system 40 is created by first virally transfecting target cells with a vector encoding one or more light-sensitive proteins.

One type of light-sensitive protein that be used, is a light-gated ion channel that is able to generate transmembrane ion transport in response to light. A light-sensitive protein may be responsive to visible light, ultraviolet light, or infrared light. Examples of light-sensitive proteins include but are not limited to Channelrhodopsin-1, Channelrhodopsin-2, LiGluR, ChETA, SFO (step function opsins), OptoXR (light-sensitive GPCR), Volvox Channelrhodopsin-1, Volvox Channelrhodopsin-2 (ChR2), ChIEF, NpHr, eNpHR and combinations thereof. A light-sensitive protein or its active fragment may be used. One or more light-sensitive proteins may be used.

A gene encoding light-sensitive protein can be introduced into the target cells via viral and non-viral vectors and methods. Viral vectors include, but are not limited to, adenoviruses, adeno-associated viruses, retroviruses, lentiviruses, herpes viruses, vaccinia viruses, poxviruses, baculoviruses, and bovine papillomoviruses, and recombinant viruses, such as recombinant adeno-associated virus ("AAV"), recombinant adenoviruses, recombinant retroviruses, recombinant poxviruses, and other known viruses in the art. Methods for assembly of the recombinant vectors are well-known.

An adeno-associated virus is one embodiment. Multiple different serotypes have been reported, including, AAV1, AAV2, AAV3, AAV4, AAV5, and AAV6. The AAV sequences employed in generating the vectors, and capsids, and other constructs used in the present invention may be obtained from a variety of sources. A variety of these viral serotypes and strains are available from the American Type Culture Collection, Manassas, Va., or are available from a variety of academic or commercial sources. The selection of the species and serotype of AAV that provides these sequences is within the skill of the art and does not limit the present invention. The AAV may be self-complementary.

The vector of the present invention may be constructed and produced using the materials and methods described herein, as well as those known to those of skill in the art. Such engineering methods used to construct any embodiment of this invention are known to those with skill in molecular biology and include genetic engineering, recombinant virus engineering and production, and synthetic biology techniques.

The gene may also be delivered through other non-viral methods known in the art, including, but not limited to, plasmids, cosmids and phages, nanoparticles, polymers, electroporation, liposomes, and other means known in the art. It is also possible to use encapsulated cell technology as developed by Neurotech (Lincoln, R.I., USA).

The vector may include appropriate expression control sequences such as transcription initiation, termination, promoter and enhancer sequences; efficient RNA processing signals such as splicing and polyadenylation signals; sequences that stabilize cytoplasmic mRNA; sequences that enhance translation efficiency; sequences that enhance protein stability; and when desired, sequences that enhance protein processing, and/or secretion. A large number of different expression control sequences, e.g., native, constitutive, inducible, and/or tissue-specific, are well known in the art and may be utilized to drive expression of the gene, depending upon the type of expression desired. The selection of the appropriate expression sequences can be accomplished by one of ordinary skill in the art without undue experimentation.

For eukaryotic cells, expression control sequences typically include a promoter, an enhancer, such as one derived from an immunoglobulin gene, SV40, cytomegalovirus, etc., and a polyadenylation sequence which may include splice donor and acceptor sites. The polyadenylation sequence generally is inserted following the transgene sequences and before the 3' ITR sequence. In one embodiment, the bovine growth hormone polyA is used.

Another regulatory component of the vector useful in the methods of the present invention is an internal ribosome entry site ("IRES"). An IRES sequence, or other suitable system may be used to produce more than one polypeptide from a single gene transcript. An IRES sequence (or other suitable sequence) is used to produce a protein that contains more than one polypeptide chain or to express two different proteins from or within the same cell.

The selection of the promoter to be employed in the vector may be made from among a wide number of constitutive or inducible promoters that can express the selected transgene in the target cell. In one embodiment, the promoter is cell-specific. The term "cell-specific" means that the particular promoter selected for the recombinant vector can direct expression of the selected transgene in a particular ocular cell type. In one embodiment, the promoter is specific for expression of the transgene in thalamocortical relay cells. In another embodiment of the use of FOG techniques transfection of TRN neurons, preferentially within rostral pole using retroviral techniques could be used to allow uptake of transgenes in structures with projection to the TRN. In these cases, different cell type promoters to target neurons within globus pallidus externa, substantia nigra, basal forebrain (cholinergic or gabaergic), brainstem nuclei (parabrachial, locus ceruleus, and cholinergic nuclei), or other structures with afferent projections to the TRN could be used.

In one embodiment, multiple classes of target cells are targeted, and different light-sensitive proteins, may be expressed in different classes of cells.

Examples of constitutive promoters which may be included in the vector of this invention include, without limitation, the CMV immediate early enhancer/chicken β-actin (CβA) promoter-exon 1-intron 1 element, the RSV LTR promoter/enhancer, the SV40 promoter, the CMV promoter, the 381 bp CMV immediate early gene enhancer, the dihydrofolate reductase promoter, the phosphoglycerol kinase (PGK) promoter, and the 578 bp CBA promoter-exon1-intron1. See Koilkonda R D et al. "Efficient Expression of Self-Complementary AAV in Ganglion Cells of the Ex Vivo Primate Retina". *Mol Vis.* 15:2796-802 (2009), which is hereby incorporated herein by reference in its entirety. Promoter analysis can be used to identify promoter functional fragments and derivatives. See McGowan M H et al., "Characterization of the Mouse Aldose Reductase Gene and Promoter in a Lens Epithelial Cell Line." *Mol Vis.* 28; 4:2 (1998) and Bookstein R., et al. "Promoter Deletion and Loss of Retinoblastoma Gene Expression in Human Prostate Carcinoma," *Proc Natl Acad Sci USA.* 87(19):7762-6 (1990), each of which is incorporated herein by reference in its entirety.

Alternatively, an inducible promoter is employed to express the transgene product, so as to control the amount and timing of the target cell's production. Inducible promoters include those known in the art and those discussed above including, without limitation, the zinc-inducible sheep metallothionine ("MT") promoter; the dexamethasone (Dex)-inducible mouse mammary tumor virus ("MMTV") promoter; the T7 promoter; the ecdysone insect promoter; the tetracycline-repressible system; the tetracycline-inducible system; the RU486-inducible system; and the rapamycin-inducible system. Any type of inducible promoter that is tightly regulated may be used. Other types of inducible promoters which may be useful in this context are those which are regulated by a specific physiological state, e.g., temperature, acute phase, a particularly differentiation state of the cell, or in replicating cells only.

Selection of these and other common vector and regulatory elements are conventional and many such sequences are commercially available. Of course, not all vectors and expression control sequences will function equally well to express all of the transgenes of this invention. However, one of skill in the art may make a selection among these expression control sequences without departing from the scope of this invention. Suitable promoter/enhancer sequences may be selected by one of skill in the art using the guidance provided by this application. Such selection is a routine matter and is not a limitation of the molecule or construct. For instance, one may select one or more expression control sequences, operably link the sequence to a transgene of interest, and insert the expression control sequence and the transgene into a vector. The vector may be packaged into an infectious particle or virion following one of the methods for packaging the vector taught in the art.

The vector containing the desired light-sensitive element and cell-specific promoter for use in the target cell(s) as detailed above is preferably assessed for contamination by conventional methods and then formulated into a pharmaceutical composition intended for injection. Such formulation involves the use of a pharmaceutically and/or physiologically acceptable vehicle or carrier, such as buffered saline or other buffers, e.g., HEPES, to maintain pH at appropriate physiological levels. If the virus is to be stored long-term, it may be frozen in the presence of glycerol.

According to the method of the present invention for treating a subject with a condition as described herein, the composition described above is administered to said subject. Methods for administering vectors to the brain are well known to the art. See, e.g., WO2007044023 and U.S. Pat. No. 7,972,308 B2, which are incorporated herein by reference in their entirety.

An effective amount of a vector carrying a nucleic acid sequence encoding the desired light-sensitive element under the control of the cell-specific promoter sequence may range between about $1 \times 10^9$ to $2 \times 10^{12}$ infectious units in a volume of between about 150 to about 800 microliters. The infectious units are measured as described in McLaughlin S K, et al. "Adeno-Associated Virus General Transduction Vectors: Analysis of Proviral Structures." *J Virol.* 62(6):1963-73 (1988), which is incorporated herein by reference in its entirety. More desirably, an effective amount is between about $1 \times 10^{10}$ to $2 \times 10^{11}$ infectious units in a volume of between about 250 to about 500 microliters. Still other dosages in these ranges may be selected by the attending physician, taking into account the physical state of the subject being treated, the age of the subject, the particular disease or condition, and the degree to which the disorder, if progressive, has developed.

It may also be desirable to administer subsequent dosages of the pharmaceutical compositions of this invention. For example, depending upon the duration of the transgene within the target cell, one may deliver booster dosages at 6 month intervals, or yearly following the first administration.

The target cells to which light-sensitive protein is delivered are located in regions including but are not limited to cells in the brain, including but not limited to central thalamus, the thalamic reticular nucleus, striatum, basal forebrain, and brainstem. The following cell types in said regions may be targeted: thalamocortical relay cells, globus pallidus interna neurons, and substantia nigra pars reticulate neurons.

Such booster dosages and the need therefore can be monitored by the attending physicians, using, for example, the behavior tests as described herein. Other similar tests may be used to determine the status of the treated subject over time. Selection of the appropriate tests may be made by the attending physician.

In a separate procedure or during the same procedure as delivery of the light-sensitive protein, a fiberoptic system is implanted which administers light to the target cells comprising light-sensitive protein. Such fiberoptic systems are known in the art. See for example U.S. Pat. No. 7,288,108, which is incorporated herein by reference in its entirety. A fiberoptic system comprises at least one fiber optic cable, at least one light source, and a device for controlling the light source(s). The fiberoptic system may comprise one or more sensors. The fiberoptic system may be able to provide light in one or more wavelengths, and at one or more intensities, to one or more fiberoptic cables. The fiber optic system may deliver violet light (380-450 nm); blue light (450-475 nm); cyan light (476-495 nm); green light (495-570 nm); yellow light (570-590 nm); orange light (590-620 nm), red light (620-750 nm), near-infrared light (750-2,500 nm), or bands of light spanning these ranges or encompassing multiple ranges.

Specific light-sensitive proteins may be targeted with specific wavelengths to achieve desired results. For example and without limitation, yellow light may be directed to target cells transfected with halorhodopsin to generate hyperpolarizing currents in the target cell; blue light may be delivered to target cells transfected with channelrhodopsin in order to depolarize the target cell.

Regardless of the type of stimulator used, the stimulation may be continuous, intermittent, or periodic. The range of stimulation frequencies and intensity of stimulation will depend on several factors: impedance of the electrode once in the brain (when electrodes are used), excitation properties of cells which may differ within subdivisions of the intralaminar nuclei, the type of induced physiologic responses sought for a particular subject, and interindividual variation. Suitable stimulation frequencies range from about 1 Hz to 1 kHz; from about 10 Hz to about 500 Hz; and from about 50 Hz to about 250 Hz. Higher frequencies can be utilized where amplitude or frequency modulated signals are used.

Behavioral performance on tasks requiring sustained attention may be enhanced by passing electrical current between two or more stimulators 12 located in at least one nucleus, or in different nuclei of the central thalamus or stimulation across the boundaries of a single nucleus, for example, Cm-Pf to modulate symptoms of akinesia in movement disorders. The direction of current flow between stimulators 12 is chosen to produce the maximal behavioral effect. The timing of the current flow is structured as periodic sequences of biphasic pulses with pulse frequencies, amplitudes and inter-pulse intervals selected from values that are effective in shaping behavioral performance.

The stimulation may be delivered to more than one stimulator 12 placed in one or more subcortical structures such as the central thalamus and striatum. The temporal pattern of electrical activity amongst stimulators 12 can be one of several modes, including but not limited to: 1) alternation of ON and OFF epochs (of approximately equal length for two stimulators 12) of periodic biphasic stimulation with only one stimulator being in the ON state at any one time; 2) simultaneous periodic biphasic stimulation across all of the stimulators 12; 3) ON epochs separated by short delay periods when all of the stimulators are silent.

In embodiments in which electrodes 15 are used in stimulators 12, a number of configurations of cathode/anode pairs formed on or between any two electrodes 15 are possible. Bipolar currents produced may be produced across electrodes 15 on a single stimulator, or with bipolar currents set up between electrodes 15 on different stimulators. In one embodiment, a double bipolar (not quadropolar) distribution of cathode/anode pairs is formed between two electrodes 15 on two stimulators 12. In a configuration in which multiple stimulators 12 are used, the pole of each electrode 15 on a single stimulator 12 may be the same (for example, two electrodes 15 on one stimulator 12 are both anodes, and two electrodes 15 on another stimulator 12 are anodes). Likewise if there are two electrodes 15 on a single stimulator 12, the pole of each electrode 15 on said stimulator 12 may be different, or in cases in which there are more than two electrodes 15, some may be different and some may be the same. The time-course of a bipolar pulse may follow that of the classic "Lilly pulse."

In one embodiment of the present invention, the configuration of electrodes 15 stimulates a volume including the centromedian and parafasciular nuclei with the initial cathodic phase of the pulse during each cycle. Frequency of stimulation may, for example, range from <0.01 Hz to 1000 Hz, more preferably in the 10 Hz to 300 Hz in wakeful states. In sleep states, background frequencies of cortical, striatal, and thalamic neurons reduces during sleep stages and if stimulation is maintained during sleep states (as opposed to phasic off periods overnight as done for example, in Schiff et al., "Behavioural Improvements with Thalamic Stimulation After Severe Traumatic Brain Injury," Nature 448(7153):600-3 (2007), which is incorporated herein by reference in its entirety, then variation in amplitude, pulse width, duty cycle, and frequency of stimulation with stimulation at lower frequencies of 0.01 Hz to 10 Hz or 14-16 Hz may be preferred although application would not be limited by these examplary frequency ranges. In one envisioned application, lower amplitude stimulation at frequencies of 2-4 Hz during slow wave sleep may be used to enhance synaptic plasticity effects of slow waves.

Conditions and Diseases

Applications of the devices and methods described above include: improving impaired cognitive function, treating a disorder of consciousness, treatment of epilepsy, including but not limited generalized seizures, treating a degenerative or developmental disorder, treating a movement disorder, and treating a neuropsychiatric illness. A system, devices, and methods for altering large-scale dynamics of corticothalamic systems that affect cognitive functions, generalized seizures, movement disorders, pain and other forms of altered dynamics within the corticothalamic system that may be present in brain injuries, neuropsychiatric disorders, developmental disorders, or degenerative disorders are described.

Without being limited by any particular theory, the mechanism underlying the role of central thalamic brain stimulation in remediation of altered function in the corticothalamic system is proposed that supports the use of the invention. The present invention applies primarily to brain disorders that exhibit alteration of function of neocortical, striatal, and thalamic neurons. Such alteration may be the loss of neuronal firing of each population as result of deafferentation injuries produced by trauma, hypoxia, or other insults to the brain or altered patterns of firing of neurons as may be identified in disorders producing types of epilepsy, parkinsonism, dystonia, choreaform movement disorders, apathetic behavioral disturbances associated with structural brain injuries, or neuropsychiatric conditions such as schizophrenia that may respond to selective pharmacologic interventions (e.g. zolpidem responsive post-stroke apathy or catatonia, acetylcholinesterase inhibitor responsive oculogyric crisis, and akinetic mutism resulting from post-encephalitic parkinsonism), and other condition not limited by these examples.

Electrical stimulation of the deafferented central thalamus produces a shift of level of synaptic input to severely deafferented neurons across neocortex, striatum, and other components of thalamus and induce reversal of abnormal 'circuit' level dynamics resulting from broadly reduced background synaptic activity across corticothalamic and cortico-striatopallidal-thalamocortical systems as discussed, for example, in Schiff, "Moving Toward a Generalizable Application of Central Thalamic Deep Brain Stimulation For Support of Forebrain Arousal Regulation in the Severely Injured Brain," *Ann N Y Acad Sci.* 1265:56-68 (2012), which is incorporated herein by reference in its entirety.

As applied to less severe structural brain injuries a greater functional contribution is provided from the effects of alteration of the quality of neuronal firing patterns of neocortical pyramidal cells which show marked sensitivity to small differences in level of depolarization of their neuronal membrane. Such shifts in firing patterns of neocortical neurons are expected to engage local network activity generated changes in neuronal responsiveness across wide cortical territories. In this way, central thalamic brain stimulation effectively supports cerebral activity in the injured brain that would otherwise be regulated by the arousal regulation system connections of the medial frontal cortices, central thalamus, and brainstem modulatory system typically engaged in this ongoing evaluative and regulatory activity. Collectively, these mechanisms will selectively provide support to neuronal populations engaged in adaptive allocation of cognitive resources, including attentive behavior and working memory during ongoing behaviors. The optimal implementation of the approach requires the maintaining of control of the global patterns and sequence of activation across the forebrain and specifically across the TRN.

In the structurally intact brain or structurally injured brain with epilepsy or altered function in neocortical, striatal, and thalamic neurons associated with movement disorders such as parkinsonism, dystonia, dykinesia, chorea, and similar disturbances, the same mechanisms will act to normalize firing patterns of neocortical, striatal, and thalamic neurons and specifically desynchronize and maintain constant patterns of wave activation from rostral pole to the caudal aspects of the TRN that will act to suppress paroxysmal epileptiform and abnormal patterns of TRN activation associated with movement disorders such as parkinsonism, dystonia, dykinesia, chorea, and similar disturbances.

In the situation of structural brain injuries, particularly those causing altered function within the region of the central thalamus, it is possible that a combination of impaired cognitive function resulting from direct injuries to the central thalamus may combine with intermittent generalized seizure activity, such as discussed, for example, in Williams et al., "Thalamic Activity in Atupor," *Brain* 74(4): 377-98 (1951); van Domburg et al., "Akinetic Mutism with Bithalamic Infarction," *Neurophysiological correlates. J Neurol Sci.* 139(1):58-65 (1996); and Burruss et al. "Episodically Remitting Akinetic Mutism Following Subarachnoid Hemorrhage," *J Neuropsychiatry Clin Neurosci.* 11(1): 100-2 (1999), which are incorporated herein by reference in their entirety, and paroxysmal or more sustained movement disorders as discussed for example, in Lera et al., "A Combined Pattern of Movement Disorders Resulting from Posterolateral Thalamic Lesions of a Vascular Nature: A Syndrome with Clinico-Radiologic Correlation," *Mov Disord.* 15(1):120-6 (2000); and Lee et al., "Movement Disorders Following Lesions of the Thalamus or Subthalamic Region," *Mov Disord.* 9(5):493-507 (1994), which are incorporated herein by reference in their entirety.

In such cases the devices and methods described above may be used to optimize and control the level of cognitive performance and suppression of generalized seizures and movement disorders via the common underlying mechanism of regularization of firing activity from central thalamic afferent and control of the directional waves of activity across TRN acting together to produce improved thalamo-cortical and thalamostriatal outflow patterns and in turn, will produce improved response of cortical and striatal targets involved in supporting organized goal-directed behaviors altered by structural brain injuries. Similarly, use of the described devices and methods may be applied to more complex brain injuries exhibiting a mix of cognitive impairment, seizures, and movement disorders.

In one embodiment, the above-described devices and methods may be applied to all current applications of thalamic deep brain stimulation. Thalamic brain stimulation in human subjects has been used to ameliorate movement disorders including tremor, dystonia and Tourette's syndrome; pain disorders, seizure disorders, and disorders of consciousness. Applications of thalamic brain stimulation have also been envisioned for a range of neuropsychiatric disorders. In each possible application, the optimal control of intrathalamic and thalamocortical dynamics depends on activity within the intralaminar thalamic ("ILN") system and the TRN.

The devices and methods described above are also useful for treatment of epilepsy and improving efficacy of existing anterior thalamic stimulation methods in human subjects as discussed, for example, in Fisher, "Therapeutic Devices for Epilepsy," *Ann. Neurol.* 71(2)157-68 (2012), which is incorporated herein by reference in its entirety. Experimental studies demonstrate that activation of the rostral intralaminar nuclei can interrupt primary generalized seizures as set forth, for example, in Seidenbecher et al., "Contribution of Intralaminar Thalmic Nuclei to Spike-and-wave Discharges in a Genetic Model of Absence Epilepsy," *Eur. J. Neurosci.* 13:1537-46 (2001), which is incorporated herein by reference in its entirety.

In one embodiment of the present invention, control of the patterns of activity across the entire structure of the TRN will achieve an effective and lasting disruption of refractory generalized seizure. Without being limited by any particular theory, control of sequential activation of the TRN to initiate first activation at the rostral pole with subsequent recruitment of more caudal components of the thalamic reticular nucleus, will produce a consistent wave of activity, regularizing the sequential depolarization of the thalamic reticular neurons and patterns of firing rates of thalamic relay neurons maintaining conditions consistent with attentive wakefulness and resisting patterns of activity producing generalized seizures, dystonic, parkinsonian, and allied impairments of the motor control system and, under high frequency stimulation conditions, resisting the shift to sleep states.

In vivo studies demonstrate that such strongly directional waves of activity organize the global dynamics of the TRN, such as discussed in Contreras et al., "Control of Spatiotemporal Coherence of a Thalamic Oscillation by Corticothalamic Feedback," *Science* 274: 771-774 (1996); and Muller et al., "Propagating Waves in Thalamus, Cortex and the Thalamocortical System: Experiments and Models," *J Physiol Paris:* 106(5-6):222-38 (2012), which are incorporated herein by reference in their entirety. The strong anisotropy of current application that produces induced behavioral effects reflects the preferred spatiotemporal activation across the TRN and the frontal cortical and striatal neuronal populations during stimulation that initiates TRN rostral pole activation prior to posterior aspects of the structure. The present methods and devices will also be useful in the treatment of movement disorders including non-parkinsonian forms of hyperkinetic or bradykinetic disorders by controlling inhibition within the thalamus.

The present invention also provides methods and devices for treating a subject with impaired cognitive function. As used herein, cognitive function means the information processing capacities of the brain, including all semantic information processing, including interpretation of external and internal sensory signals, reward/motivational value processing and integration of those signals to support behavior.

The present invention also provides methods and devices for treating a subject with neuropsychiatric disease including patients with catatonic symptoms or symptoms related to catatonic phenomenology such as cognitive slowing, abulia, and apathy. These symptoms and behavioral features, shared by many neuropsychiatric disorders such as schizophrenia, have their origin in altered function of the frontal/prefrontal striatal systems and may benefit from the devices and methods described herein.

Perceptual awareness, as used herein, is a subset of cognitive function and is meant to include the mechanisms of selecting, organizing, and classifying internally or externally generated brain signals. A variety of methods can be used to assess a subject's cognitive function and to detect deficits in perceptual awareness. These include clinical neurological and neuropsychological evaluation.

In one embodiment, the present invention relates to a methods and devices for treating a conscious subject having impaired cognitive function. Conscious, as used herein, has the conventional meaning, as set forth in Posner, et al., *Plum and Posner's The Diagnosis of Stupor and Coma*, Oxford, New York (2007), which is incorporated herein by reference in its entirety. Conscious subjects include those who have a capacity for reliable, reproducible, interactive behavior evidencing awareness of self or the environment. Conscious subjects include subjects who recover consciousness with less severe brain injury but who, because of their impaired cognitive function, do not reach independent living and remain in nursing facilities.

Impaired cognitive function is manifested in deficits, including but not limited to, attention, intention, motivation/ reward processing, working memory, and/or awareness, which may occur singly or in combination. As used herein, attention refers to the cognitive function that provides the capacities for selection of internal or external stimuli and thoughts, supports the preparation of intended behaviors (e.g., speeds perceptual judgments and reaction times), and supports the maintenance of sustained cognition or motor behaviors (e.g., the focusing of attention). Intention, as used herein, refers to the cognitive mechanism of response failures, such as lack of behavioral interaction, which is not due to a perceptual loss. In other words, intention is the cognitive drive linking sensory-motor integration to behavior. Intention deficits include failure to move a body part despite intact motor pathways, awareness, and sensory processing as demonstrated by neurophysiological and neuropsychological evaluation. Another example of a subject's intention deficit is a failure to initiate action of any kind despite evidence of awareness or action produced by stimulation. Loss of intention is a disorder of cognitive function, as defined herein, and is a major division of the neuropsychological disorder of neglect, which may be present in many subjects with cognitive deficits. Such deficits of intention are also described as "drive disorders," "apathy," "abulia," or "cognitive slowing."

Working memory, as used herein, refers to the fast memory process required for on-line storage and retrieval of information, including processes of holding incoming information in short-term memory before it can be converted into long-term memory and processes which support the retrieval of established long-term (episodic) memories. Deficits in awareness relate to impaired perceptual awareness, as described above. In the intact normal brain, arousal regulation in support of varying cognitive demand met with increases in attentional effort and working memory. In addition, intentional control is adaptively allocated by the central thalamus in conjunction with systems in frontal/prefrontal cortex and the brainstem among other controllers. The failure of the central thalamus to provide adequate baseline arousal regulation support and adaptive adjustments is expected after all types and severity of structural brain injuries producing cognitive impairment. As such, central thalamic stimulation, as described here, compensates and supports activity from the central thalamus to widespread cerebral regions typically provided by intrinsic arousal regulation in the normal brain.

Clinical signs of impaired cognitive function also may include one or more of the following: profound hemi-spatial neglect, disorders of motor intention, disorders of impaired awareness of behavioral control, apathy, and cognitive slowing.

The subject may suffer from one or more other ailments in addition to impaired cognitive function. Such other ailments include but are not limited to chronic pain and seizures, which may be generalized seizures. As used herein, chronic pain means a syndrome of protracted pain, typically resulting from a persistent activation of central pain mechanisms (for example, in the brain (commonly referred to as "neuropathic pain") as opposed to pain which results primarily from activation of pain mechanisms in the peripheral nervous system. As used herein, seizures include generalized seizures, which include but are not limited to epileptic seizures, which include but are not limited to seizures experienced by severe medication-resistant refractory epileptics (i.e., subjects who have been treated with multiple anti-epileptic medications at near toxic doses and failed this therapy as evidenced by their continuing to have multiple seizures daily despite such medication).

The present invention can be practiced on a subject whose impaired cognitive function (e.g., impaired perceptual awareness) is, for example, produced, at least in part, by brain injuries, which may be caused by conditions, disease, or events including but not limited to stroke, head trauma (including but not limited to blunt head trauma or missile penetration), toxicological agents (including but not limited to carbon monoxide, arsenic, or thallium), anoxia, ischemia, nutritional deficiencies, developmental diseases, infectious diseases, neoplastic diseases, degenerative diseases, complications thereof, or other structural lesions. The subject's impaired cognitive function may be due to post encephalitic parkinsonism or other disease processes which include oculogyric crises as a symptom.

A subject's cognitive function, such as his or her attention, intention, working memory, and/or awareness function, can be evaluated using standard tests. Most of these test batteries encompass evaluation of the different types of basic cognitive functions and are used to initially screen a subject for a pattern of deficits. More specific tests can be employed and individualized to a subject's neuropsychological profile. In practice, the choice of particular neuropsychological test batteries depends on the experience of the tester and the normative data available for the test. This changes as new studies are done and as new testing materials are tried out and compared. For example, suitable comprehensive tests include the Mental Status Exam ("MSE") (set forth, for example, in Strub et al., *The Mental Status Exam in Neurology*, 3rd ed., Philadelphia:Davis (1993), which is incorporated herein by reference in its entirety) as well as broad neuropsychological test batteries, like the Halstead-Reitan Neuropsychological Test Battery (which encompasses memory, attention, intention, and perception/awareness). In order to delineate more narrowly specific deficits of working memory, attention, perception, etc., more individualized tests can be chosen. For example, a 'Shipley-Hartford scale' test may be employed to assess cognitive slowing (intelligence); a 'Bender-Gestalt' test can be used to assess spatial relations and constructions; Aphasia screening tests, such as the Boston Diagnostic Aphasia Examination or the Western Aphasia Battery, can detect language dysfunction; and Trials A/B or Memory Assessment Scales ("MAS") test can be used to assess working memory. Further details with regard to these and other tests for assessing a subject's attention, intention, working memory, and/or awareness function can be found in, for example, Berg, "Screening Tests in Clinical Neuropsychology," Chapter 10, pp. 331-363, and in Horton et al., eds., *The Neuropsychology Handbook*, Vol. 1, Foundations and Assessment, 2nd ed., New York:Springer Publishing Company (1997), which are incorporated herein by reference in their entirety.

Clinical guidelines for subject selection are based on the subject's functional disturbance. For example, the subject's cognitive impairment may be slowing (or, in a severe case, dementia), as manifested in the subject's decreased attention, impaired intention, and decreased working memory. Alternatively, the subject may exhibit primary failure to initiate action despite interaction when stimulated. Subject selection in the clinical setting would also depend, in part, on prognostic signs, such as the presence of spontaneous fluctuations in functional level, modulation of functional level by external stimulation, or reliably produced modulation by internally generated stimulation.

Impaired cognitive function may be objectively measured across outcomes of severe brain injuries and related neurological impairments. At the most extreme end of disability, cognitive function can be captured on the Coma Recovery Scale-Revised ("CRS-R"), as discussed for example in Giacino et al., "The JFK Coma Recovery Scale-Revised: Measurement Characteristics and Diagnostic Utility." *Archives of Physical Medicine and Rehabilitation*, 85(12):2020-2029 (2004), which is incorporated herein by reference in its entirety. The CRS-R is a well-validated metric for behavioral function ranging from vegetative state to emergence from minimally conscious state. Cognitive function above the level captured by the CRS-R for patients fulfilling the diagnosis of confusional state can be measured by Confusion Assessment Protocol ("CAP") and the Mississippi Aphasia Screening Test ("MAST"). For patients with cognitive function above the levels of CRS-R, CAP, and MAST, a standard neuropsychological test as described above can be used. Cognitive impairment on these tests would reflect reductions of scores on these measures from pre-existing baselines which could affect social and vocational reintegration after injury. For patients with developmental or other disorders producing stable but low cognitive function scores in the lower percentiles (e.g. first decile) may best measure impaired cognitive function.

In one embodiment, the subject has severely impaired cognitive function, as defined by the functional range captured on the Coma-Recovery Scale-Revised, CRS-R (Giacino et al., "The JFK Coma Recovery Scale—Revised: Measurement Characteristics and Diagnostic Utility," *Archives of Physical Medicine and Rehabilitation*, 85(12): 2020-2029 (2004), which is hereby incorporated by reference in its entirety), or Confusion Assessment Protocol CAP (Sherer, et al., "Multidimensional Assessment For Acute Confusion After TBI," *Archives of Physical Medicine and Rehabilitation*, 86:896-904 (2005)). In another embodiment, the subject has mild to moderate cognitive impairment, as defined by significant reduction of function on standard psychometric test relative to the subject's premorbid baseline, (i.e., level of cognitive function and capacity prior to the initial brain injury event in the case of a patient with an acquired brain injury). However, the method and system of the present invention is not limited to use for cognitive impairment after acquired brain injury.

EXAMPLES

The present description is further illustrated by the following examples, which should not be construed as limiting in any way.

Example 1

Behavioral Experiments

A primate model was developed for evaluating strategies to modulate cognitive performance through deep brain stimulation. Towards this goal, a macaque monkey was implanted with a fixed set of 10 EEG electrodes, a recording chamber with a 32-microelectrode microdrive (Gray Matter Research), and an in-house designed Deep Brain Stimulation and Recording System (DRBS) as shown in FIG. 1B. The recording chamber was placed over the frontal lobe of the monkey to allow for simultaneous multichannel single-unit and local field potential (LFP) recording from the frontal eye fields (FEF), the dorsal lateral prefrontal cortex (DLPF) and the dorsal striatum. The DBRS was implanted over the parietal lobe to allow for deep brain stimulation and local field potential recording in the central thalamus. Two DBS electrode-based stimulators were placed in the central thalamus approximately 3 mm apart, one in the anterior intralaminar nuclei (hereinafter referenced as the rostral stimulator) and the other in the posterior intralaminar nuclei (hereinafter referenced as the caudal stimulator). The DBS electrode-based stimulators are scaled-down versions of human DBS electrode-based stimulators (NuMED, Inc.). Each DBS stimulator possessed six platinum/iridium electrodes (impedances of 100-150M), each 0.5 mm in length with a separation distance of 0.5 mm between electrodes. A computer-controlled external pulse generator is used to drive the individual electrodes.

Figure 11:
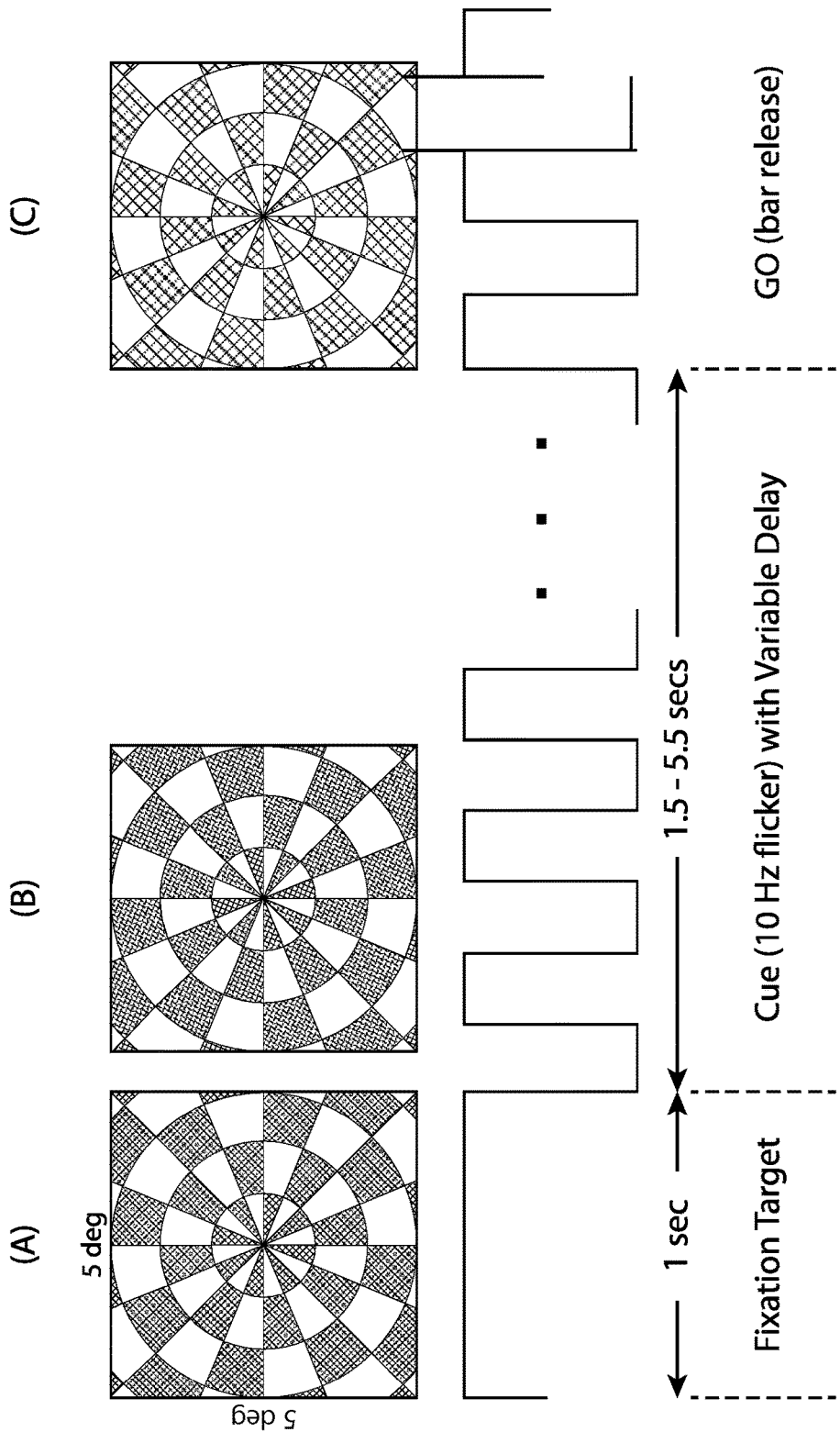
FIG. 11 illustrates a behavioral task associating visual stimuli (a dartboard pattern) displayed on a video screen with the cues and commands of several behavioral tasks.

The monkey was trained to sit in a chair (Crist Instruments, Inc.) with its head fixed and to manipulate a contact bar in order to receive liquid rewards. The monkey learned to associate visual stimuli displayed on a video screen with the cues and commands of several behavioral tasks. In one such task, as shown in FIG. 11, a red and black dartboard pattern (A) appeared on the video screen at 1 of 9 locations chosen at random on each trial. When the monkey moved its gaze over the visual target and maintained fixation within a degree of the center of the target, the behavioral trial was initiated. The monkey's gaze was monitored by an infrared eye-tracking system and the behavioral control computer. After a period of 1 second, the dartboard pattern flickered at 10 Hz which cued the monkey that a variable delay period had begun. The duration of the delay period was a normally distributed random variable with a mean of 3 seconds and standard deviation of 500 ms. If the monkey's hand was not on the contact bar at the start of the delay period, the trial would abort and the monkey would receive no reward. If, however, the monkey kept its hand on the bar, and its gaze centered on the flickering target, the dartboard would turn from red and black to green and black (C) at the end of the delay period. This change in color was to be interpreted by the monkey as a GO signal which required that the monkey move its hand away from the bar within 1 second after the time of the color change. A successful bar release was rewarded with a sip of water. The monkey did 1000-2000 such trials during a typical day's behavioral recording session.

Deep Brain Stimulation Paradigms

The goal of deep brain stimulation is to produce a change in activity in a targeted region of neural tissue and thus to modulate behavior and/or cognition. The deep brain stimulation used in these studies delivered a modulating current pulse through a volume of tissue in the central thalamus. The placement of the cathodes and anodes in the tissue, the pulse shape, and the frequency and amplitude of the pulses were explored in this study. Deep brain stimulation was implemented with a 4-channel constant-current stimulus generator (Multichannel Systems, Reutlingen, Germany). The cathode-anode outputs from each channel could be used to provide bipolar constant-current stimulation in the central thalamus through any pair of electrode contacts across the two implanted DBS electrodes.

A number of configurations of cathode/anode pairs formed on or between the two thalamic electrodes were explored. The performance of the monkey was examined on sustained attention and texture categorization tasks with bipolar currents produced across electrodes on either the rostral or caudal stimulator, and with bipolar currents set-up between electrodes between the two stimulators.

One particular configuration, a double bipolar (not quadropolar) distribution of cathode/anode pairs formed between the bottom two electrodes on both stimulators, proved to be the most reliable at modulating behavior. Behavioral performance was also sensitive to the amplitude of current modulation and its frequency. The time-course of the bipolar pulse followed that of the classic "Lilly pulse." The optimal configuration stimulated a volume including the centromedian and parafasciular nuclei with the initial cathodic phase of the pulse during each cycle. The optimal stimulation cycle length was less than 6.7 msec (150 and 200 Hz). Amplitudes greater than 1.5 mA were required to reliably change behavioral performance.

Behavioral Results

Observations during the behavioral recording/stimulation sessions and the post-processing of correct/incorrect performance and reaction time data both played important roles in optimizing central thalamic stimulation parameters. The search through the DBS parameter space was steered mostly by measures of behavioral performance that looked at trial-to-trial variation. Long-term session trends in the fraction of correct trials and latency of the responses also contributed to DBS analysis.

Figure 12:
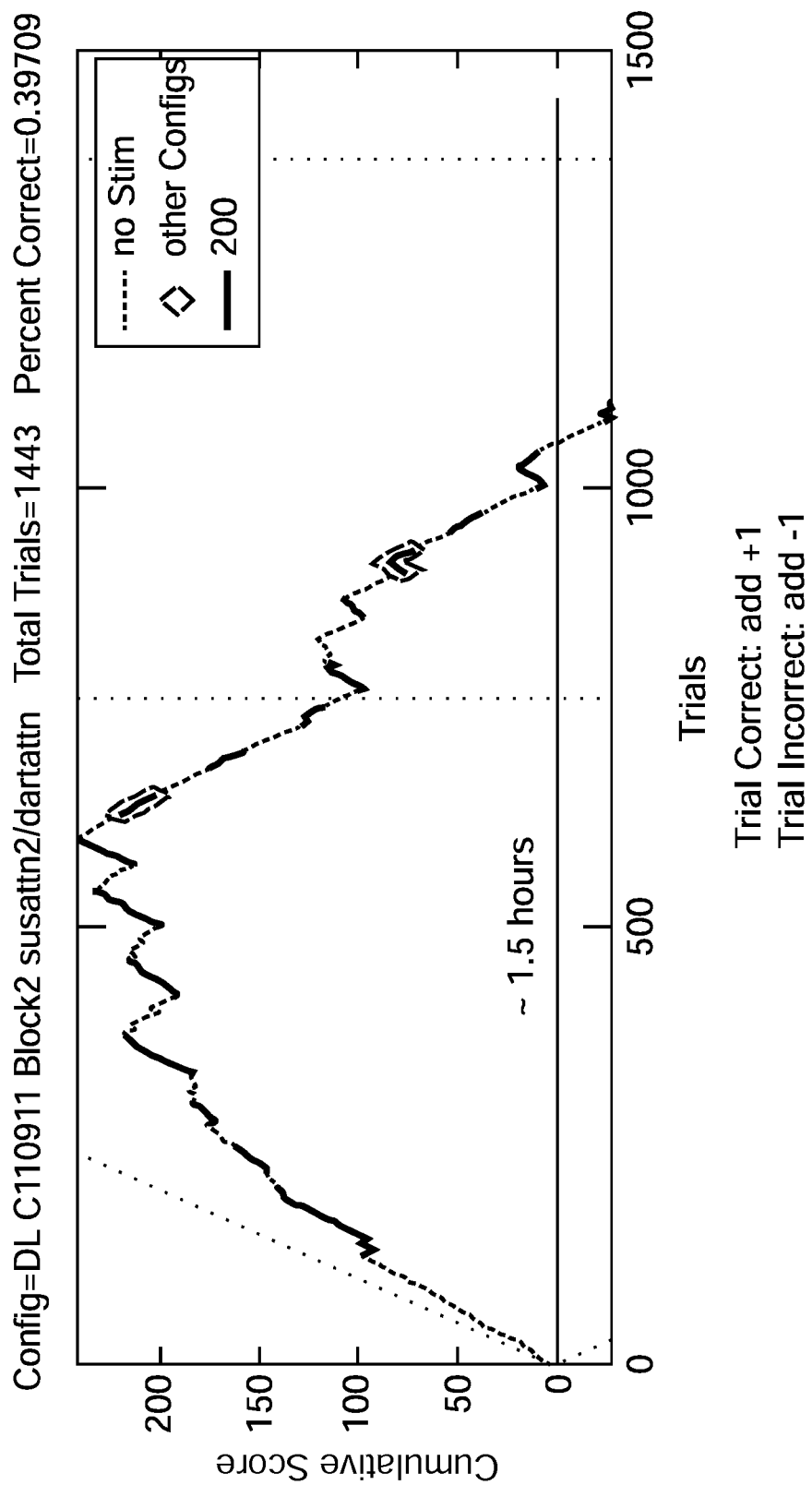
FIG. 12 illustrates a running (cumulative) score for a typical behavioral recording/stimulation session based on the behavioral task shown in FIG. 11.

One method for examining DBS modulation of behavioral performance is to plot a running score of correct and incorrect trials; at each trial, add 1 to the cumulative score if the trial is correct or add −1 if the trial is incorrect. In FIG. 12, the running (cumulative) score for a typical behavioral recording/stimulation session is plotted for the first 1100 of 1443 total trials. If the monkey performed perfectly, the curve would follow the dashed oblique line with a slope of 1. If all trials were incorrect, a line with a slope of −1 would be produced. Random performance generates a curve that fluctuates around a line with a slope of 0. As shown in FIG. 12, nearly all trials were correct before the first presentation of DBS. The running score (dashed curve) with no stimulation is nearly parallel to the perfect performance line. With the first DBS sequence (solid curve), the performance dips a bit but then recovers and continues to score more successes than failures through the next series of trials with DBS either turned ON or OFF. At trial 550, the monkey began to alternate correct and incorrect responses so that the running score moved parallel to the horizontal axis. With the next DBS sequence, however, the monkey scored more correct than incorrect trials and then fell off dramatically when DBS was turned OFF. This pattern, a positive slope during DBS and a negative slope during DBS OFF, is seen along several segments of the running score curve. For all the DBS trials, the stimulation amplitude was 2 mA and the pulse frequency was 200 Hz. For almost all the trials, excluding those trials corresponding to the points on the curve centered on diamonds, the two deepest contacts on the caudal electrode were both set to be the cathodes and the two deepest on the rostral electrode were connected to the stimulator as the anodes for the double bipolar current. Other single bipolar current distributions were used on the other trials as shown in FIG. 12.

Two other measures of behavioral performance were used to evaluate the effectiveness of central thalamic DBS. In FIG. 13, the monkey's performance under various conditions of DBS for two behavioral recording sessions separated by more than 20 days is described by a state-space model (session 1, FIG. 13A; session 2, FIG. 13C) and plots of reaction-times (session 1, FIG. 13B, session 2, FIG. 13D). The state-space model fits the sequence of correct/incorrect responses across the trials of a session with a measure of performance that is influenced, in part, by trends in performance. See Smith et al., "A Bayesian Statistical Analysis of Behavioral Facilitation Associated with Deep Brain Stimulation," *J. Neurosci. Methods* 183(2):267-76 (2009), which is incorporated herein by reference in its entirety.

The state-space model permits an examination of the dynamics of task performance over the session; that is, it allows for an appreciation of the various trends that are provoked in the animal's performance by the parameters of the experiment, such as the presence or absence of DBS, the frequency of DBS stimulation, or changes in the size of the liquid reward. Task performance (dark) and 95% confidence intervals (lighter) for this measure are described by the smooth black curves in FIGS. 13A and 13C. The rectangular patches of grayscale demarcate trials for which DBS was applied to the central thalamus (green, 40 Hz; blue, 200 Hz) at the amplitudes indicated by the numbers running along the top of each state-space plot. The asterisks indicate which DBS trials used the multi-electrode configuration with a double bipolar field (cathodes in the caudal electrode). From FIGS. 13A and 13B, it is evident that DBS using the double bipolar field reliably improves performance.

Figure 13A:
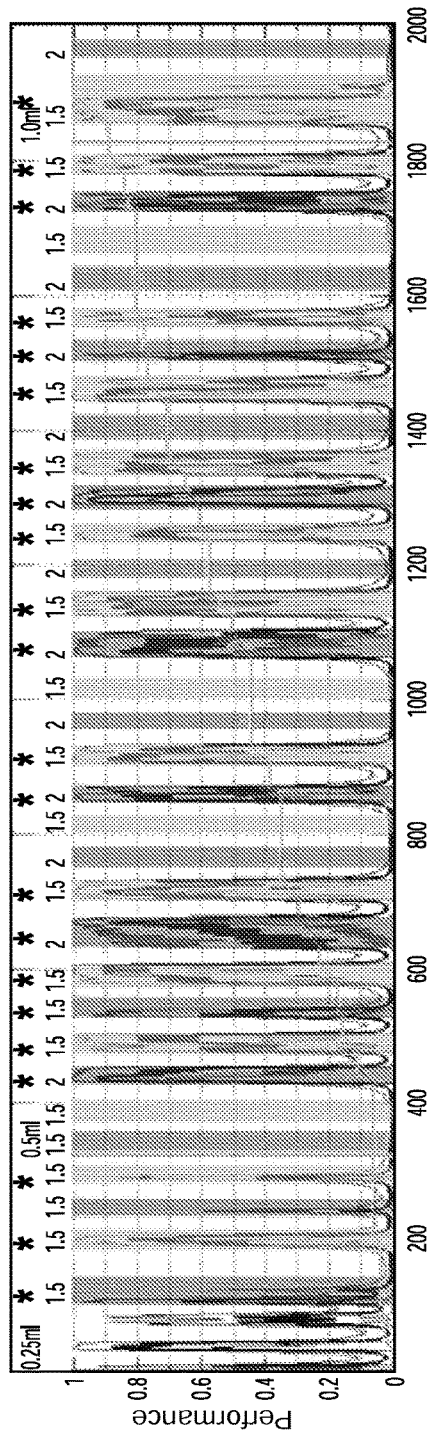
FIGS. 13A-13D illustrate graphs of a monkey's performance under various conditions of deep brain stimulation for two behavioral recording sessions separated by more than 20 days is described by a state-space model (session 1, FIG. 13A; session 2, FIG. 13C) and plots of reaction-times (session 1, FIG. 13B, session 2, FIG. 13D) for the behavioral test shown in FIG. 11.
Figure 13B:
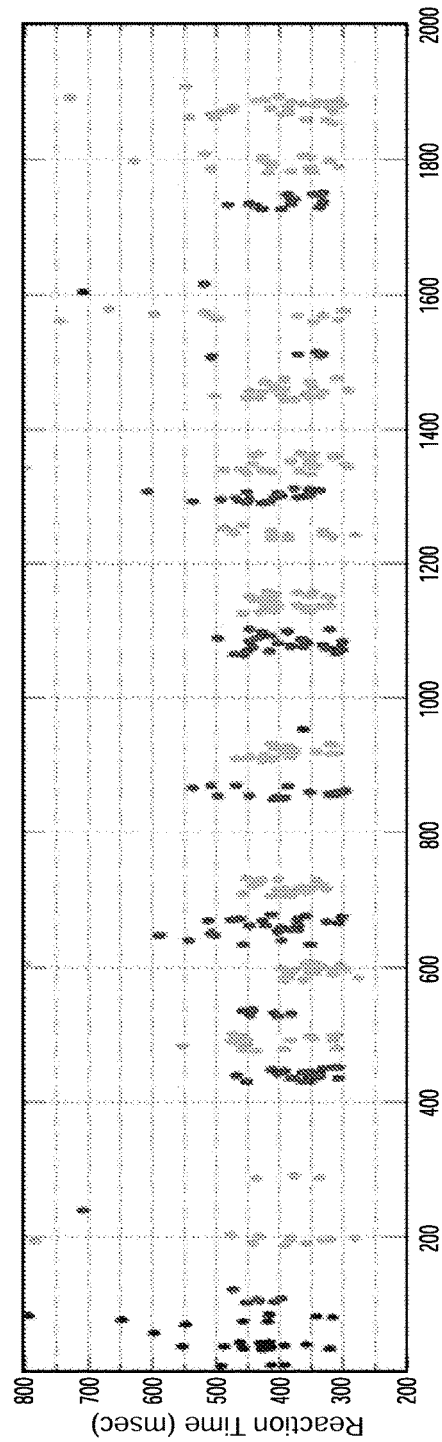
Figure 13C:
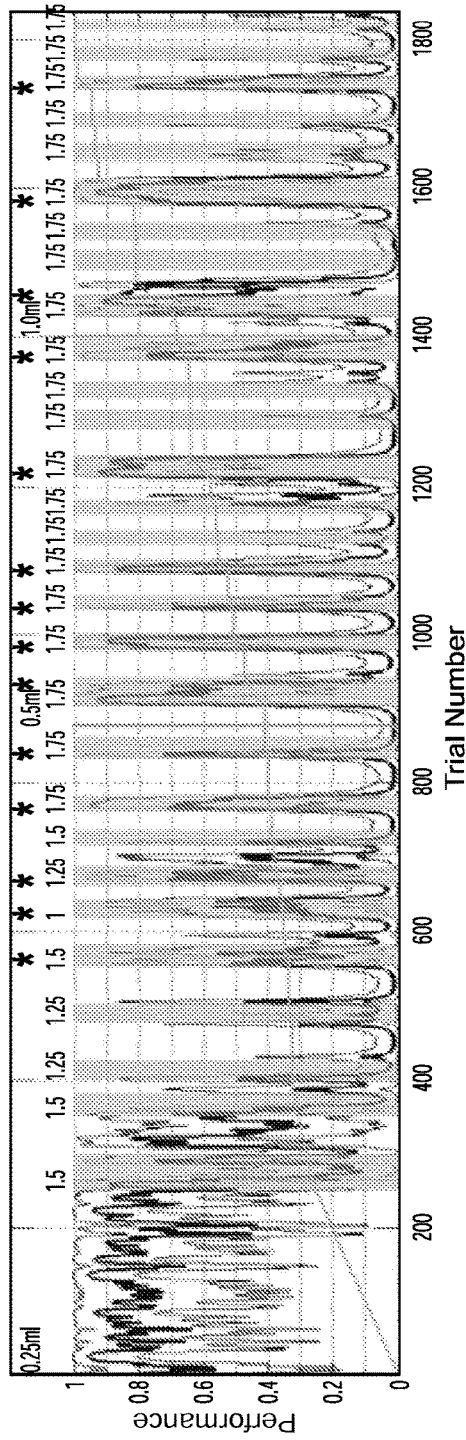
Figure 13D:
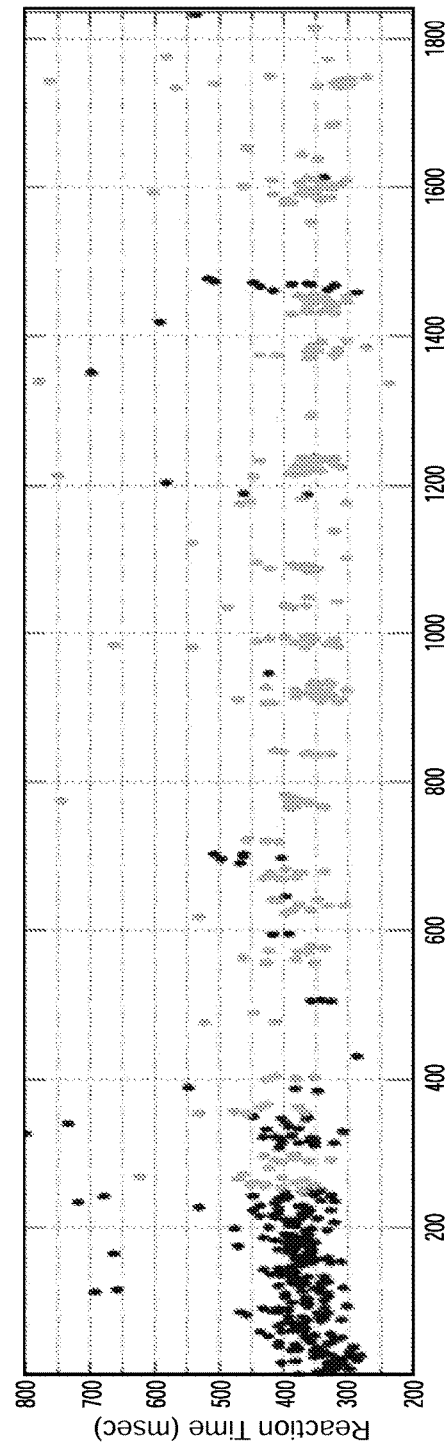

Reaction time data are shown for the two sessions in FIGS. 13B and 13D. Reaction times (bar releases at end of variable delay periods) are plotted as black dots for trials with no DBS, and as gray dots for 40 Hz and 200 Hz. Note that very few black dots appear in the reaction time plots once DBS commences during a session. This indicates that almost no bar releases were executed without the presence of DBS. In addition, while FIG. 13B demonstrates that both 40 Hz and 200 Hz DBS trails are associated with more behavioral responses than trials with no DBS, the reaction times for the DBS trials with 40 Hz trend to larger values than those trials utilizing 200 Hz.

As is seen with FIGS. 12 and 13A-13D, there are a number of behavioral performance measures that are available to evaluate the effectiveness of various DBS parameters. Adjusting pulse amplitude and frequency, as well as the structure of the bipolar fields of the DBS in the neural tissue, can have a dramatic effect on behavioral outcome.

Example 2

Impact of DBS on Neural Activity

Figure 14:
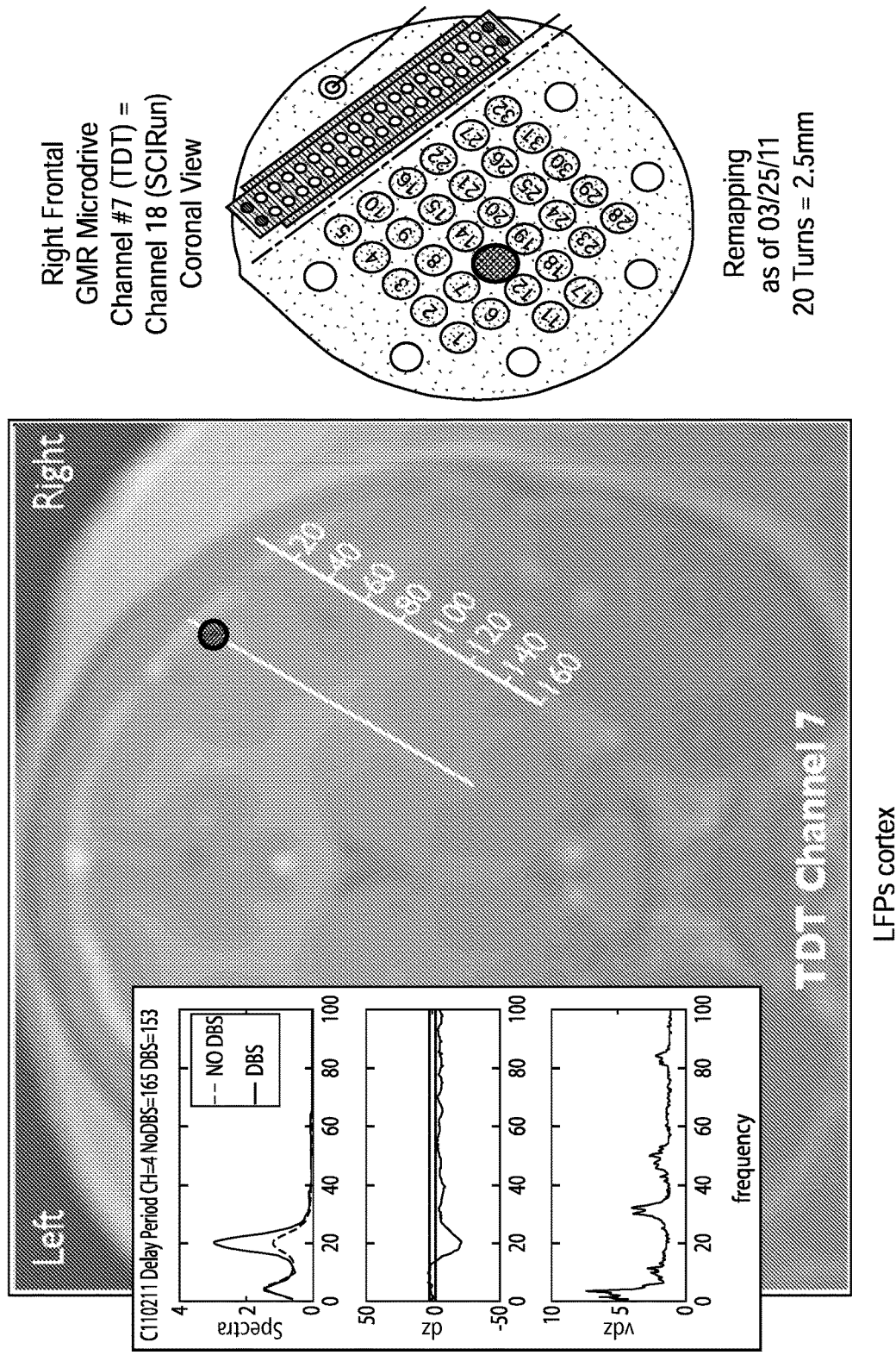
FIG. 14 illustrates local field potential activity recorded from a microelectrode advanced into the frontal cortex by the GMR Microdrive for the behavioral test shown in FIG. 11.
Figure 15:
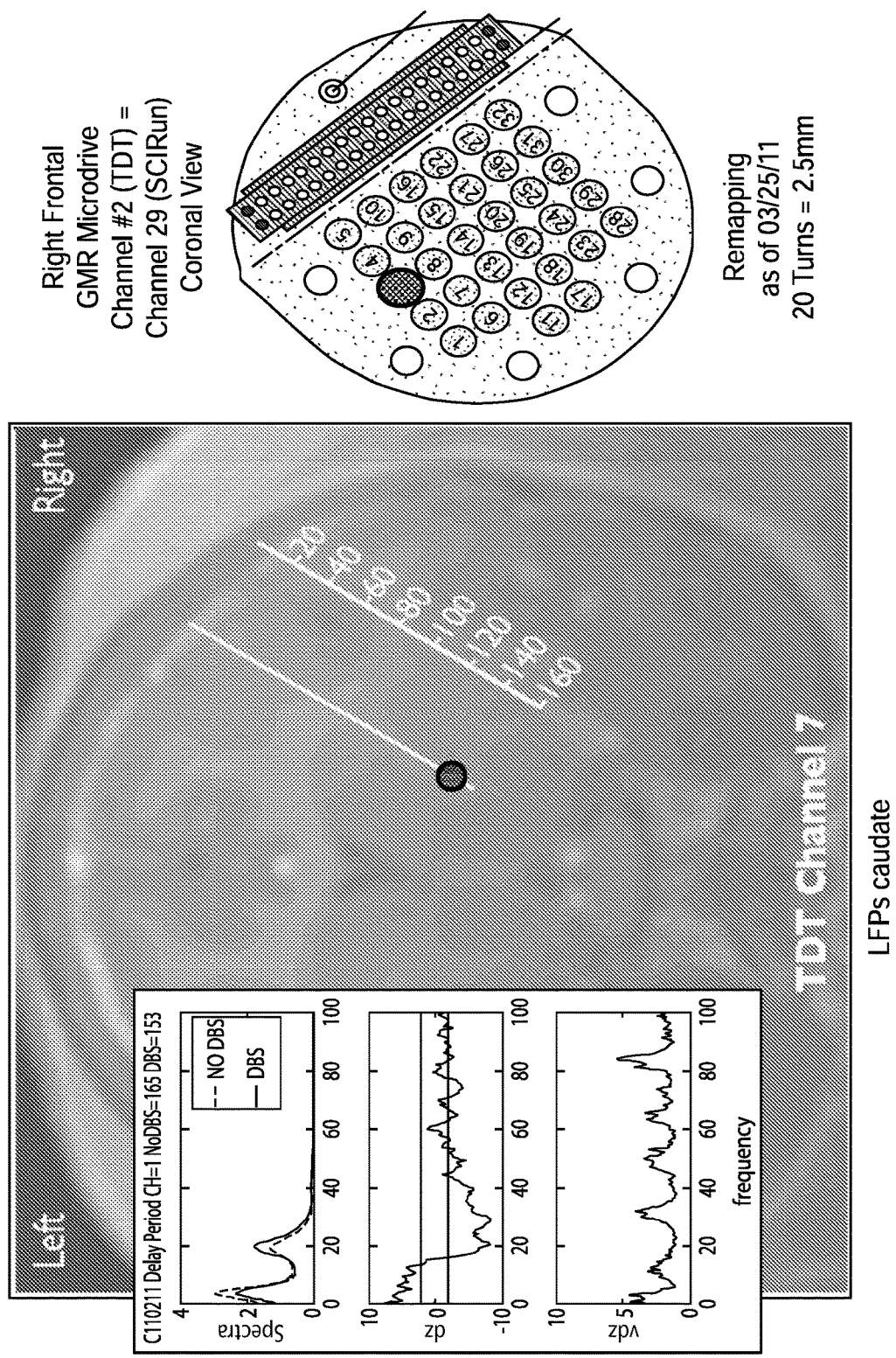
FIG. 15 illustrates local field potential activity recorded from a microelectrode advanced into the caudate by the GMR Microdrive for the behavioral test shown in FIG. 11.
Figure 16:
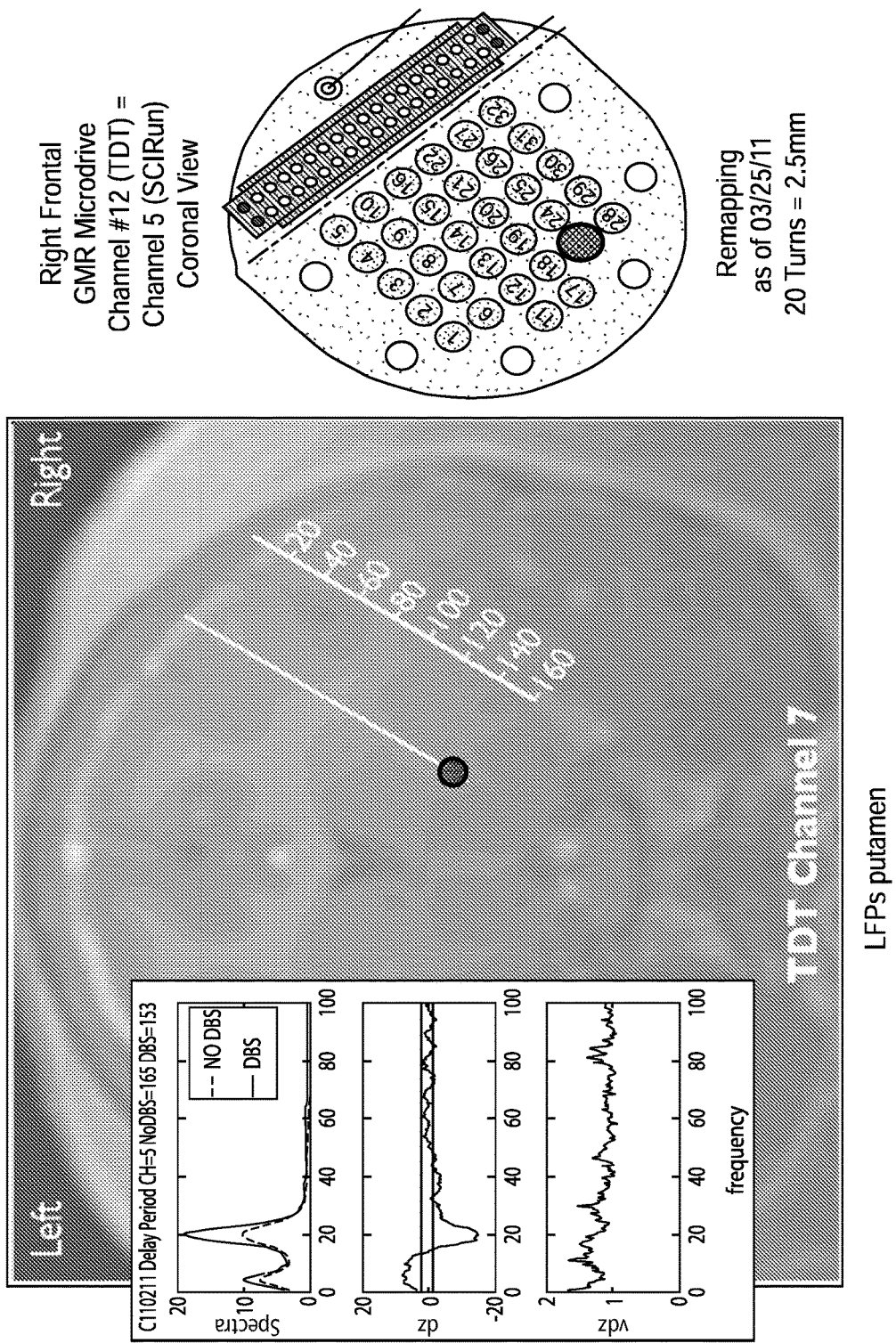
FIG. 16 illustrates local field potential activity recorded from a microelectrode advanced into the putamen by the GMR Microdrive for the behavioral test shown in FIG. 11.

Since central thalamic DBS is seen to have a reliable influence on the monkey's performance on sustained attention tasks, single-unit and local field potential recordings (LFPs) were analyzed to determine if DBS also produced a reliable change in neural activity during the delay periods of the tasks. Unit and local field potential activity from 140 recording sites within frontal areas 8 and 45, prefrontal areas 9 and 46 and within anterior dorsal portions of the caudate and putamen. The majority of unit recordings exhibited clear task-dependent modulation either during or flanking the delay period of the sustained attention task (task described in FIG. 11). The LFPs within these regions displayed significant peaks in power spectra calculated from the first second of the delay periods. These peaks appeared within the delta (0.5-4 Hz) and beta (15-30 Hz) bands of the power spectra. FIGS. 14-16 present the LFP activity recorded from three locations in the anterior forebrain and will illustrate the impact of DBS during the delay period of the sustained attention task.

FIG. 14 examines the LFP activity recorded from a microelectrode advanced into the frontal cortex (area 8A, frontal eye field) by the GMR microdrive. The position of the microelectrode in the microdrive grid is shown on the right. Here, for the grid, left is posterior, right is anterior, top is medial and the bottom is more ventral on the monkey's head. As one can see from the coronal MRI section aligned with the position of the recording channel, the microelectrode at this depth is located within the cortex situated between the superior arcuate sulcus and the principle sulcus. The scale aligned with the path of the microelectrode is marked in units of microdrive 'turns' (1 turn=125 microns). The inset shows the power spectrum of the delay period LFP activity both during DBS trials (solid curve) and during trials without DBS (dashed curve).

There are several features of the power spectra that are worth noting. There are obvious peaks in the spectra at both 4 Hz and at 20 Hz. When DBS is turned on, the beta peak (20 Hz) gains power whereas the delta peak (4 Hz) remains unchanged. The significance of the change in the LFP spectrum is determined by a z-score statistic (dz) that was developed for detecting ranges in the spectrum of a neural signal that differ under two experimental conditions. Bokil et al., "A Method for Detection and Classification of Events in Neural Activity," IEEE Trans. Biomed. Eng. 53(8):1678-87 (2006) (incorporated herein by reference in its entirety).

The values of dz are plotted in the second panel of the spectrum inset in FIG. 14 along with two horizontal lines that delimit the range around the dz=0 line that the statistic must exceed in order for the power spectral difference produced by two experimental conditions to be considered significant. As shown in FIG. 14, dz is significant in a range of frequencies centered on 20 Hz. The delta peak shows no significant change between the DBS-on and DBS-off conditions. The lower panel in the power spectrum inset, Vdz indicates how much of the variance in the difference of neural activity under the two experimental conditions can be accounted for by a difference in the power spectra alone. Values of Vdz that are greater than 1 indicate that the there is more correlation structure in the neural activity than can be captured by the autocorrelation function.

Similar plots of LFP changes during the delay periods are shown in FIG. 15 (caudate) and FIG. 16 (putamen). The neural activity illustrated in FIGS. 14-16 was all recorded simultaneously. Unlike the cortical activity seen during this behavioral recording session, however, DBS produced a significant suppression of the delta band power while also increasing the power in the beta band in the striatum.

Figure 17:
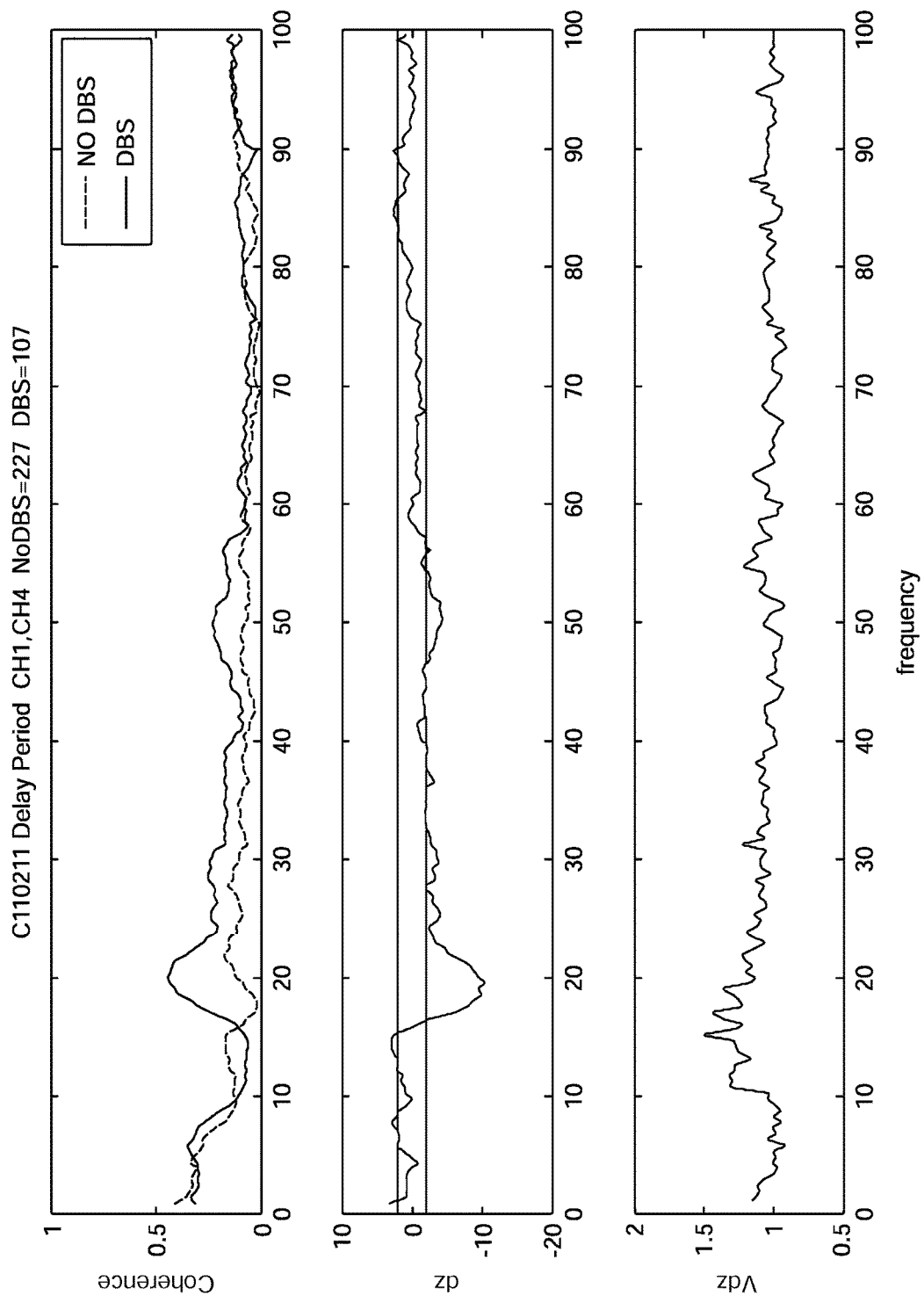
FIG. 17 illustrates test results showing Caudate Cortex Coherence Delay Period for the behavioral test shown in FIG. 11.
Figure 18:
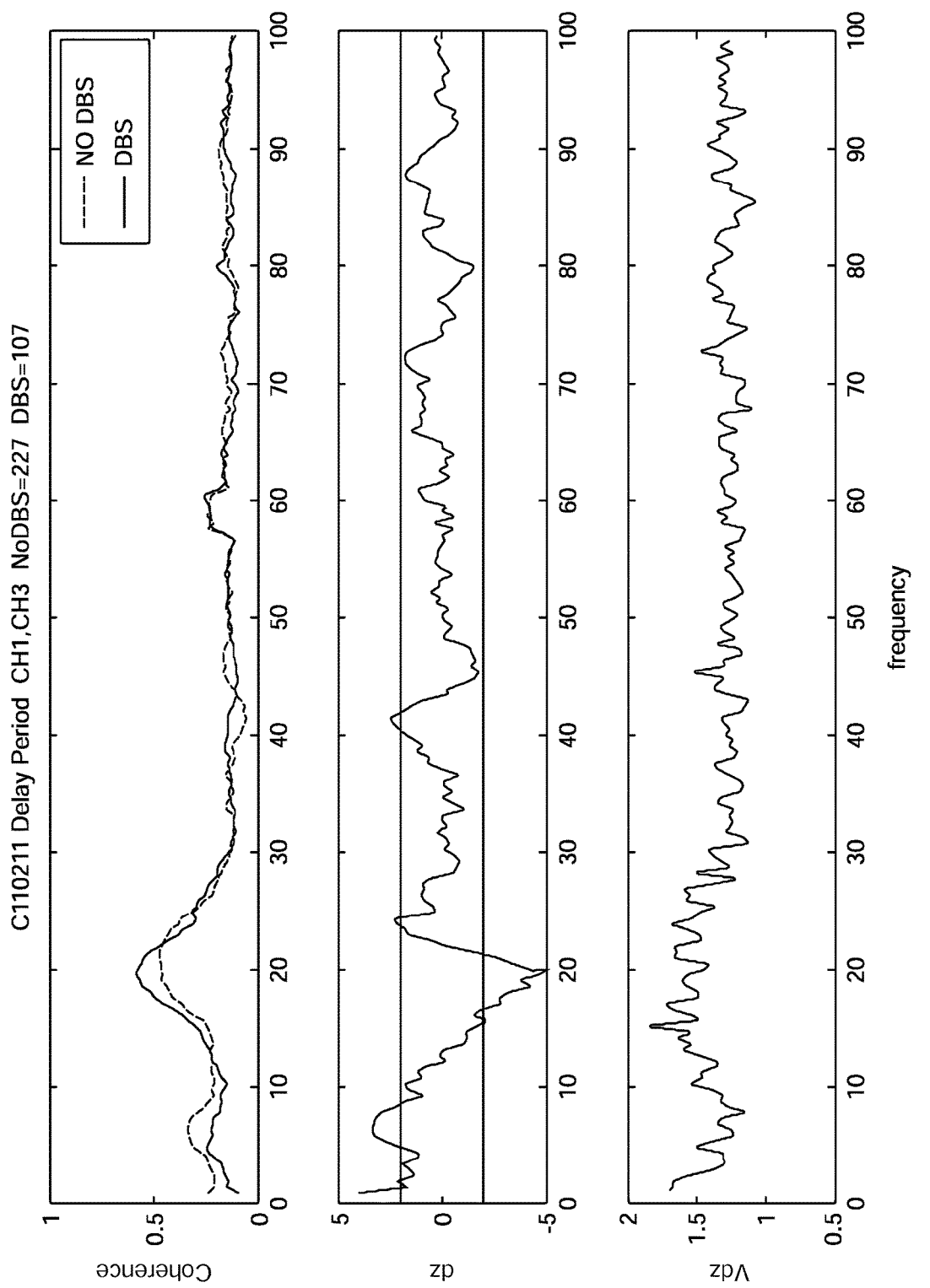
FIG. 18 illustrates test results showing Caudate Putamen Coherence Delay Period for the behavioral test shown in FIG. 11.
Figure 19:
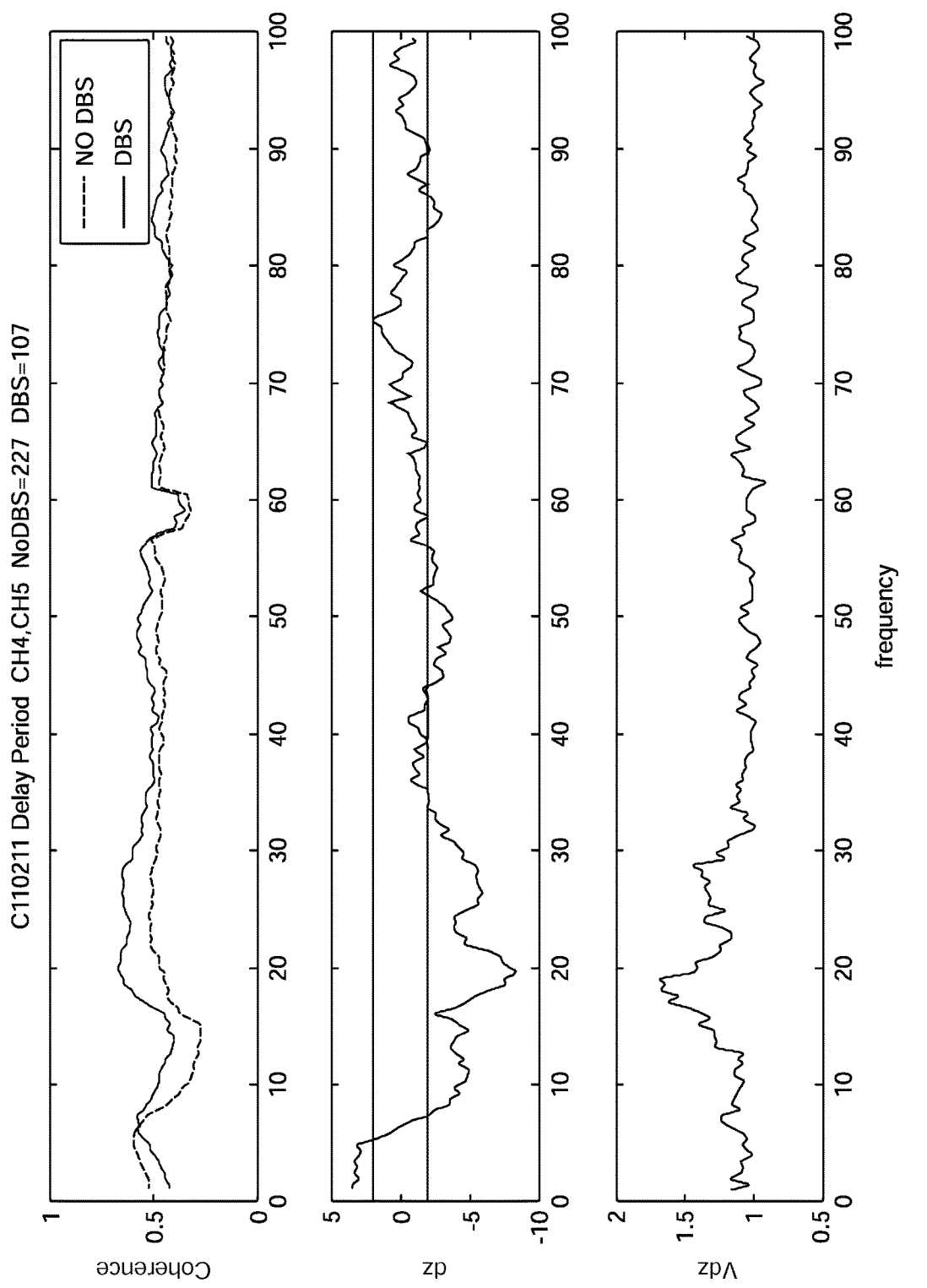
FIG. 19 illustrates test results showing Cortex Putamen Coherence Delay Period for the behavioral test shown in FIG. 11.

Another method for analyzing the impact of DBS on neural activity in the behaving monkey is to evaluate the coherence between the LFPs recorded simultaneously from different microelectrodes in the anterior forebrain. FIGS. 17-19 illustrate the coherence between three pairs of recording sites. Changes in LFP activity with DBS at each of the individual sites are illustrated in FIGS. 14-16. Coherence is a frequency domain measure of correlated activity. High values of coherence (values at 1 or close to 1) indicate that the two neural signals track each other's fluctuations in amplitude and timing. Low values of coherence (close to 0) indicate that the two neural signals are independent. The top row of each of FIGS. 17-19 presents the coherence for pairs of LFP signals recorded during the delay periods from the cortex and putamen (FIG. 19), cortex and caudate (FIG. 17) and the putamen and caudate (FIG. 18). The coherence for delay periods from DBS trials and the coherence from trials without DBS are each indicated by arrows. Note that in general, the coherence values fluctuation at values around or below 0.5 across the range of the spectrum plotted here, and that the presence or absence of DBS appears to have a somewhat restricted impact on the coherence. The cortex/putamen coherence (FIG. 19) demonstrates a broad frequency band of enhanced synchronized activity between the two brain regions centered at 20 Hz during correct trials when DBS in the central thalamus was switched ON. The significant enhanced coherence during DBS is more narrowly focused at 20 Hz for the caudate/cortex LFP pair recordings (FIG. 17), and the change in synchronization produced by DBS for the caudate/putamen pair recording (FIG. 18) more closely follows the changes in power the LFP recordings (enhancement at 20 Hz, suppression at 4 Hz) described above for the non-paired LFP recordings from the anterior forebrain (FIGS. 14-16). The impact of DBS on the coherence becomes more apparent when one examines the dz score for each coherence measure.

In the second row of each of FIGS. 17-19, dz is plotted for the three LFP recording pairs. As with FIGS. 14-16, the horizontal lines surrounding dz=0 give the 95% confidence interval for the dz score. Frequencies at which dz lies either above or below the interval are regions in the spectrum that are significantly influenced by DBS. For the cortex/putamen pair, DBS suppresses coherence at 10 Hz and below, yet increases the coherent activity above 10 Hz up to frequencies just below 40 Hz. The decrease in coherence below 10 Hz seen in the cortex/caudate LFP pair recording is not significant but the increase in beta-band coherence produced by DBS reaches values similar to the increase seen in the cortex/putamen LFP pair recording. Finally, the influence of DBS on the putamen/caudate LFP pair recording appears to be more restricted to a narrow band centered on 40 Hz. Activity in the caudate and putamen appears to track in a relatively narrow band of frequencies with DBS appears to suppress somewhat this coherent activity at low frequencies and enhance it at 20 Hz.

Central thalamic deep brain stimulation has been proposed as a therapeutic strategy to remediate impaired consciousness following severe brain injury. See Schiff et al., "The Role of Arousal and "Gating" Systems in the Neurology of Impaired Consciousness," *J. Clinical Neurophysiology* 17(5):438-52 (2000) and Schiff et al., "Towards a Neurophysiological Foundation for Cognitive Neuromodulation Through Deep Brain Stimulation," *Thalamus and RS* 2, 55-69. (2002), which are hereby incorporated by reference in their entirety. Disruptions within the frontal-striatal-thalamic network, specifically involving the central thalamus, lead to marked disturbances in normal cognitive function, which can be partially ameliorated through pharmacological interventions as disclosed in Williams et al., "Thalamic Activity in Stupor," *Brain.* 74(4):377-98 (2009), which is incorporated by reference, and deep brain stimulation within the central thalamus as disclosed in Schiff et al., "Behavioural Improvements with Thalamic Stimulation After Severe Traumatic Brain Injury," *Nature* 448(7153):600-3 (2007), which is hereby incorporated by reference in its entirety. However, the specific physiological mechanism(s) enabling CTDBS to provide therapeutic value are unknown. Therefore, the goal of this study was two-fold, to explore the vast CTDBS parameter space (frequency, amplitude, and electrode contact geometry) within the intact non-human primate and to characterize large-scale neuronal activity recorded simultaneously within key regions of the frontal-striatal-thalamic network while the animals performed a series of goal-directed behavioral tasks.

Example 3

Additional Monkey Data

Figure 20A:
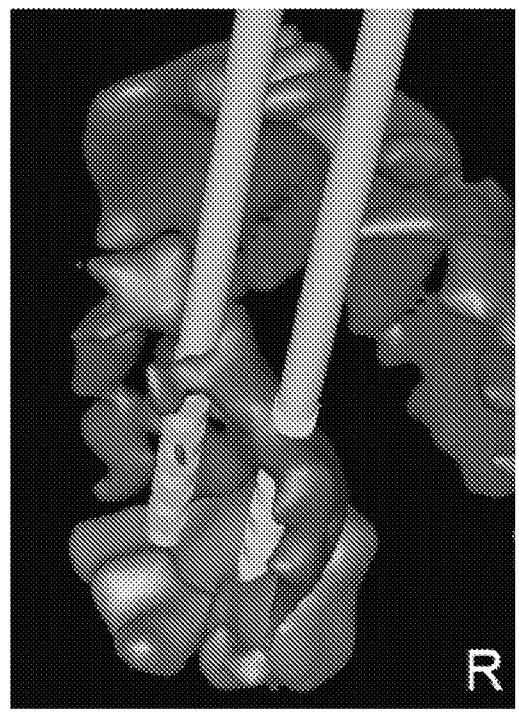
FIGS. 20A-20B are model reconstructions of the deep brain stimulator apparatus electrode positions.
Figure 20B:
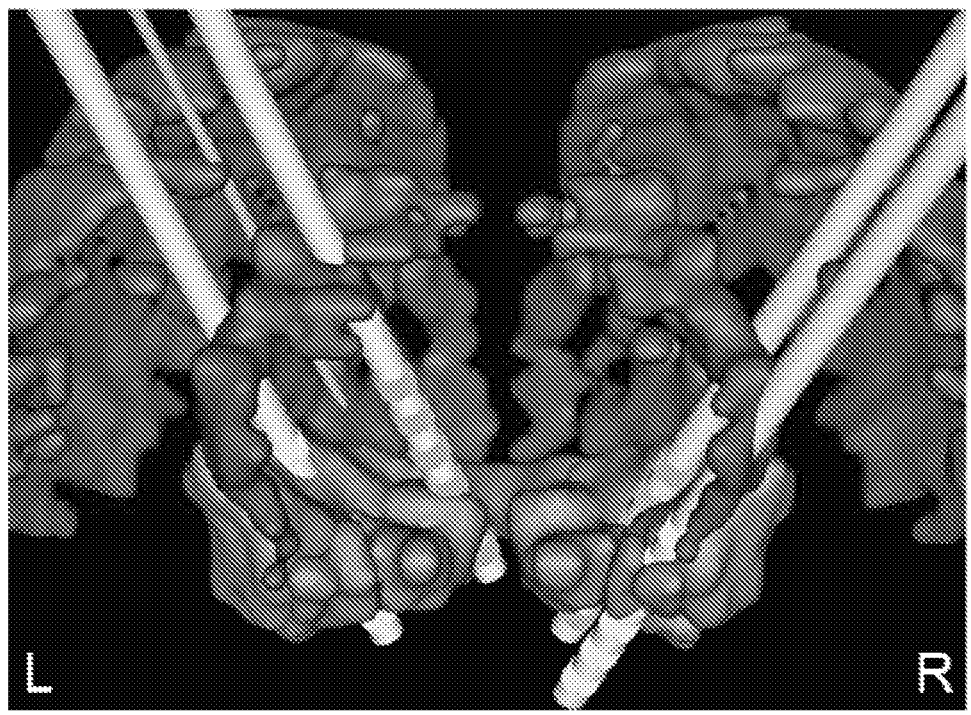

Model reconstruction of the DBS electrode positions are shown in FIGS. 20A and 20B. FIG. 20A shows the electrodes within the right central thalamus of the first animal. FIG. 20B shows the electrodes bilaterally in the second animal. The central thalamic nuclei and reticular nuclei are shown in relation to the DBS electrodes. Multiple 6-contact DBS electrodes coated with BT DOT (Biotectix, LLC, Ann Arbor, Mich.) were implanted within the central thalami of two animals. Each animal was implanted with multiple Gray Matter Research, LLC recording chambers and devices and a custom EEG array in order to investigate interactions among large cellular populations within the central thalamus, dorsal striatum, prefrontal cortex, and broadly across the cerebral hemispheres using EEG. A current-controlled charge-balanced asymmetrical biphasic waveform, varying in amplitude and frequency was delivered continuously during blocks of trials while the animals performed a series of visual-motor behavioral tasks.

Vigilance Task and Memory Task

Figure 21:
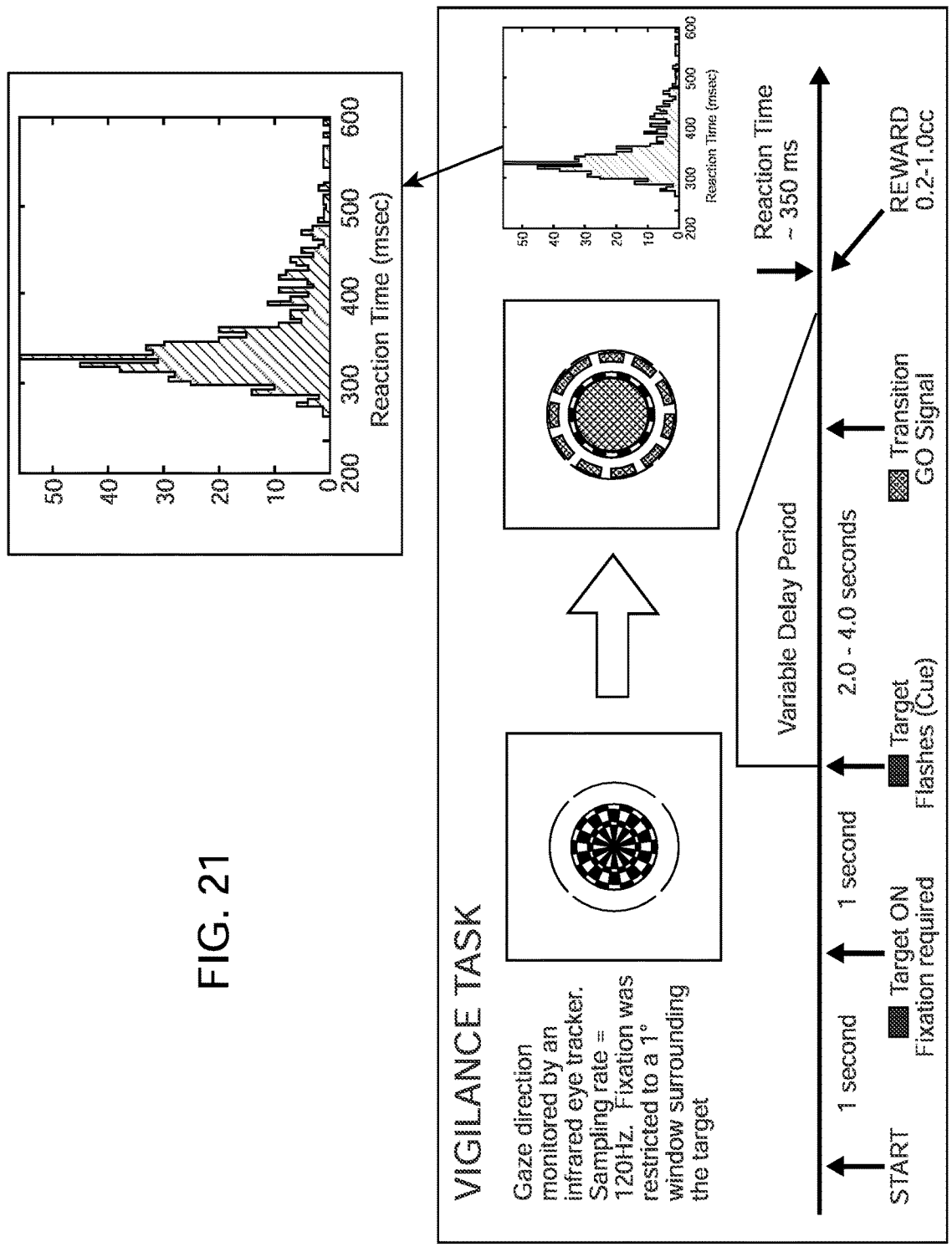
FIG. 21 illustrates a Vigilance task related to Example 3.

In the Vigilance Task, as shown in FIG. 21, gaze direction was monitored by an infrared eye tracker. Sampling rate=120 Hz. Fixation was restricted to a 1° window surrounding the target.

Figure 22:
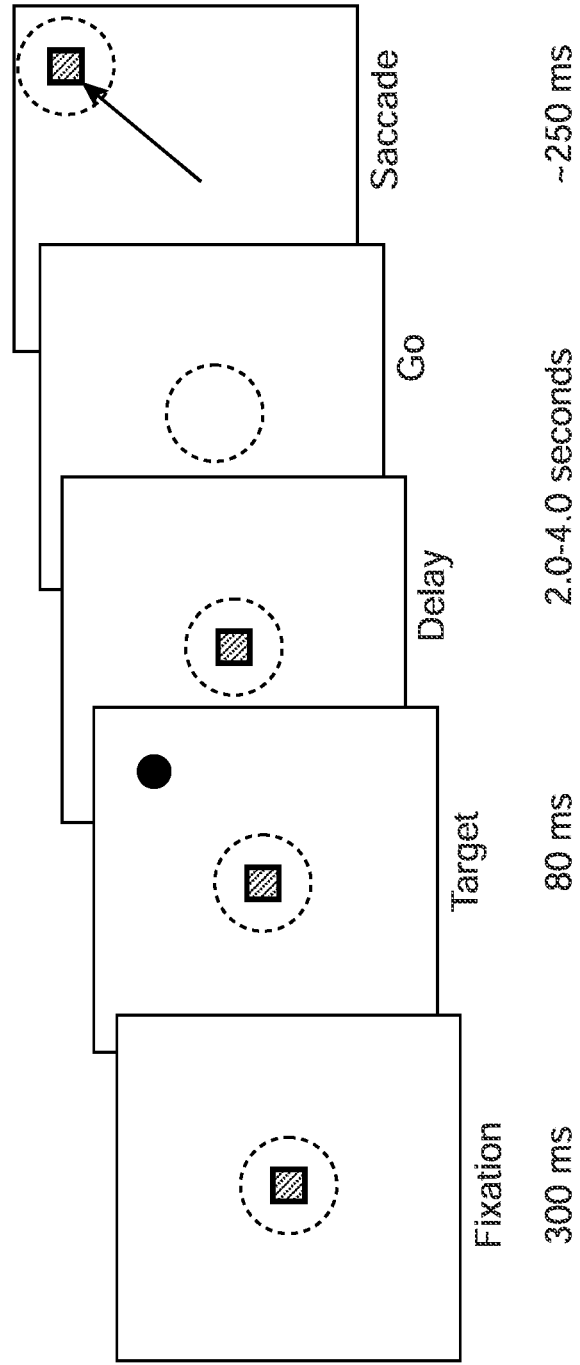
FIG. 22 illustrates a Memory task related to Example 3.

A checkerboard object appeared in 1 of 9 locations on the screen. The animal must hold fixation on the target for 1 second to start of the variable delay period. Delay period was signaled by a reverse contrast flicker of the object at 10 Hz, lasting on average 3 seconds (SD of 250 ms). When the checkerboard object changed to the transition (GO signal), the animal had to touch a bar or IR switch within 250-800 ms following the GO signal. Performance varied greatly across the experimental session(s) and average peak performance ranged between 70-90% correct. A Memory task, as illustrated in FIG. 22 was also performed.

Figure 23A:
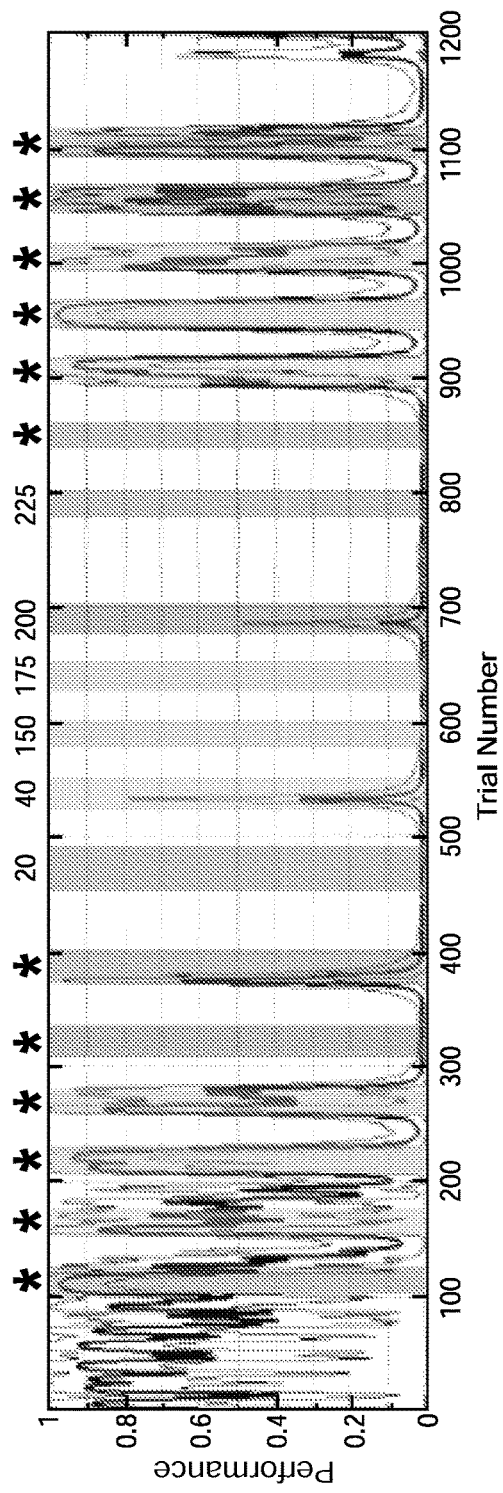
FIGS. 23A-23F illustrate test results of performance during three behavioral sessions.
Figure 23B:
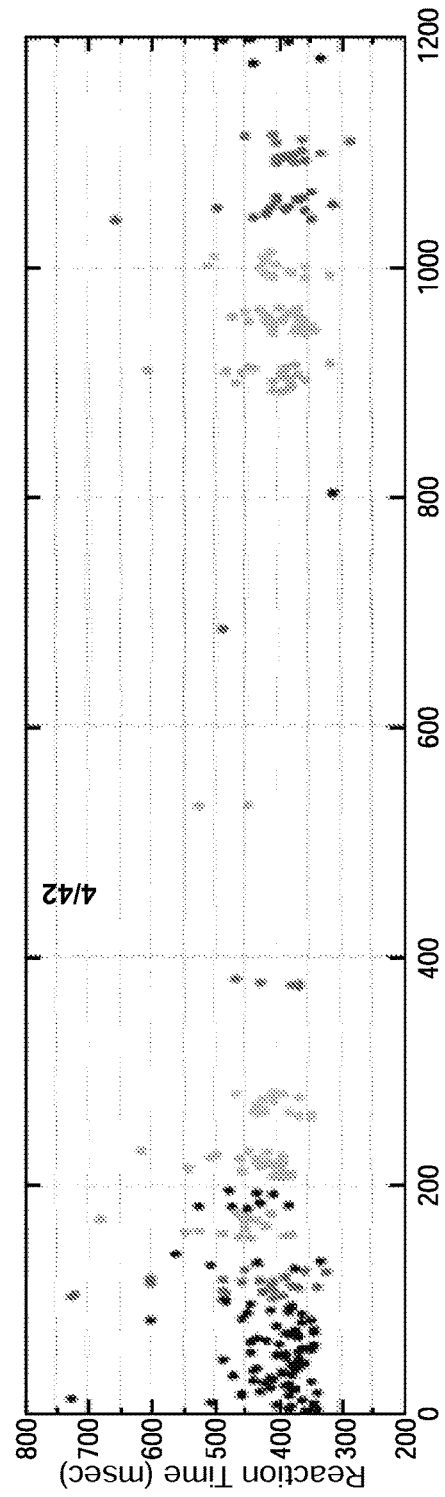
Figure 23C:
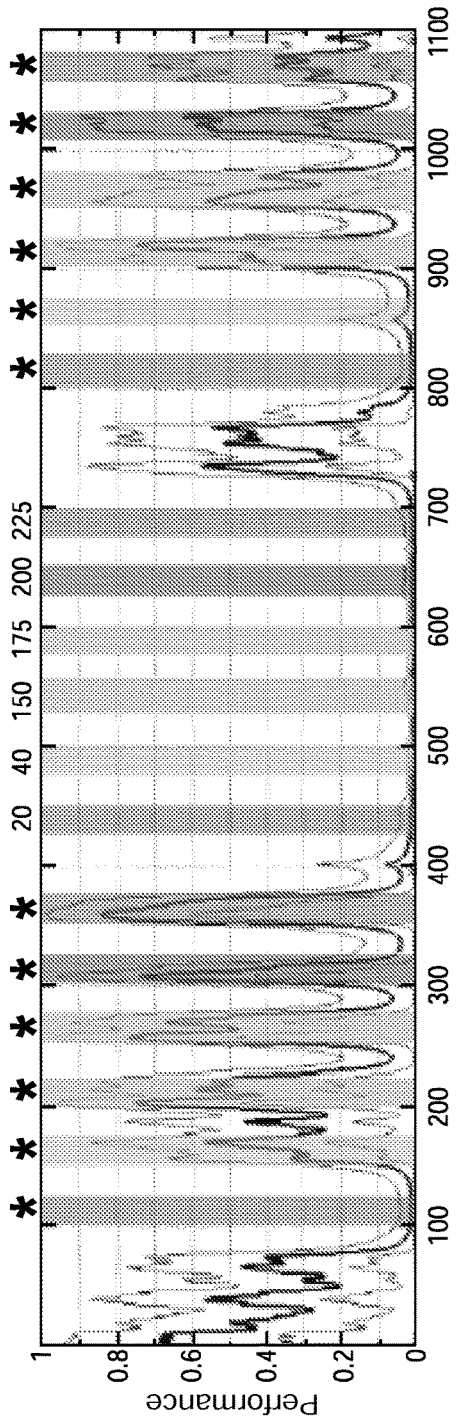
Figure 23D:
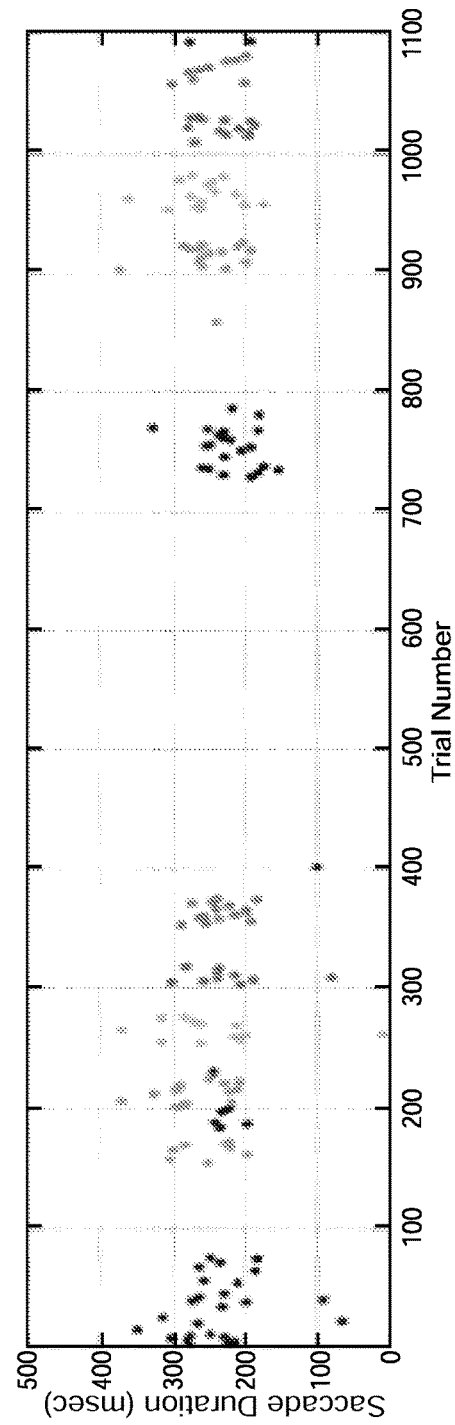
Figure 23E:
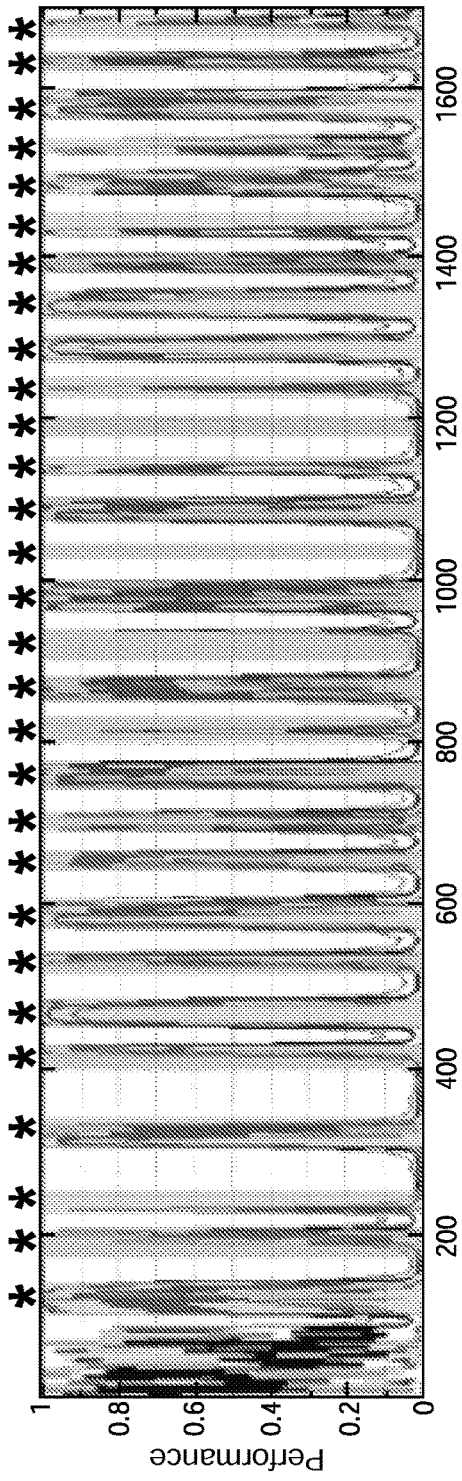
Figure 23F:
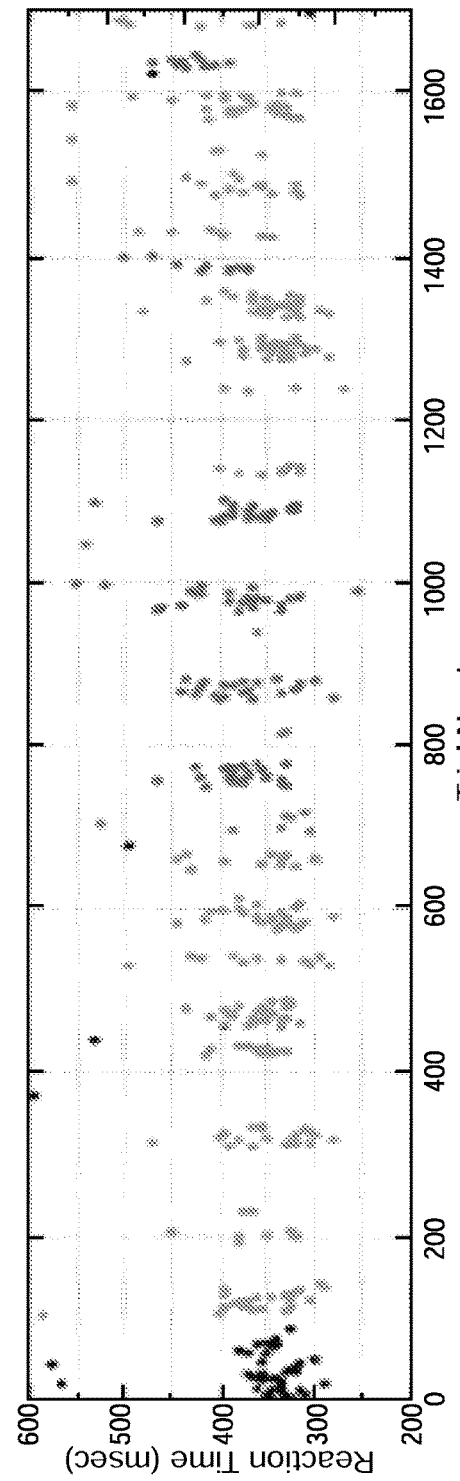
Figure 24A:
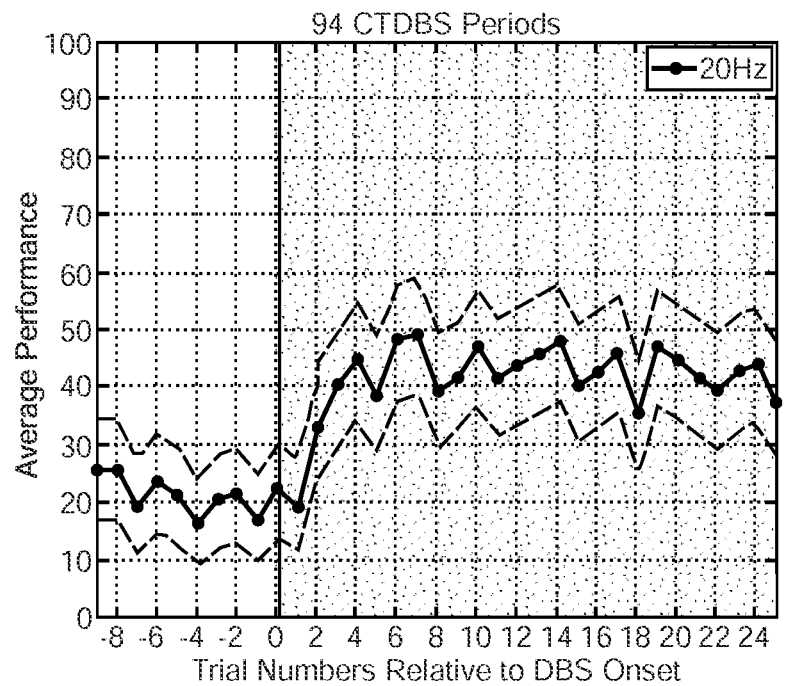
FIGS. 24A-24F illustrate test results showing average correct performance before and during 'Effective' central thalamus deep brain stimulation. All plots illustrate the first animal's average performance ten trials prior to central thalamus deep brain stimulation onset and average performance during stimulation at 20 Hz (FIG. 24A), 40 Hz (FIG. 24B), 150 Hz (FIG. 24C), 175 Hz (FIG. 24D), 200 Hz (FIG. 24E), and 225 Hz (FIG. 24F), for all tasks combined. Trials with stimulation amplitudes of 1.0 to 2.5 mA are combined in this analysis. The total number of central thalamus deep brain stimulation periods are noted above each plot.
Figure 24B:
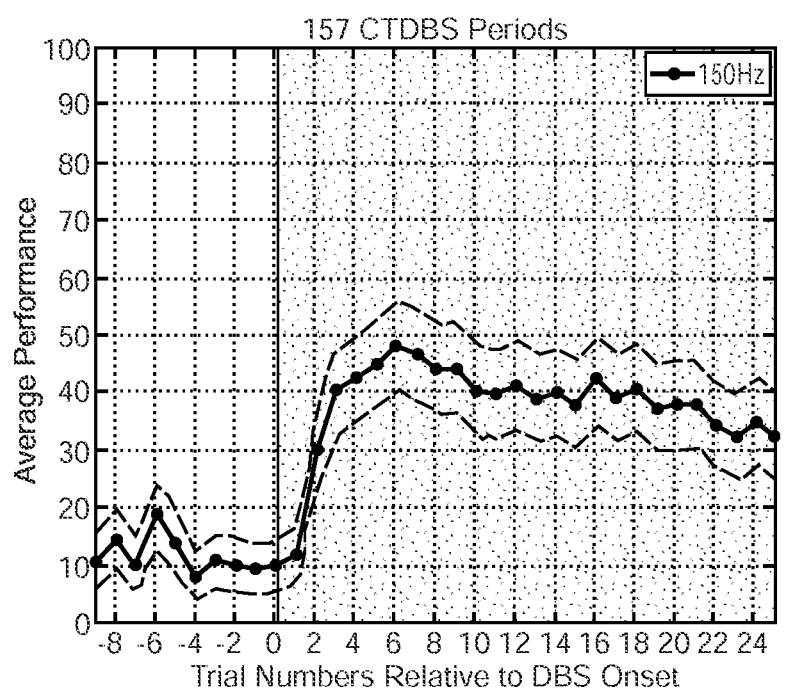
Figure 24C:
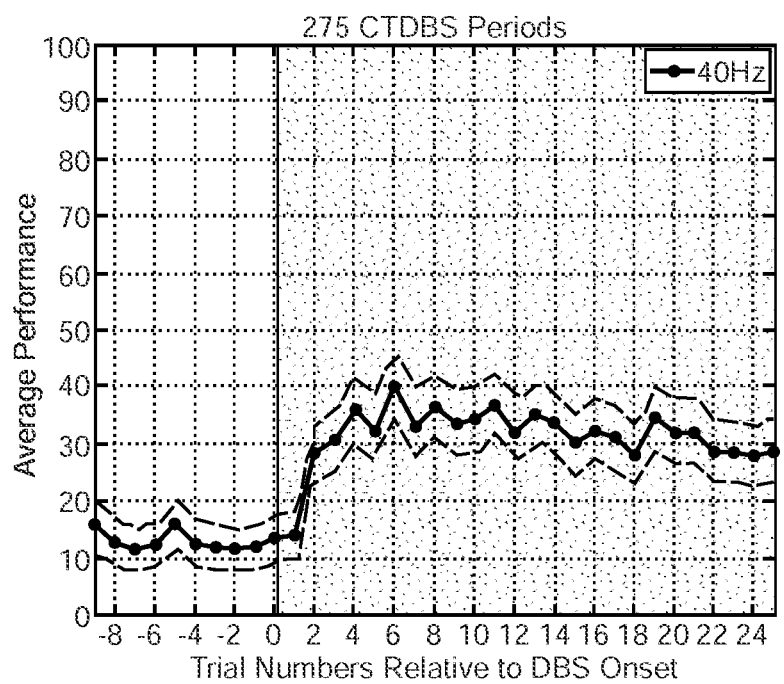
Figure 24D:
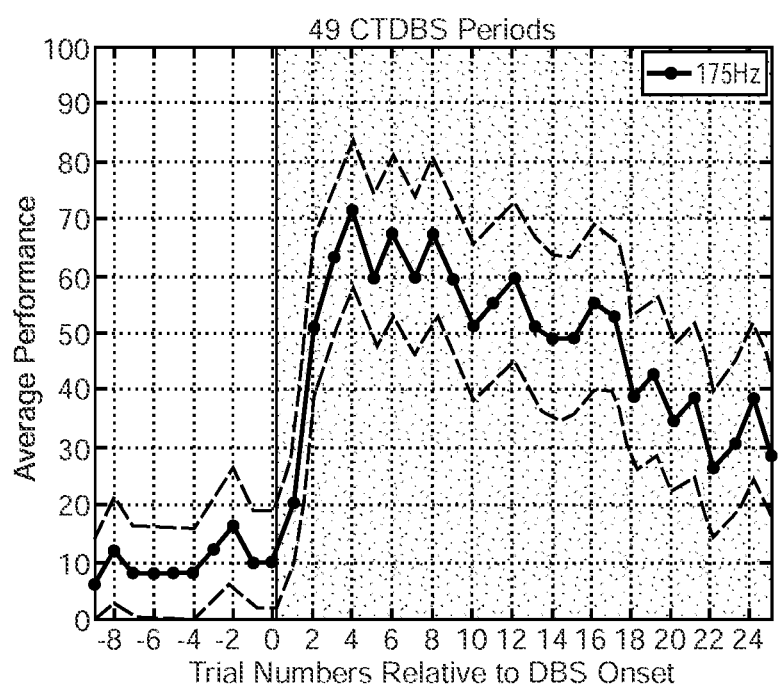
Figure 24E:
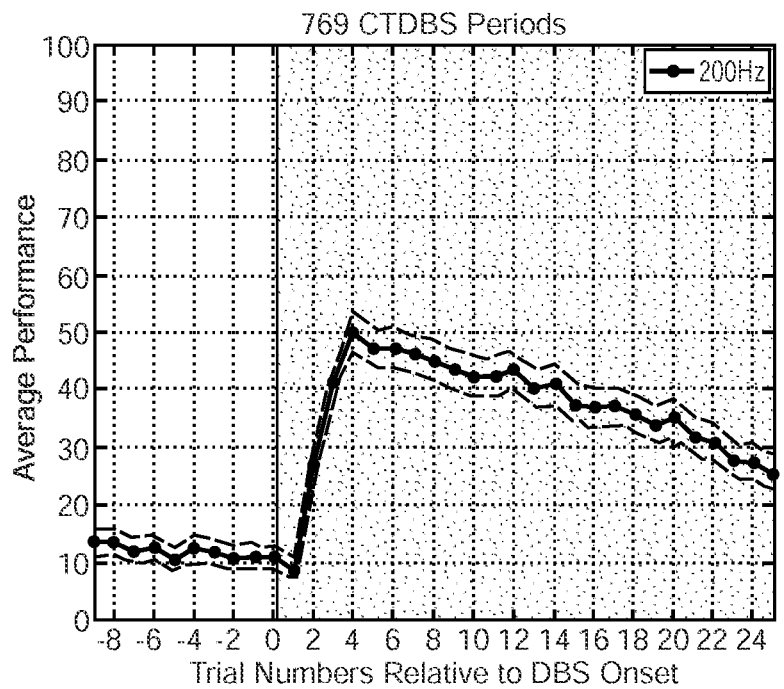
Figure 24F:
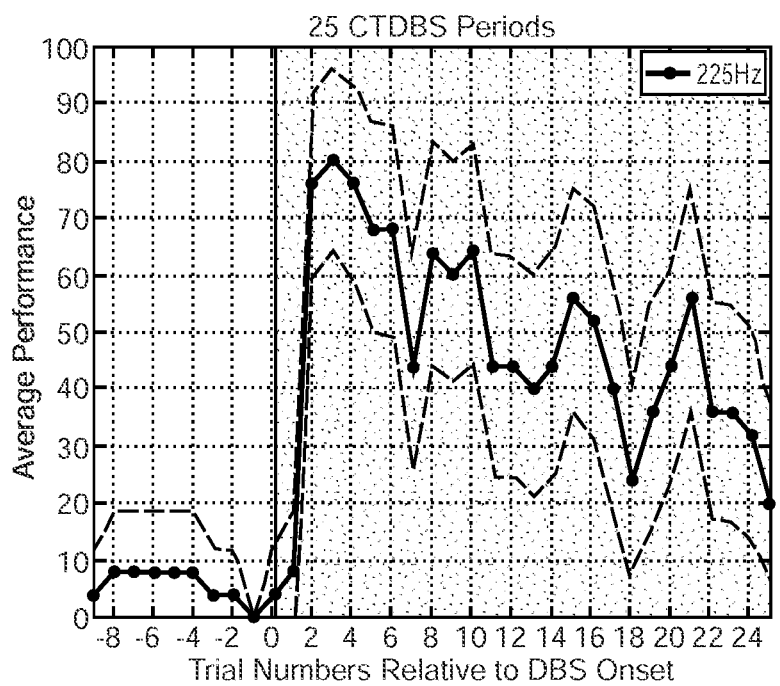

Performance during three behavioral sessions is shown in FIGS. 23A-23F. FIG. 23A shows the first animal's performance during the Vigilance task. The thick black line and 95% CI represents the performance profile derived from the State-Space Model (Smith et al., "A Bayesian Statistical Analysis of Behavioral Facilitation Associated with Deep Brain Stimulation," *J. Neurosci. Methods* 183(2):267-76 (2009), which is hereby incorporated by reference in its entirety), which highlights the causal linkage between periods of continuous CTDBS and performance fluctuations during a session containing 1200 continuous trials. The different shaded bars represent blocks of current-controlled 20 Hz, 40 Hz, 150 Hz, 175 Hz, 200 Hz, and 225 Hz CTDBS. "Effective" cathode/anode configurations are highlighted with an asterisk. FIG. 23B shows reaction times plotted as a function of trial number. Black points represent reactions times during CTDBS OFF periods and gray points represent CTDBS ON periods. FIGS. 23C and 23D show the animal's performance and reaction times during a session of the Memory Guided Saccade task. FIGS. 23E and 23F show the first animal's performance and reaction times during a Vigilance task session where CTDBS amplitude and electrode geometry were fixed during the 1700 trials.

FIGS. 24A-24F show average correct performance before and during 'Effective' CTDBS. All plots illustrate the first animal's average performance 10 trials prior to CTDBS onset and average performance during stimulation at 20 Hz (FIG. 24A), 40 Hz (FIG. 24B), 150 Hz (FIG. 24C), 175 Hz (FIG. 24D), 200 Hz (FIG. 24E), and 225 Hz (FIG. 24F) for all tasks combined. Trials with stimulation amplitudes of 1.0 to 2.5 mA are combined in this analysis. The total number of CTDBS periods are noted above each plot.

Figure 25A:
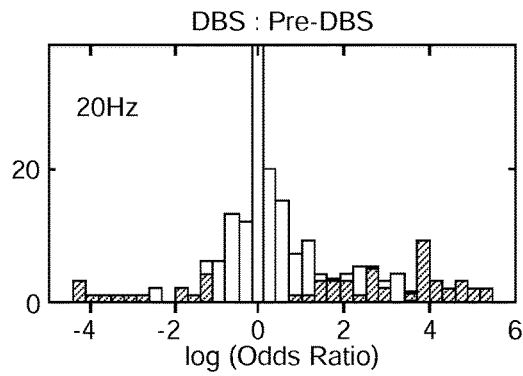
FIGS. 25A-25L illustrate quantifying behavioral modulation during central thalamus deep brain stimulation.
Figure 25B:
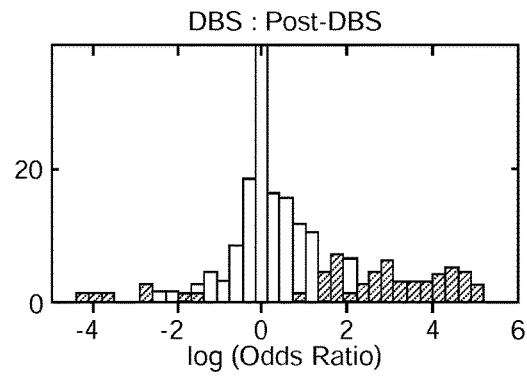
Figure 25C:
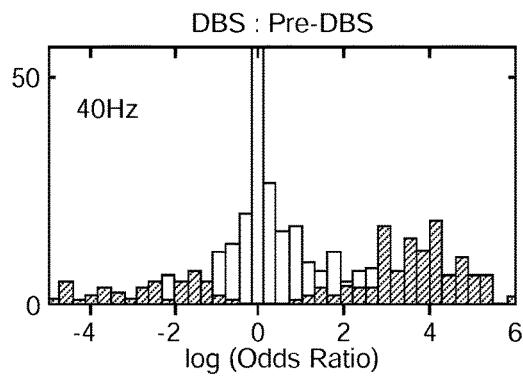
Figure 25D:
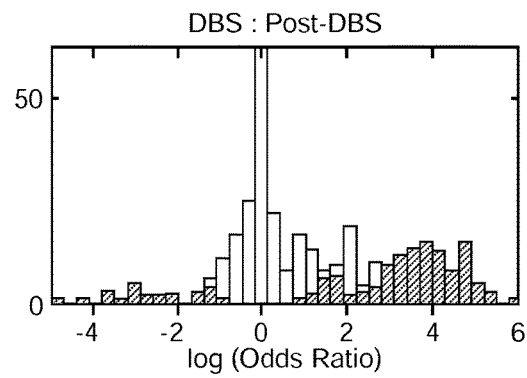
Figure 25E:
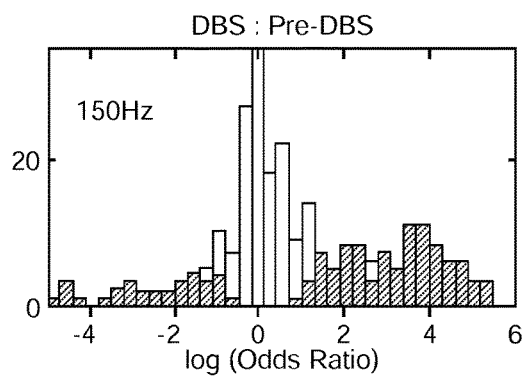
Figure 25F:
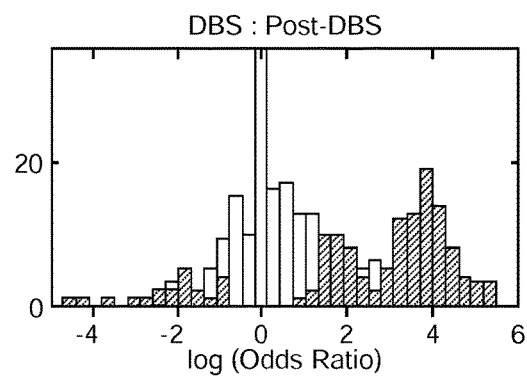
Figure 25G:
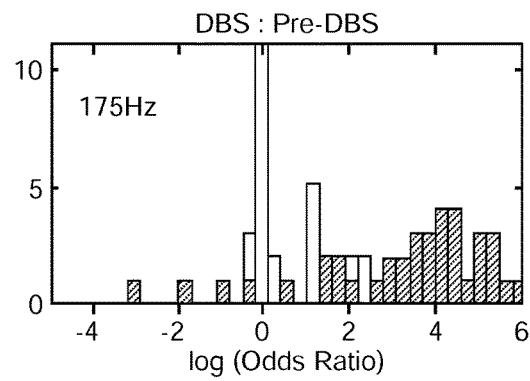
Figure 25H:
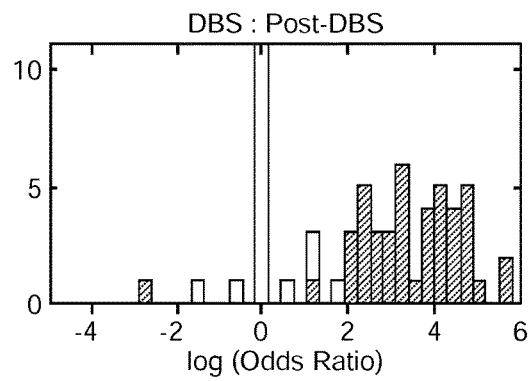
Figure 25I:
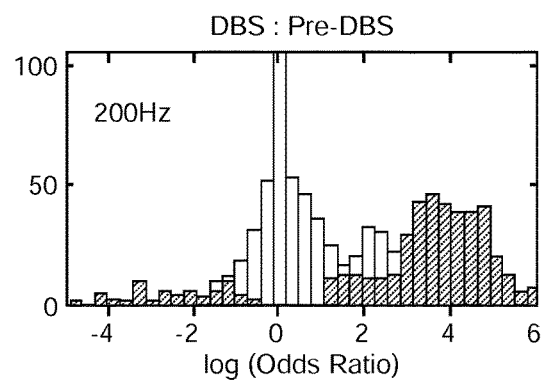
Figure 25J:
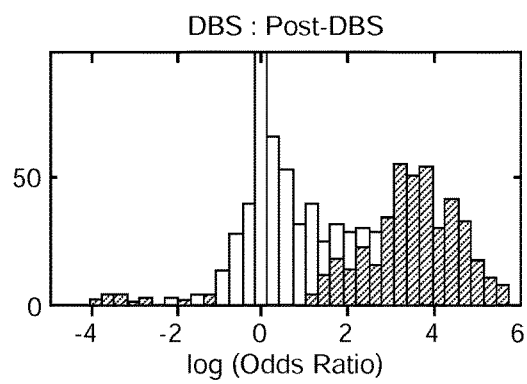
Figure 25K:
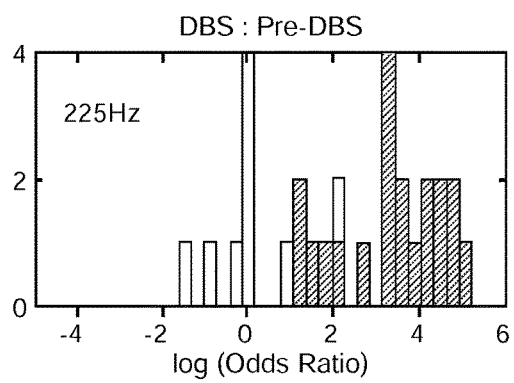
Figure 25L:
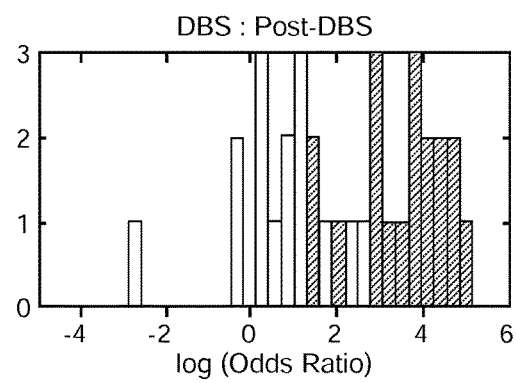

FIGS. 25A-25L illustrate quantifying behavioral modulation during central thalamus deep brain stimulation. FIGS. 25A, C, E, G, I, and K illustrate the distribution of Log Odds Ratios ("LOR") of performance (correct vs. incorrect) comparing performance during central thalamus deep brain stimulation/performance prior to central thalamus deep brain stimulation at 20 Hz, 40 Hz, 150 Hz, 175 Hz, 200 Hz, and 225 Hz, respectively. FIGS. 25 B, D, F, H, J, and L illustrate the distribution of LOR of performance comparing performance during central thalamus deep brain stimulation/performance following central thalamus deep brain stimulation at 20 Hz, 40 Hz, 150 Hz, 175 Hz, 200 Hz, and 225 Hz, respectively. All amplitudes, frequencies and electrode configurations are included (N=2007) from a total of 212 central thalamus deep brain stimulation sessions.

Figures 26A, 26B:
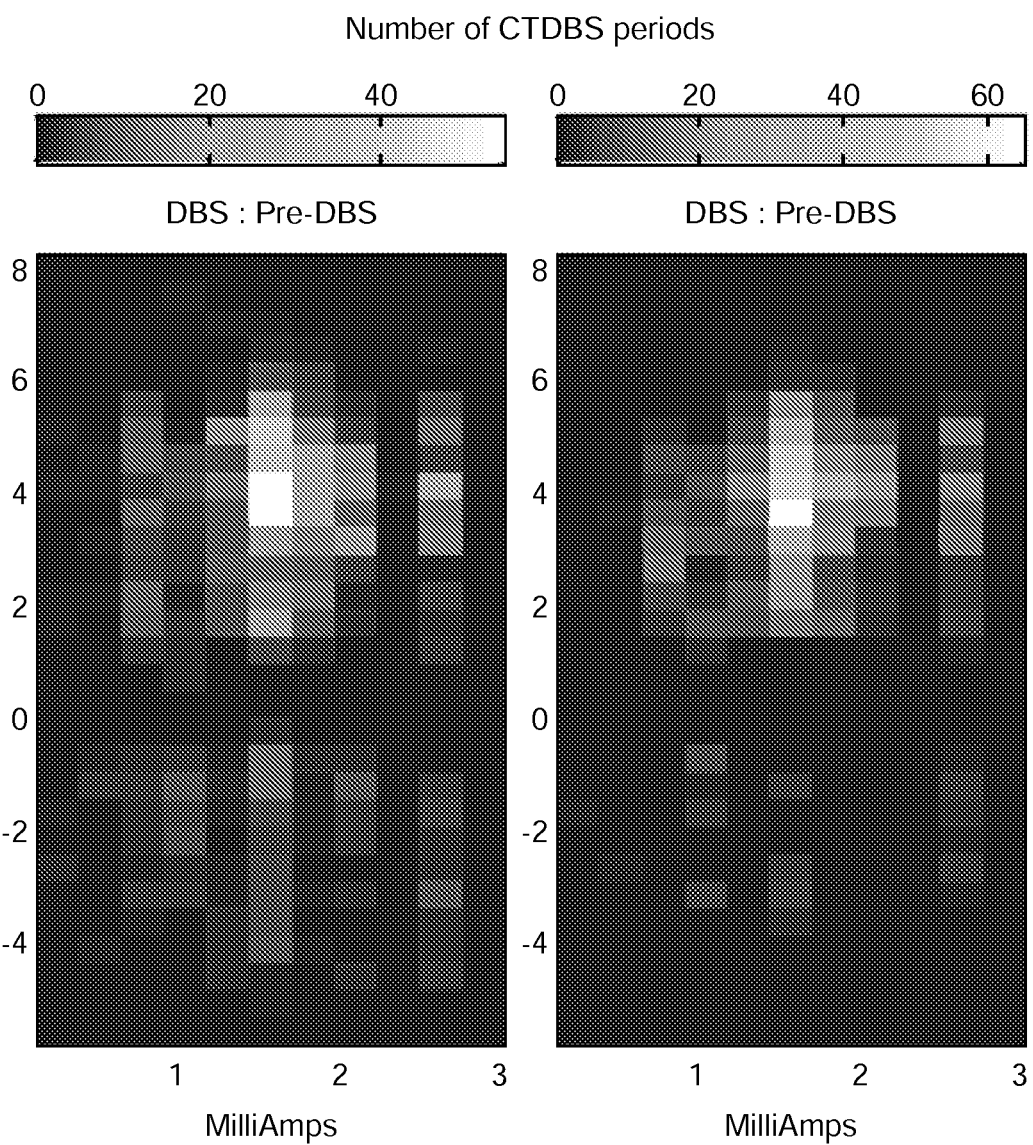
FIGS. 26A and 26B illustrate histograms of significant LOR versus central thalamus deep brain stimulation amplitude.

FIGS. 26A and 26B show histograms of significant LOR versus CTDBS amplitude. FIG. 26A shows LOR of performance during CTDBS/performance prior to CTDBS (N=883) versus CTDBS amplitude. FIG. 26B shows LOR of performance during CTDBS/performance following CTDBS (N=864) versus stimulation amplitude. All amplitudes, frequencies and electrode configurations are included.

Figures 27A, 27B:
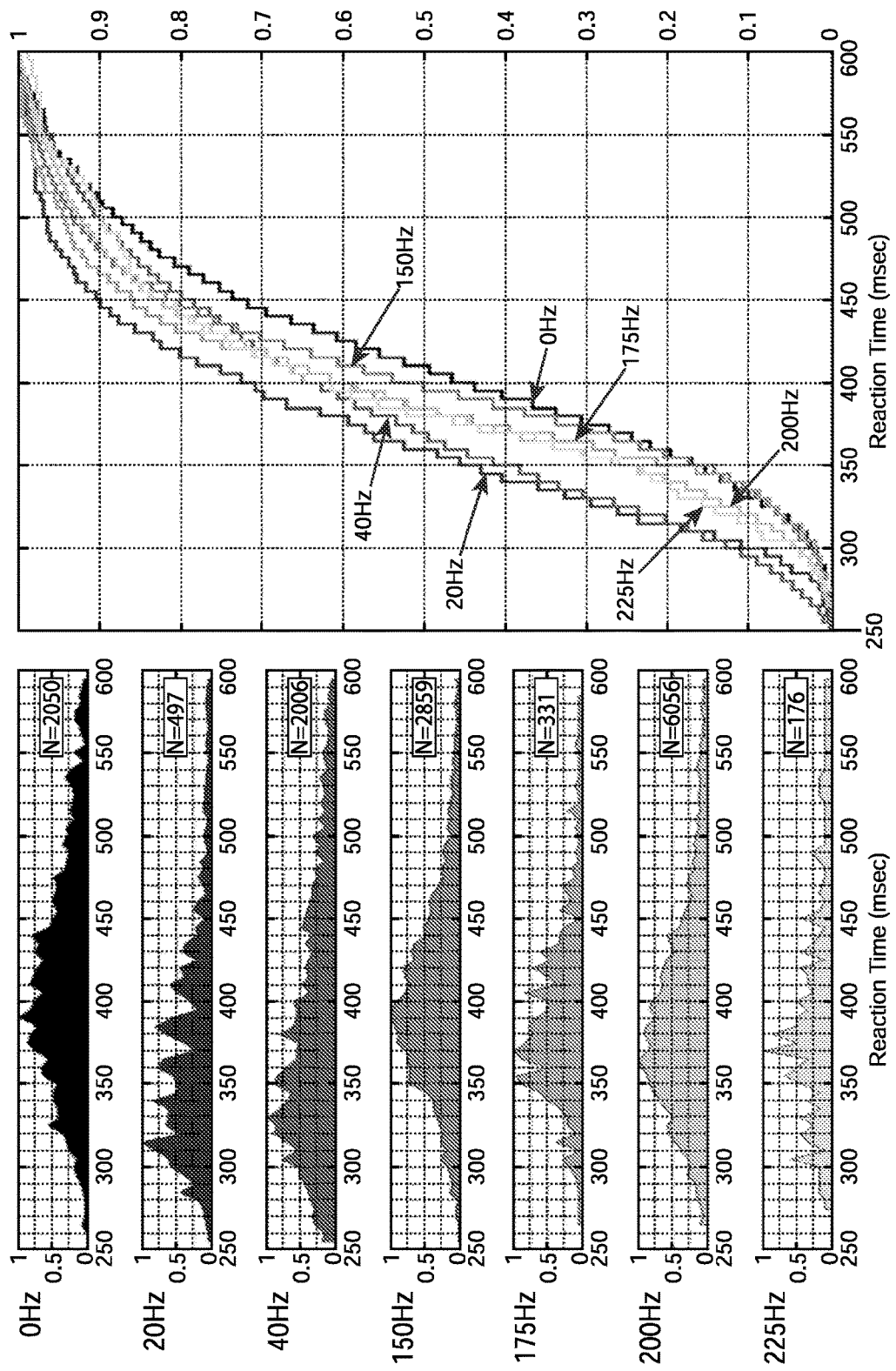
FIGS. 27A and 27B illustrate reaction time distributions during the Vigilance task as illustrated in FIG. 21.

FIGS. 27A and 27B illustrate reaction time distributions during the Vigilance task as illustrated in FIG. 21. FIG. 27A illustrates distributions of reaction times during 165 central thalamus deep brain stimulation sessions (34,502 correct trials) at 20 Hz, 40 Hz, 150 Hz, 175 Hz, 200 Hz, and 225 Hz. FIG. 27B depicts a cumulative distribution function of the reaction time distributions shown FIG. 27A.

Figure 28A:
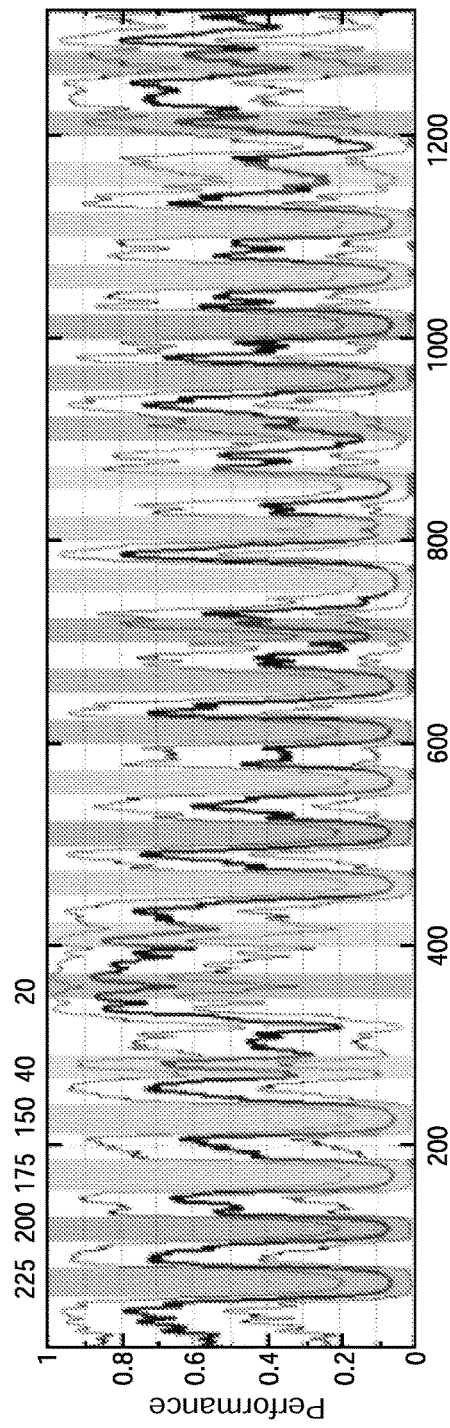
FIGS. 28A and 28B illustrate test results of the second animal's performance during the Vigilance task as illustrated in FIG. 21.
Figure 28B:
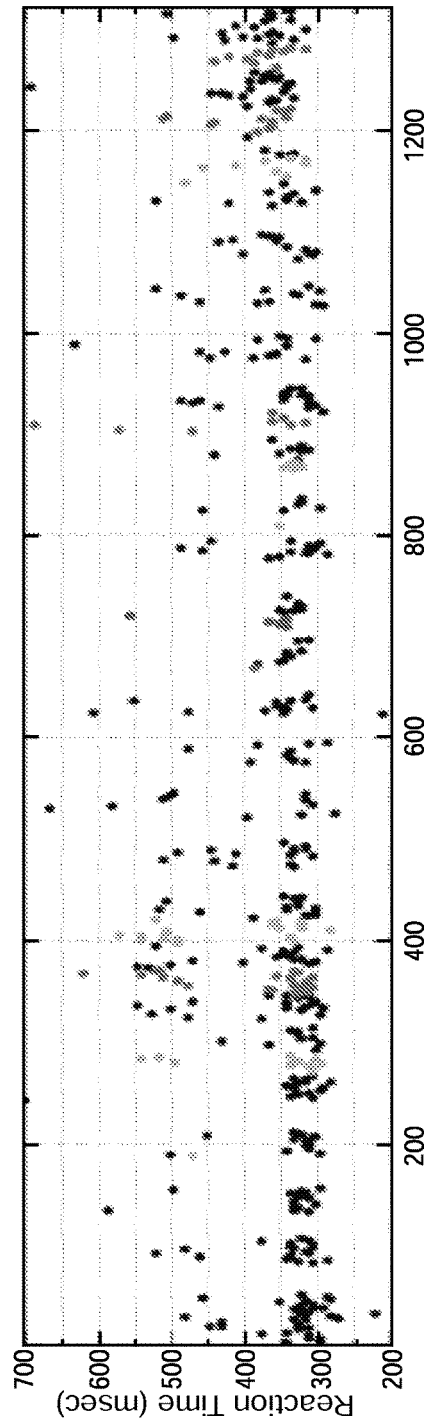

FIGS. 28A and 28B illustrate test results of the second animal's performance during the Vigilance task as illustrated in FIG. 21. FIG. 28A shows the performance profile derived from the State-Space Model as described in Smith et al., "A Bayesian Statistical Analysis of Behavioral Facilitation Associated with Deep Brain Stimulation," *J. Neurosci. Methods* 183(2):267-76 (2009), which is incorporated herein by reference in its entirety, and highlights the causal linkage between periods of continuous 20 Hz, 40 Hz, 150 Hz, 175 Hz, 200 Hz, and 225 Hz central thalamus deep brain stimulation and fluctuations in the animals performance during 1320 contiguous trials. Markings along the zero axis of the performance plot indicate periods of eye closure and somnolence. FIG. 28B shows reaction times plotted as a function of trial number. Black points represent reactions times during central thalamus deep brain stimulation OFF periods and gray points represent reaction times during 20 Hz, 40 Hz, 150 Hz, 175 Hz, 200 Hz, and 225 Hz central thalamus deep brain stimulation ON periods.

Figures 29A, 29B:
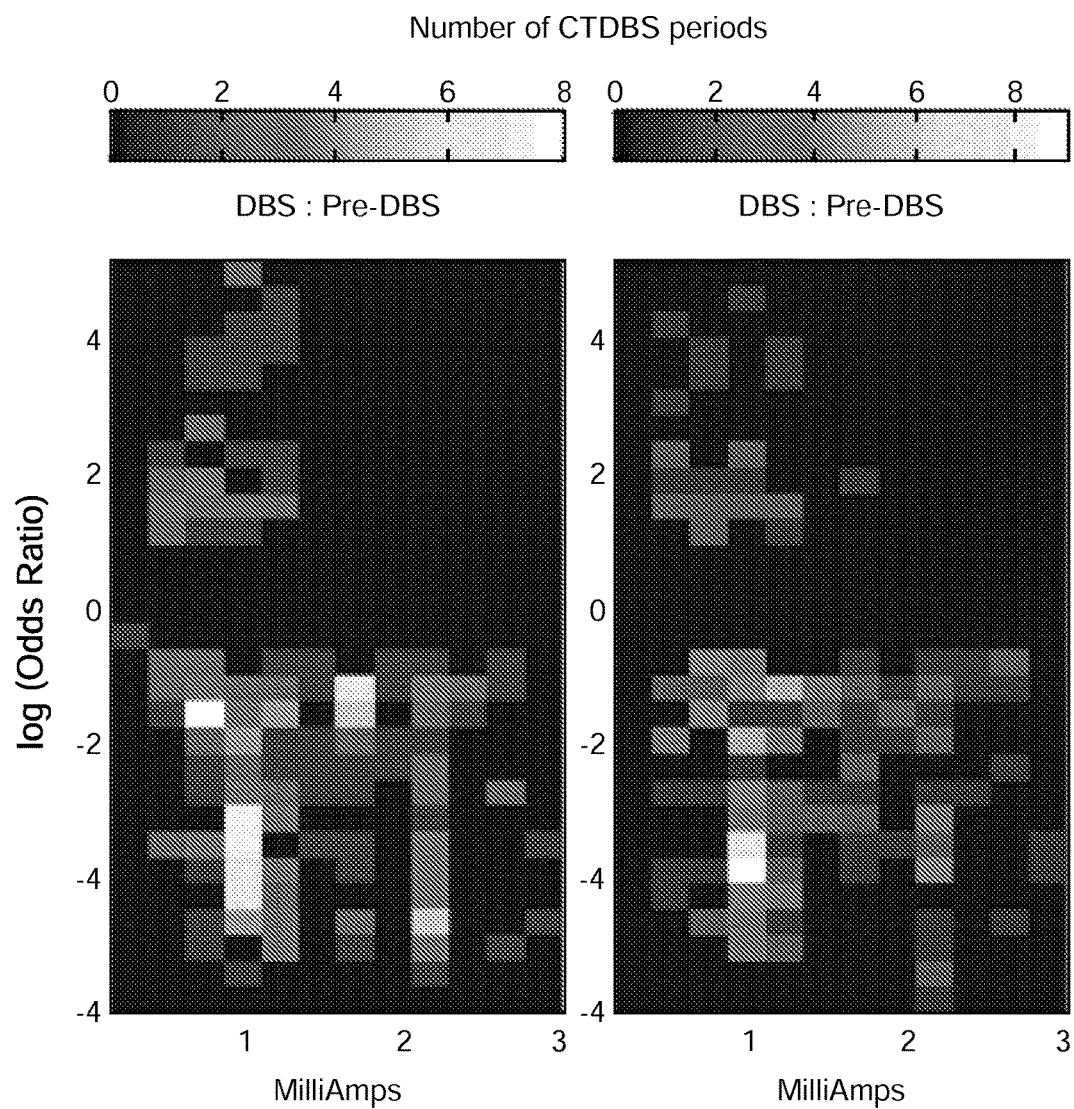
FIGS. 29A and 29B illustrate histograms of significant LOR versus central thalamus deep brain stimulation amplitude.

FIGS. 29A and 29B illustrate histograms of significant LOR versus central thalamus deep brain stimulation amplitude. FIG. 29A shows LOR of performance during central thalamus deep brain stimulation/performance prior to central thalamus deep brain stimulation (N=214) versus central thalamus deep brain stimulation amplitude. FIG. 29B shows LOR of performance during central thalamus deep brain stimulation/performance following central thalamus deep brain stimulation (N=177) versus stimulation amplitude. All amplitudes, frequencies, and electrode configurations are included (N=492) from a total of 33 central thalamus deep brain stimulation sessions.

Figure 30A:
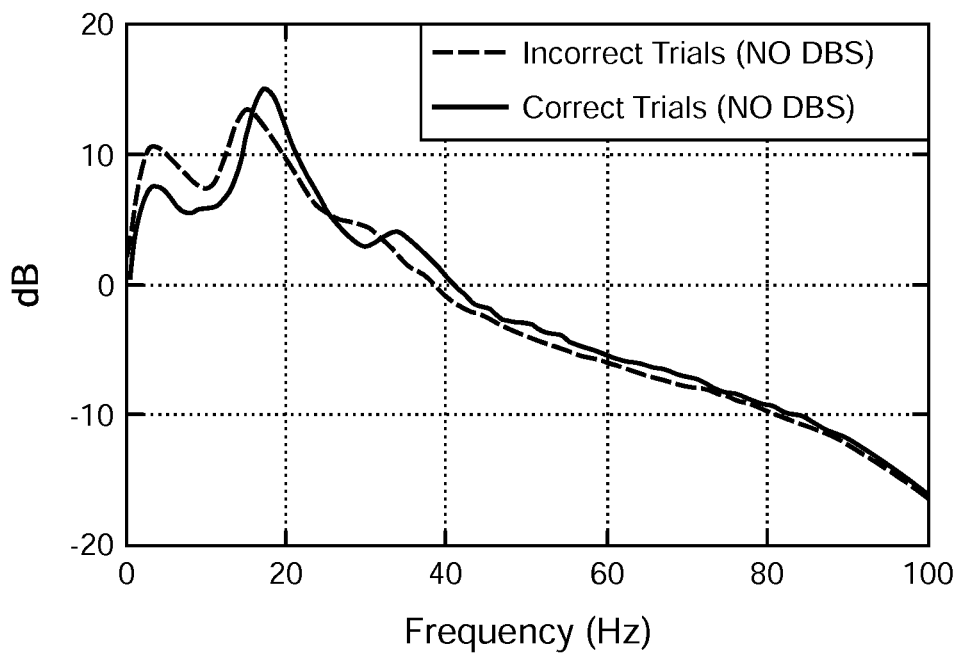
FIGS. 30A-30D illustrate neurophysiology during central thalamus deep brain stimulation.
Figure 30B:
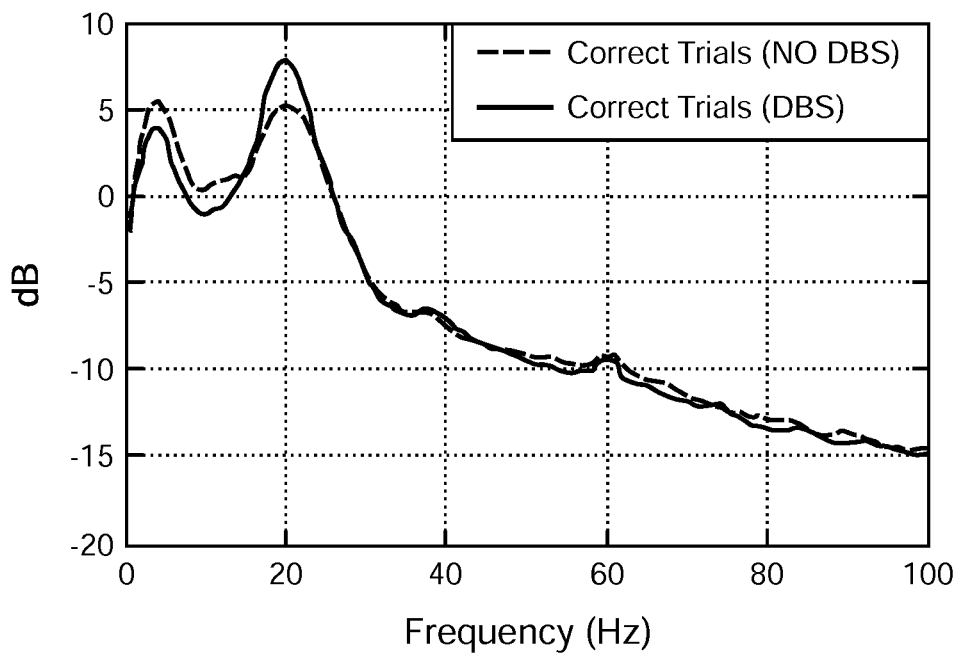
Figure 30C:
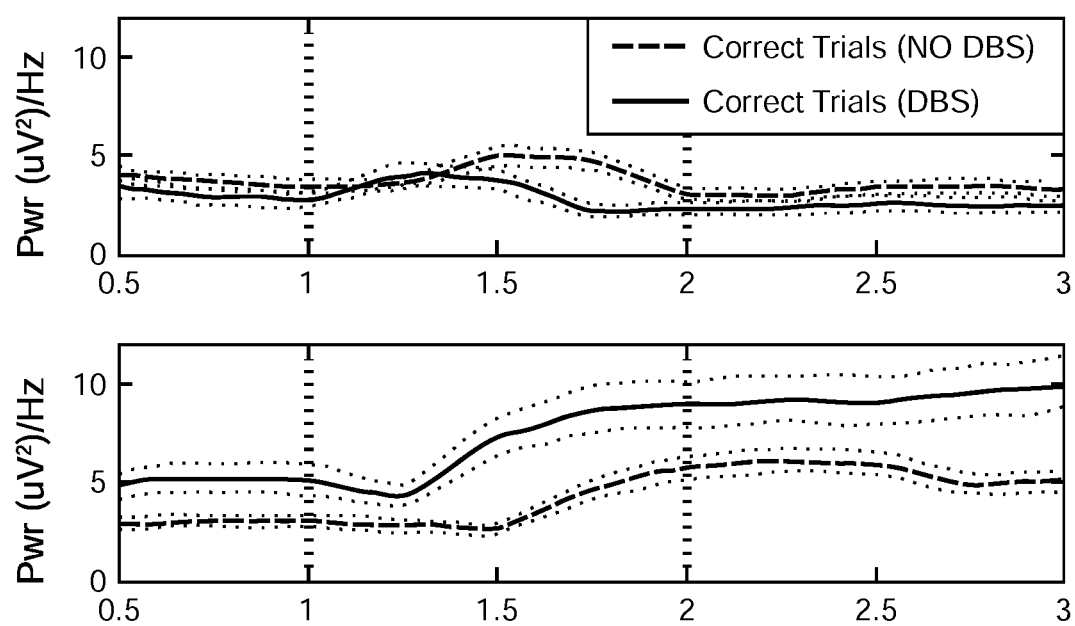
Figure 30D:
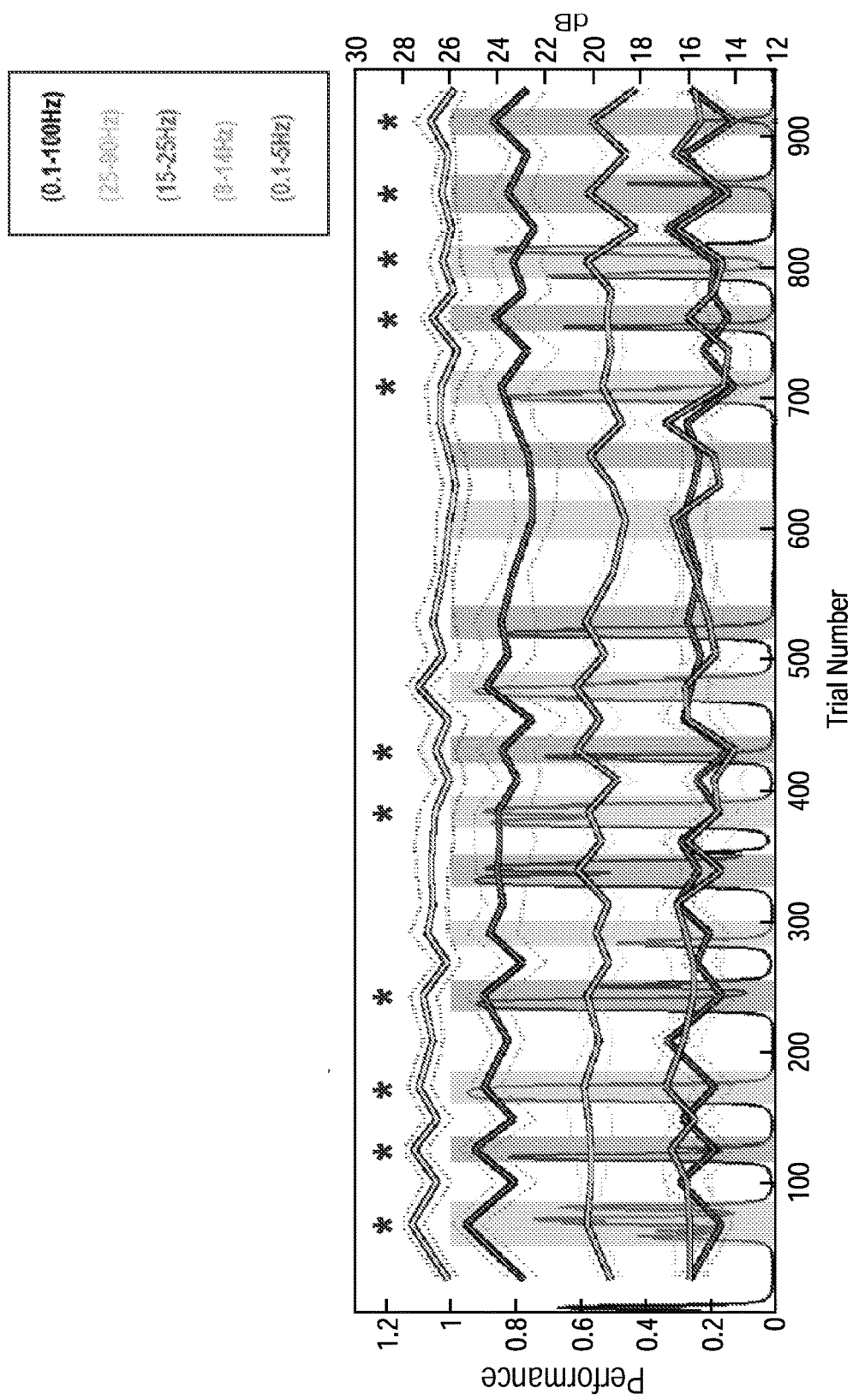

FIGS. 30A-30D illustrate neurophysiology during central thalamus deep brain stimulation. FIG. 30A shows the average local field potential spectra recorded from one electrode positioned within the frontal eye field, containing well-isolated single unit activity. The average local feel potential spectra are separated for Correct and Incorrect trials, excluding all deep brain stimulation trials. FIG. 30B shows average local field potential spectra recorded from one electrode positioned within the dorsal caudate. Only 1.5 seconds of delay period activity in the Correct trials was included and then separated for trials with deep brain stimulation and without deep brain stimulation. FIG. 30C shows the peak local field potential power centered at 5 and 20 Hz (+/−2 Hz) for a single electrode positioned within the dorsal putamen during correct performance. The solid curves represent local field potential power during 200 Hz deep brain stimulation ON periods (188 correct trials) and the dashed curves represent local field potential power during deep brain stimulation OFF periods (137 correct trials). The Pre-Target, Target/Cue and Delay periods are noted and marked by vertical hashed lines (see Vigilance Task as illustrated in FIG. 21). FIG. 30D shows the first animal's performance profile during periods of continuous 150 and 200 Hz central thalamus deep brain stimulation. "Effective" cathode/anode configurations are highlighted with an asterisk. The five superimposed grayscale lines represent integrated power within select frequency bands: total power across the entire frequency range (0.1-100 Hz); power in the delta range (0.1-5 Hz); power in the alpha range (8-14 Hz); power in the beta range (15-25 Hz); power in the gamma range (25-90 Hz). Jackknife estimates of the 95% confidence intervals for each measure of integrated power are indicated by the dotted lines.

Robust and reproducible modulation of behavioral performance was observed in two animals during central thalamic deep brain stimulation (CTDBS). Behavioral modulation was observed in several visuomotor tasks, requiring vigilance and memory guided saccades. Both animal's reaction times and percentage of correct trials were sensitive to a unique subset of DBS parameters.

A significant enhancement within the beta frequency band (15-25 Hz) of the LFP spectra recorded from prefrontal cortex, dorsal striatum, and central thalamus is consistently observed during correct performance in all tasks. The peak frequency and amplitude within the beta band is also significantly influenced by performance enhancing CTDBS.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method to control a thalamic projecting fiber in a subject, said method comprising:
   providing a subject having a first stimulator and a second stimulator implanted in the subject's central thalamus;
   providing a stimulus signal generator coupled to said first and second stimulators; and
   providing separate stimulus signals, from the stimulus signal generator, to the first and second stimulators under conditions effective to control said thalamic projecting fiber in the subject.

2. The method of claim 1, wherein the first stimulator is implanted in the subject's anterior intralaminar nuclei and the second stimulator is implanted in the subject's posterior intralaminar nuclei.

3. The method of claim 1, wherein the first and second stimulators each comprise at least two electrodes.

4. The method of claim 1, wherein said providing separate stimulus signals causes a current to pass between a first electrode located on the first stimulator and a second electrode located on the second stimulator across a fiber bundle of the subject's central thalamus.

5. The method of claim 4, wherein the first electrode located on the first stimulator functions as a cathode and the second electrode located on the second stimulator functions as an anode.

6. The method of claim 5, wherein the direction of current is rostro-caudal.

7. The method of claim 1 further comprising:
providing, in the subject's brain, a further pair of stimulators which receive stimulus signals that are independently controlled by the stimulus signal generator.

8. The method of claim 7, wherein the further pair of stimulators are implanted in separate brain hemispheres.

9. The method of claim 1 further comprising:
providing at least one sensor in communication with the subject's brain.

10. The method of claim 9 further comprising:
providing a state monitoring module;
providing a performance monitoring module; and
providing a processing module, wherein a first sensor is coupled to the state monitoring module and a second sensor is coupled to the performance monitoring module, the state monitoring module, and the performance monitoring module each being coupled to the processing module.

11. The method of claim 10 further comprising:
determining a state of neuronal activity in the subject's brain using said state monitoring module;
determining a performance level of neuronal activity in the subject's brain using said performance monitoring module;
transmitting the state and performance level to the processing module;
extracting a feature vector from the state and performance level using the processing module;
computing a response stimulus signal based upon a comparison between the extracted feature vector and a pre-stored feature vector using the processing module; and
transmitting the response stimulus signal to the stimulus signal generator using a transmission module.

12. The method of claim 1 further comprising:
selecting a subject with a neurological disease or condition selected from the group consisting of: impaired cognitive function, epilepsy, a movement disorder, a neuropsychiatric illness, pain, a brain injury, a developmental disorder, and a neurodegenerative disorder, wherein carrying out said method is carried out on said selected subject under conditions effective to treat the neurological disease or condition.

13. The method of claim 1 further comprising:
selecting a subject with a neuropsychiatric disease or condition, wherein said method is carried out on said selected subject under conditions effective to treat the neuropsychiatric disease or condition.

14. The method of claim 1, wherein said method is carried out under conditions effective to control intrathalamic dynamics in the subject.

15. The method of claim 1, wherein said method is carried out under conditions effective to control thalamostriatal dynamics in the subject.

16. The method of claim 1, wherein said method is carried out under conditions effective to control thalamocortical dynamics in the subject.

17. The method of claim 1 further comprising:
implanting the first stimulator and the second stimulator in the subject's central thalamus.

18. An apparatus for deep brain stimulation, said apparatus comprising:
at least a first stimulator and a second stimulator configured to be inserted in a subject's central thalamus, wherein the first stimulator and the second stimulator comprise one or more electrodes;
a stimulus signal generator coupled to said first and second stimulators, the stimulus signal generator configured to provide stimulus signals to the first and second stimulators, wherein the stimulus signal generator selectively provides the stimulus signals to at least one of the one or more electrodes of the first and second stimulators causing a current to flow between the first stimulator and the second stimulator across a fiber bundle of the subject's central thalamus;
at least a first sensor and a second sensor configured to detect neuronal activity;
an adaptive feedback controller coupled to the first and second stimulators and the first and second sensors, the adaptive feedback controller comprising a processor and a memory coupled to the processor which is configured to execute one or more programmed instructions stored in the memory to:
receive neuronal activity data for the subject's central thalamus from the first and second sensors;
determine a state and performance level of the subject's central thalamus based on the neuronal activity data;
extract a feature vector from the state and performance levels; and
compute a response stimulus signal based upon a comparison of the extracted feature vector to a prestored feature vector; and
transmit the response stimulus to the stimulus signal generator to control a thalamic projecting fiber in the subject.

19. The apparatus of claim 18 further comprising:
a further pair of stimulators which receive stimulus signals that are independently controlled by the stimulus signal generator.

20. A method for regulating arousal level in a selected subject, the method comprising:
providing the selected subject having a first stimulator and a second stimulator implanted in the subject's central thalamus;
providing a stimulus signal generator coupled to said first and second stimulators; and
providing separate stimulus signals, from the stimulus signal generator, to the first and second stimulators under conditions effective to regulate the arousal level of the subject.

21. The method of claim 20 further comprising:
providing a non-transitory computer readable medium having stored thereon machine executable code which when executed by a processor, causes the processor to perform steps comprising:
detecting a level of neuronal activity in the selected subject's brain; and
generating and sending a response stimulus signal to the subject's brain in response to the detected neuronal activity level under conditions effective to regulate the arousal level of the subject.

22. The method of claim 20 further comprising:
implanting the first stimulator and the second stimulator in the subject's central thalamus.

23. A method for suppressing seizure activity in a selected subject, the method comprising:
providing the selected subject having a first stimulator and a second stimulator implanted in the subject's central thalamus;
providing a stimulus signal generator coupled to said first and second stimulators; and providing separate stimulus signals, from the stimulus signal generator, to the first and second stimulators under conditions effective to suppress seizure activity in the subject.

24. The method of claim 23 further comprising:
providing a non-transitory computer readable medium having stored thereon machine executable code which when executed by a processor, causes the processor to perform steps comprising:
detecting a level of neuronal activity in the selected subject's brain; and
generating and sending a response stimulus signal to the subject's brain in response to the detected neuronal activity level under conditions effective to suppress seizure activity in the subject.

25. The method of claim 23 further comprising:
implanting the first stimulator and the second stimulator in the subject's central thalamus.

26. A method for normalizing movement in a selected subject, the method comprising:
providing the selected subject having a first stimulator and a second stimulator implanted in the subject's central thalamus;
providing a stimulus signal generator coupled to said first and second stimulators; and
providing separate stimulus signals, from the stimulus signal generator, to the first and second stimulators under conditions effective to normalize movement in the selected subject.

27. The method of claim 26 further comprising:
providing a non-transitory computer readable medium having stored thereon machine executable code which when executed by a processor, causes the processor to perform steps comprising:
detecting a level of neuronal activity in the selected subject's brain; and
generating and sending a response stimulus signal to the subject's brain in response to the detected neuronal activity level under conditions effective to normalize movement in the subject.

28. The method of claim 26 further comprising:
implanting the first stimulator and the second stimulator in the subject's central thalamus.

* * * * *

UNITED STATES PATENT AND TRADEMARK OFFICE
CERTIFICATE OF CORRECTION

PATENT NO. : 9,592,383 B2
APPLICATION NO. : 14/762616
DATED : March 14, 2017
INVENTOR(S) : Schiff et al.

Page 1 of 1

It is certified that error appears in the above-identified patent and that said Letters Patent is hereby corrected as shown below:

At Column 1, Lines 7-10, please delete the following paragraph:
"This invention was made with government support under grant number NS067249 awarded by National Institute of Neurological Disorders and Stroke. The government has certain rights in this invention."

And insert the following paragraph:
--This invention was made with government support under Grant Number NS067249 awarded by the National Institutes of Health. The Government has certain rights in the invention.--

Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*